(12) United States Patent
Little, II et al.

(10) Patent No.: US 6,664,231 B1
(45) Date of Patent: *Dec. 16, 2003

(54) ANTI-FUNGAL PEPTIDES

(75) Inventors: Roger G. Little, II, Benicia, CA (US);
Edward Lim, Walnut Creek, CA (US);
Mitchell B. Fadem, Berkeley, CA (US)

(73) Assignee: Xoma Corporation, Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/677,664

(22) Filed: Oct. 2, 2000

Related U.S. Application Data

(63) Continuation of application No. 09/227,659, filed on Jan. 8, 1999, now Pat. No. 6,156,730, which is a continuation of application No. 08/621,259, filed on Mar. 21, 1996, now Pat. No. 5,858,974, which is a continuation-in-part of application No. 08/504,841, filed on Jul. 20, 1995, now abandoned, which is a continuation-in-part of application No. 08/372,105, filed on Jan. 13, 1995, now Pat. No. 5,627,153, which is a continuation-in-part of application No. 08/306,473, filed on Sep. 15, 1994, now Pat. No. 5,652,332, and a continuation-in-part of application No. 08/273,540, filed on Jul. 11, 1994, now abandoned, which is a continuation-in-part of application No. 08/209,762, filed on Mar. 11, 1994, now Pat. No. 5,733,872, which is a continuation-in-part of application No. 08/183,222, filed on Jan. 14, 1994, now abandoned, which is a continuation-in-part of application No. 08/093,202, filed on Jul. 15, 1993, now abandoned, which is a continuation-in-part of application No. 08/030,644, filed on Mar. 12, 1993, now Pat. No. 5,348,942.

(51) Int. Cl.$^7$ .............................................. A61K 38/00
(52) U.S. Cl. .............................. 514/14; 514/18; 514/2; 530/300; 530/317
(58) Field of Search ................................ 514/4, 11, 12, 514/13, 14, 15, 16, 17; 530/300, 317, 324, 327, 328, 329

(56) References Cited

U.S. PATENT DOCUMENTS

| | | | | | |
|---|---|---|---|---|---|
| 5,627,153 A | * | 5/1997 | Little, II et al. | .............. | 514/12 |
| 5,858,974 A | * | 1/1999 | Little, II et al. | .............. | 514/12 |
| 6,156,730 A | * | 12/2000 | Little, II et al. | .............. | 514/12 |

* cited by examiner

*Primary Examiner*—Christopher R. Tate
*Assistant Examiner*—Roy Teller
(74) *Attorney, Agent, or Firm*—McAndrews, Held & Malloy, Ltd.

(57) ABSTRACT

The present invention relates generally to anti-fungal peptides derived from or based on Domain III (amino acids 142–169) of bactericidal/permeability-increasing protein (BPI) and in vivo or in vitro uses of such peptides.

43 Claims, 10 Drawing Sheets

SEQUENCE LISTING (1) GENERAL INFORMATION:

(iii) NUMBER OF SEQUENCES: 257

(2) INFORMATION FOR SEQ ID NO: 1:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.5"

(ix) FEATURE:
        (A) NAME/KEY: Modified-site
        (B) LOCATION: C-Terminus
        (D) OTHER INFORMATION: /label= Amidation /note= "
        The C-Terminus is Amidated."

(xi) SEQUENCE DESCRIPTION: SEQ ID NO: 1:

Val His Val His Ile Ser Lys Ser Lys Val Gly Trp Leu Ile Gln Leu
1               5                   10                  15

Phe His Lys Lys Ile Glu
            20

(2) INFORMATION FOR SEQ ID NO: 2:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.11"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 2:

Lys Ser Lys Val Trp Leu Ile Gln Leu Phe His Lys Lys
1               5                   10

(2) INFORMATION FOR SEQ ID NO: 3:

(i) SEQUENCE CHARACTERISTICS:
        (A) LENGTH: 29 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.12"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 3:

Ser Val His Val His Ile Ser Lys Ser Lys Val Gly Trp Leu Ile Gln
1               5                   10                  15

Leu Phe His Lys Lys Ile Glu Ser Ala Leu Arg Asn Lys
                20                  25

(2) INFORMATION FOR SEQ ID NO: 4:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.13"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 4:

Lys Ser Lys Val Gly Trp Leu Ile Gln Leu Phe His Lys Lys
1               5                   10

(2) INFORMATION FOR SEQ ID NO: 5:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.29"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 5:

Lys Ser Lys Val Gly Trp Leu Ile Gln Leu Phe His Lys Lys Ser
1               5                   10                  15

Lys Val Gly Trp Leu Ile Gln Leu Phe His Lys Lys
                20                  25

(2) INFORMATION FOR SEQ ID NO: 6:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.31"

(ix) FEATURE:
        (A) NAME/KEY: Modified-site
        (B) LOCATION: C-Terminus (D) OTHER INFORMATION: /label= Amidation /note=
            "The C-Terminus is Amidated."

(xi) SEQUENCE DESCRIPTION: SEQ ID NO: 6:

Ala Ser Lys Val Gly Trp Leu Ile Gln Leu Phe His Lys Lys
1               5                   10

(2) INFORMATION FOR SEQ ID NO: 7:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.32"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 7:

Lys Ala Lys Val Gly Trp Leu Ile Gln Leu Phe His Lys Lys
1               5                   10

(2) INFORMATION FOR SEQ ID NO: 8:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.33"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 8:

Lys Ser Ala Val Gly Trp Leu Ile Gln Leu Phe His Lys Lys
1               5                   10

(2) INFORMATION FOR SEQ ID NO: 9:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.34"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 9:

```
Lys Ser Lys Ala Gly Trp Leu Ile Gln Leu Phe His Lys Lys
1               5                   10
```

(2) INFORMATION FOR SEQ ID NO: 10:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.35"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 10:

```
Lys Ser Lys Val Ala Trp Leu Ile Gln Leu Phe His Lys Lys
1               5                   10
```

(2) INFORMATION FOR SEQ ID NO: 11:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.36"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 11:

```
Lys Ser Lys Val Gly Ala Leu Ile Gln Leu Phe His Lys Lys
1               5                   10
```

(2) INFORMATION FOR SEQ ID NO: 12:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.37"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 12:

```
Lys Ser Lys Val Gly Trp Ala Ile Gln Leu Phe His Lys Lys
1               5                   10
```

(2) INFORMATION FOR SEQ ID NO: 13:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.38"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 13:

Lys Ser Lys Val Gly Trp Leu Ala Gln Leu Phe His Lys Lys
1            5                   10

(2) INFORMATION FOR SEQ ID NO: 14:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.39"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 14:

Lys Ser Lys Val Gly Trp Leu Ile Ala Leu Phe His Lys Lys
1            5                   10

(2) INFORMATION FOR SEQ ID NO: 15:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.40"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 15:

Lys Ser Lys Val Gly Trp Leu Ile Gln Ala Phe His Lys Lys
1            5                   10

(2) INFORMATION FOR SEQ ID NO: 16:

(i) SEQUENCE CHARACTERISTICS:

```
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.41"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 16:

Lys Ser Lys Val Gly Trp Leu Ile Gln Leu Ala His Lys Lys
1               5                   10

(2) INFORMATION FOR SEQ ID NO: 17:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.42"

(ix) FEATURE:
        (A) NAME/KEY: Modified-site
        (B) LOCATION: C-Terminus
        (D) OTHER INFORMATION: /label= Amidation  /note=
            "The C-Terminus is Amidated."

(xi) SEQUENCE DESCRIPTION: SEQ ID NO: 17:

Lys Ser Lys Val Gly Trp Leu Ile Gln Leu Phe Ala Lys Lys
1               5                   10

(2) INFORMATION FOR SEQ ID NO: 18:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.43"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 18:

Lys Ser Lys Val Gly Trp Leu Ile Gln Leu Phe His Ala Lys
1               5                   10

(2) INFORMATION FOR SEQ ID NO: 19:

(i) SEQUENCE CHARACTERISTICS:
        (A) LENGTH: 14 amino acids
        (B) TYPE: amino acid
        (D) TOPOLOGY: linear
```

```
        (ii) MOLECULE TYPE: peptide (ix) FEATURE:
             (A) NAME/KEY: misc_feature
             (D) OTHER INFORMATION: "XMP.44"

(ix) FEATURE:
             (A) NAME/KEY: Modified-site
             (B) LOCATION: C-Terminus
             (D) OTHER INFORMATION: /label= Amidation /note=
                 "The C-Terminus is Amidated."

(xi) SEQUENCE DESCRIPTION: SEQ ID NO: 19:

Lys Ser Lys Val Gly Trp Leu Ile Gln Leu Phe His Lys Ala
1               5                   10

(2) INFORMATION FOR SEQ ID NO: 20:

(i) SEQUENCE CHARACTERISTICS:
             (A) LENGTH: 21 amino acids
             (B) TYPE: amino acid
             (D) TOPOLOGY: linear (ii) MOLECULE TYPE: peptide (ix) FEATURE:
             (A) NAME/KEY: misc_feature
             (D) OTHER INFORMATION: "XMP.55"

(ix) FEATURE:
             (A) NAME/KEY: Modified-site
             (B) LOCATION: C-Terminus
             (D) OTHER INFORMATION: /label= Amidation /note=
                 "The C-Terminus is Amidated."

(xi) SEQUENCE DESCRIPTION: SEQ ID NO: 20:

Gly Trp Leu Ile Gln Leu Phe His Lys Lys Ile Glu Ser Ala Leu Arg
1               5                   10                  15

Asn Lys Met Asn Ser
            20

(2) INFORMATION FOR SEQ ID NO: 21:

(i) SEQUENCE CHARACTERISTICS:
             (A) LENGTH: 14 amino acids
             (B) TYPE: amino acid
             (D) TOPOLOGY: linear (ii) MOLECULE TYPE: peptide (ix) FEATURE:
             (A) NAME/KEY: misc_feature
             (D) OTHER INFORMATION: "XMP.82"

(ix) FEATURE:
             (A) NAME/KEY: Modified-site
             (B) LOCATION: C-Terminus
             (D) OTHER INFORMATION: /label= Amidation /note=
                 "The C-Terminus is Amidated."

(xi) SEQUENCE DESCRIPTION: SEQ ID NO: 21:

Lys Ser Lys Val Gly Trp Leu Ile Gln Leu Trp His Lys Lys
1               5                   10

(2) INFORMATION FOR SEQ ID NO: 22:

(i) SEQUENCE CHARACTERISTICS:
             (A) LENGTH: 14 amino acids
             (B) TYPE: amino acid
             (D) TOPOLOGY: linear (ii) MOLECULE TYPE: peptide
```

(ix) FEATURE:
            (A) NAME/KEY: misc_feature
            (D) OTHER INFORMATION: "XMP.83"

(ix) FEATURE:
            (A) NAME/KEY: Modified-site
            (B) LOCATION: 6
            (D) OTHER INFORMATION: /label= Substituted-Ala /note=
                "Position 6 is beta-1-naphthyl-substituted"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 22:

Lys Ser Lys Val Gly Ala Leu Ile Gln Leu Phe His Lys Lys
1               5                   10

(2) INFORMATION FOR SEQ ID NO: 23:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.85"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 23:

Lys Ser Lys Val Leu Trp Leu Ile Gln Leu Phe His Lys Lys
1               5                   10

(2) INFORMATION FOR SEQ ID NO: 24:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.86"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 24:

Lys Ser Lys Val Gly Trp Leu Ile Leu Leu Phe His Lys Lys
1               5                   10

(2) INFORMATION FOR SEQ ID NO: 25:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
    (A) NAME/KEY: misc_feature
    (D) OTHER INFORMATION: "XMP.87"

(ix) FEATURE:
    (A) NAME/KEY: Modified-site
    (B) LOCATION: C-Terminus
    (D) OTHER INFORMATION: /label= Amidation /note= "The C-Terminus is Amidated."

(xi) SEQUENCE DESCRIPTION: SEQ ID NO: 25:

```
Lys Ser Lys Val Gly Trp Leu Ile Gln Leu Phe Leu Lys Lys
1               5                   10
```

(2) INFORMATION FOR SEQ ID NO: 26:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
    (A) NAME/KEY: misc_feature
    (D) OTHER INFORMATION: "XMP.91"

(ix) FEATURE:
    (A) NAME/KEY: Modified-site
    (B) LOCATION: C-Terminus
    (D) OTHER INFORMATION: /label= Amidation /note= "The C-Terminus is Amidated."

(xi) SEQUENCE DESCRIPTION: SEQ ID NO: 26:

```
Lys Ser Lys Val Gly Trp Leu Ile Phe Leu Phe His Lys Lys
1               5                   10
```

(2) INFORMATION FOR SEQ ID NO: 27:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
    (A) NAME/KEY: misc_feature
    (D) OTHER INFORMATION: "XMP.92"

(ix) FEATURE:
    (A) NAME/KEY: Modified-site
    (B) LOCATION: C-Terminus
    (D) OTHER INFORMATION: /label= Amidation /note= "The C-Terminus is Amidated."

(xi) SEQUENCE DESCRIPTION: SEQ ID NO: 27:

```
Lys Ser Lys Val Gly Trp Leu Ile Lys Leu Phe His Lys Lys
1               5                   10
```

(2) INFORMATION FOR SEQ ID NO: 28:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:

(A) NAME/KEY: misc_feature
            (D) OTHER INFORMATION: "XMP.94"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 28:

Lys Ser Lys Val Gly Trp Leu Ile Gln Leu Phe Phe Lys Lys
1               5                   10

(2) INFORMATION FOR SEQ ID NO: 29:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.95"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 29:

Lys Ser Lys Val Phe Trp Leu Ile Gln Leu Phe His Lys Lys
1               5                   10

(2) INFORMATION FOR SEQ ID NO: 30:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.96"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 30:

Lys Ser Lys Val Gly Trp Leu Ile Gln Leu Phe His Lys Phe
1               5                   10

(2) INFORMATION FOR SEQ ID NO: 31:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.97"

(ix) FEATURE:

```
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 31:

Lys Ser Lys Val Lys Trp Leu Ile Gln Leu Phe His Lys Lys
1               5                   10

(2) INFORMATION FOR SEQ ID NO: 32:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.100"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 32:

Lys Ser Lys Val Lys Trp Leu Ile Lys Leu Phe His Lys Lys
1               5                   10

(2) INFORMATION FOR SEQ ID NO: 33:

(i) SEQUENCE CHARACTERISTICS:
            (A) LENGTH: 28 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.101"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 33:

Lys Ser Lys Val Lys Trp Leu Ile Lys Leu Phe Phe Lys Phe Lys Ser
1               5                   10                  15
Lys Val Lys Trp Leu Ile Lys Leu Phe Phe Lys Phe
                20                  25

(2) INFORMATION FOR SEQ ID NO: 34:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.104"

(ix) FEATURE:
            (A) NAME/KEY: Modified-site
```

(B) LOCATION: C-Terminus
            (D) OTHER INFORMATION: /label= Amidation /note=
                "The C-Terminus is Amidated."

(xi) SEQUENCE DESCRIPTION: SEQ ID NO: 34:

Lys Ser Lys Val Gly Trp Leu Ile Ser Leu Phe His Lys Lys
1               5                   10

(2) INFORMATION FOR SEQ ID NO: 35:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.106"

(ix) FEATURE:
        (A) NAME/KEY: Modified-site
        (B) LOCATION: C-Terminus
        (D) OTHER INFORMATION: /label= Amid /note=
                "The C-Terminus is Amidated."

(xi) SEQUENCE DESCRIPTION: SEQ ID NO: 35:

Lys Ser Lys Val Gly Trp Leu Ile Thr Leu Phe His Lys Lys
1               5                   10

(2) INFORMATION FOR SEQ ID NO: 36:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.107"

(ix) FEATURE:
        (A) NAME/KEY: Modified-site
        (B) LOCATION: C-Terminus
        (D) OTHER INFORMATION: /label= Amidation /note=
                "The C-Terminus is Amidated."

(xi) SEQUENCE DESCRIPTION: SEQ ID NO: 36:

Lys Ser Lys Val Gly Trp Leu Ile Gln Leu Phe Trp Lys Lys
1               5                   10

(2) INFORMATION FOR SEQ ID NO: 37:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.108"

(ix) FEATURE:
        (A) NAME/KEY: Modified-site
        (B) LOCATION: C-Terminus
        (D) OTHER INFORMATION: /label= Amid /note=
                "The C-Terminus is Amidated."

(xi) SEQUENCE DESCRIPTION: SEQ ID NO: 37:

Lys Ser Lys Val Gly Trp Leu Ile Gln Leu Phe His Lys Trp
1               5                   10

(2) INFORMATION FOR SEQ ID NO: 38:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.109"

(ix) FEATURE:
        (A) NAME/KEY: Modified-site
        (B) LOCATION: 11
        (D) OTHER INFORMATION: /label= Substituted-Ala /note=
        "Position 11 is beta-1-naphthyl-substituted."

(ix) FEATURE:
        (A) NAME/KEY: Modified-site
        (B) LOCATION: C-Terminus
        (D) OTHER INFORMATION: /label= Amid /note=
        "The C-Terminus is Amidated."

(xi) SEQUENCE DESCRIPTION: SEQ ID NO: 38:

Lys Ser Lys Val Gly Trp Leu Ile Gln Leu Ala His Lys Lys
1               5                   10

(2) INFORMATION FOR SEQ ID NO: 39:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.110"

(ix) FEATURE:
        (A) NAME/KEY: Modified-site
        (B) LOCATION: 12
        (D) OTHER INFORMATION: /label= Subst /note=
        "Position 12 is beta-1-naphthyl-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 39:

Lys Ser Lys Val Gly Trp Leu Ile Gln Leu Phe Ala Lys Lys
1               5                   10

(2) INFORMATION FOR SEQ ID NO: 40:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature (D) OTHER INFORMATION: "XMP.111"

(ix) FEATURE:
            (A) NAME/KEY: Modified-site
            (B) LOCATION: 14
            (D) OTHER INFORMATION: /label= Substituted-Ala /note=
                "Position 14 is beta-1-naphthyl-substituted."

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 40:

Lys Ser Lys Val Gly Trp Leu Ile Gln Leu Phe His Lys Ala
1               5                   10

(2) INFORMATION FOR SEQ ID NO: 41:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.113"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 41:

Lys Ser Lys Val Gly Trp Leu Ile Gln Phe Phe His Lys Lys
1               5                   10

(2) INFORMATION FOR SEQ ID NO: 42:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.116"

(ix) FEATURE:
            (A) NAME/KEY: Modified-site
            (B) LOCATION: 6
            (D) OTHER INFORMATION: /label= Substituted-Ala /note=
                "Position 6 is beta-1-naphthyl-substituted."

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 42:

Lys Ser Lys Val Lys Ala Leu Ile Gln Leu Phe His Lys Lys
1               5                   10

(2) INFORMATION FOR SEQ ID NO: 43:

(i) SEQUENCE CHARACTERISTICS:

```
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.123"

(ix) FEATURE:
        (A) NAME/KEY: Modified-site
        (B) LOCATION: 9
        (D) OTHER INFORMATION: /label= Substituted-Phe /note=
        "The phenylalanine at position 9 is p-amino-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 43:

Lys Ser Lys Val Gly Trp Leu Ile Phe Leu Phe His Lys Lys
 1               5                  10

(2) INFORMATION FOR SEQ ID NO: 44:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.124"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 44:

Lys Ser Lys Val Lys Trp Leu Ile Gln Leu Trp His Lys Lys
 1               5                  10

(2) INFORMATION FOR SEQ ID NO: 45:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.125"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 45:

Lys Ser Lys Val Gly Trp Leu Ile Tyr Leu Phe His Lys Lys
 1               5                  10

(2) INFORMATION FOR SEQ ID NO: 46:
```

```
    (i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.126"

(ix) FEATURE:
        (A) NAME/KEY: Modified-site
        (B) LOCATION: 6
        (D) OTHER INFORMATION: /label= D-Trp /note=
        "Position 6 is D-tryptophan."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 46:

Lys Ser Lys Val Gly Trp Leu Ile Gln Leu Phe His Lys Lys
1               5                   10

(2) INFORMATION FOR SEQ ID NO: 47:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.127"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 47:

Lys Ser Lys Val Gly Phe Leu Ile Gln Leu Phe His Lys Lys
1               5                   10

(2) INFORMATION FOR SEQ ID NO: 48:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.128"

(ix) FEATURE:
        (A) NAME/KEY: Modified-site
        (B) LOCATION: 6
        (D) OTHER INFORMATION: /label= D-Phe /note=
        "Position 6 is D-phenylalanine."

(ix) FEATURE:
        (A) NAME/KEY: Modified-site
        (B) LOCATION: C-Terminus
        (D) OTHER INFORMATION: /label= Amidation /note=
        "The C-Terminus is Amidated."
```

(xi) SEQUENCE DESCRIPTION: SEQ ID NO: 48:

Lys Ser Lys Val Gly Phe Leu Ile Gln Leu Phe His Lys Lys
 1               5                  10

(2) INFORMATION FOR SEQ ID NO: 49:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.129"

(ix) FEATURE:
        (A) NAME/KEY: Modified-site
        (B) LOCATION: 6
        (D) OTHER INFORMATION: /label= Substituted-Ala /note=
        "Position 6 is D-1-beta-1-naphthyl-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 49:

Lys Ser Lys Val Gly Ala Leu Ile Gln Leu Phe His Lys Lys
 1               5                  10

(2) INFORMATION FOR SEQ ID NO: 50:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.130"

(ix) FEATURE:
        (A) NAME/KEY: Modified-site
        (B) LOCATION: 6
        (D) OTHER INFORMATION: /label= Substituted-Ala /note=
        "Position 6 is beta-2-naphthyl-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 50:

Lys Ser Lys Val Gly Ala Leu Ile Gln Leu Phe His Lys Lys
 1               5                  10

(2) INFORMATION FOR SEQ ID NO: 51:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:

(A) NAME/KEY: misc_feature
        (D) OTHER INFORMATION: "XMP.131"

(ix) FEATURE:
        (A) NAME/KEY: Modified-site
        (B) LOCATION: 6
        (D) OTHER INFORMATION: /label= Substituted-Ala /note=
        "Position 6 is D-beta-2-naphthyl-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 51:

Lys Ser Lys Val Gly Ala Leu Ile Gln Leu Phe His Lys Lys
1               5                   10

(2) INFORMATION FOR SEQ ID NO: 52:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.132"

(ix) FEATURE:
        (A) NAME/KEY: Modified-site
        (B) LOCATION: 6
        (D) OTHER INFORMATION: /label= Substituted-Ala /note=
        "The alanine at position 6 is pyridyl-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 52:

Lys Ser Lys Val Gly Ala Leu Ile Gln Leu Phe His Lys Lys
1               5                   10

(2) INFORMATION FOR SEQ ID NO: 53:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.133"

(ix) FEATURE:
        (A) NAME/KEY: Modified-site
        (B) LOCATION: 6
        (D) OTHER INFORMATION: /label= Substituted-Phe /note=
        "Position 6 is para-amino-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 53:

```
Lys Ser Lys Val Gly Phe Leu Ile Gln Leu Phe His Lys Lys
1               5                   10
```

(2) INFORMATION FOR SEQ ID NO: 54:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.134"

(ix) FEATURE:
        (A) NAME/KEY: Modified-site
        (B) LOCATION: 5
        (D) OTHER INFORMATION: /label= Substituted-Phe /note=
        "Position 5 is para-amino-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 54:

```
Lys Ser Lys Val Phe Trp Leu Ile Gln Leu Phe His Lys Lys
1               5                   10
```

(2) INFORMATION FOR SEQ ID NO: 55:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.135"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 55:

```
Lys Ser Lys Val Gly Lys Leu Ile Gln Leu Phe His Lys Lys
1               5                   10
```

(2) INFORMATION FOR SEQ ID NO: 56:

(i) SEQUENCE CHARACTERISTICS:
        (A) LENGTH: 16 amino acids
        (B) TYPE: amino acid
        (D) TOPOLOGY: circular (ii) MOLECULE TYPE: peptide (ix) FEATURE:
        (A) NAME/KEY: misc_feature
        (D) OTHER INFORMATION: "XMP.137"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 56:

Cys Lys Ser Lys Val Gly Trp Leu Ile Gln Leu Phe His Lys Lys Cys
1               5                   10                  15

(2) INFORMATION FOR SEQ ID NO: 57:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.138"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 57:

Lys Ser Lys Val Lys Phe Leu Ile Gln Leu Phe His Lys Lys
1               5                   10

(2) INFORMATION FOR SEQ ID NO: 58:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.139"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 58:

Lys Ser Lys Val Gly Tyr Leu Ile Gln Leu Phe His Lys Lys
1               5                   10

(2) INFORMATION FOR SEQ ID NO: 59:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.142"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 59:

Lys Ser Lys Val Gly Trp Leu Ile Gln Trp Phe His Lys Lys
1               5                   10

-continued (2) INFORMATION FOR SEQ ID NO: 60:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.143"

(ix) FEATURE:
        (A) NAME/KEY: Modified-site
        (B) LOCATION: 10
        (D) OTHER INFORMATION: /label= Substituted-Ala /note=
        "Position 10 is beta-1-naphthyl-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 60:

Lys Ser Lys Val Gly Trp Leu Ile Gln Ala Phe His Lys Lys
1               5                   10

(2) INFORMATION FOR SEQ ID NO: 61:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.144"

(ix) FEATURE:
        (A) NAME/KEY: Modified-site
        (B) LOCATION: 6
        (D) OTHER INFORMATION: /label= Substituted-Ala /note=
        "The alanine at position 6 is cyclohexyl-substituted."

(ix) FEATURE:
        (A) NAME/KEY: Modified-site
        (B) LOCATION: C-Terminus
        (D) OTHER INFORMATION: /label= Amidat  /note=
        "The C-Terminus is Amidated."

(xi) SEQUENCE DESCRIPTION: SEQ ID NO: 61:

Lys Ser Lys Val Gly Ala Leu Ile Gln Leu Phe His Lys Lys
1               5                   10

(2) INFORMATION FOR SEQ ID NO: 62:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.146"

(ix) FEATURE:
        (A) NAME/KEY: Modified-site

```
        (B) LOCATION: 12
        (D) OTHER INFORMATION: /label= Substituted-Ala /note=
            "Position 12 is beta-1-naphthyl-substituted."

(ix) FEATURE:
        (A) NAME/KEY: Modified-site
        (B) LOCATION: 14
        (D) OTHER INFORMATION: /label= Substituted-Ala /note=
            "Position 14 is beta-1-naphthyl-substituted."

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 62:

Lys Ser Lys Val Gly Trp Leu Ile Gln Leu Phe Ala Lys Ala
1               5                   10

(2) INFORMATION FOR SEQ ID NO: 63:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.148"

(ix) FEATURE:
        (A) NAME/KEY: Modified-site
        (B) LOCATION: 6
        (D) OTHER INFORMATION: /label= Substituted-Ala /note=
            "Position 6 is beta-1-naphthyl-substituted."

(ix) FEATURE:
        (A) NAME/KEY: Modified-site
        (B) LOCATION: 12
        (D) OTHER INFORMATION: /label= Substituted-Ala /note=
            "Position 12 is beta-1-naphthyl-substituted."

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 63:

Lys Ser Lys Val Gly Ala Leu Ile Gln Leu Phe Ala Lys Lys
1               5                   10

(2) INFORMATION FOR SEQ ID NO: 64:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.161"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 64:
```

```
Lys Ser Lys Val Lys Ala Leu Ile Gln Leu Phe His Lys Lys
1               5                   10
```

(2) INFORMATION FOR SEQ ID NO: 65:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.166"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 65:

```
Lys Ser Lys Val Gly Val Leu Ile Gln Leu Phe His Lys Lys
1               5                   10
```

(2) INFORMATION FOR SEQ ID NO: 66:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.222"

(ix) FEATURE:
        (A) NAME/KEY: Modified-site
        (B) LOCATION: 6 & 14
        (D) OTHER INFORMATION: /label= Substituted-Ala /note=
        "Positions 6 and 14 are beta-1-naphthyl- substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 66:

```
Lys Ser Lys Val Gly Ala Leu Ile Gln Leu Phe His Lys Ala
1               5                   10
```

(2) INFORMATION FOR SEQ ID NO: 67:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.223"

(ix) FEATURE:
        (A) NAME/KEY: Modified-site
        (B) LOCATION: 6 & 10
        (D) OTHER INFORMATION: /label= Substituted-Ala /note=
        "Positions 6 & 10 are beta-1-naphthyl-substituted."

```
    (ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 67:

Lys Ser Lys Val Gly Ala Leu Ile Gln Ala Phe His Lys Lys
1               5                  10

(2) INFORMATION FOR SEQ ID NO: 68:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.224"

(ix) FEATURE:
         (A) NAME/KEY: Modified-site
         (B) LOCATION: 6
         (D) OTHER INFORMATION: /label= Substituted-Ala /note=
             "Position 6 is beta-1-naphthyl-substituted."

(ix) FEATURE:
         (A) NAME/KEY: Modified-site
         (B) LOCATION: 9
         (D) OTHER INFORMATION: /label= Substituted-Phe /note=
             "Position 9 is para-amino-substituted."

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 68:

Lys Ser Lys Val Gly Ala Leu Ile Phe Leu Phe His Lys Lys
1               5                  10

(2) INFORMATION FOR SEQ ID NO: 69:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.225"

(ix) FEATURE:
         (A) NAME/KEY: Modified-site
         (B) LOCATION: 6
         (D) OTHER INFORMATION: /label= Substituted-Ala /note=
             "Position 6 is beta-1-naphthyl-substituted."

(ix) FEATURE:
         (A) NAME/KEY: Modified-site
         (B) LOCATION: 5
         (D) OTHER INFORMATION: /label= Substituted-Phe /note=
             "Position 5 is para-amino-substituted."

(ix) FEATURE:
         (A) NAME/KEY: Modified-site
         (B) LOCATION: C-Terminus
         (D) OTHER INFORMATION: /label= Amidation /note=
```

"The C-Terminus is Amidated."

(xi) SEQUENCE DESCRIPTION: SEQ ID NO: 69:

```
Lys Ser Lys Val Phe Ala Leu Ile Gln Leu Phe His Lys Lys
1               5                   10
```

(2) INFORMATION FOR SEQ ID NO: 70:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.226"

(ix) FEATURE:
        (A) NAME/KEY: Modified-site
        (B) LOCATION: 6
        (D) OTHER INFORMATION: /label= Substituted-Ala /note=
        "Position 6 is beta-1-naphthyl-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 70:

```
Lys Ser Lys Val Gly Ala Leu Ile Gln Leu Trp His Lys Lys
1               5                   10
```

(2) INFORMATION FOR SEQ ID NO: 71:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.227"

(ix) FEATURE:
        (A) NAME/KEY: Modified-site
        (B) LOCATION: 10 & 14
        (D) OTHER INFORMATION: /label= Substituted-Ala /note=
        "Positions 10 & 14 are beta-1-naphthyl-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 71:

```
Lys Ser Lys Val Gly Trp Leu Ile Gln Ala Phe His Lys Ala
1               5                   10
```

(2) INFORMATION FOR SEQ ID NO: 72:

(i) SEQUENCE CHARACTERISTICS:
        (A) LENGTH: 14 amino acids
        (B) TYPE: amino acid
        (D) TOPOLOGY: linear (ii) MOLECULE TYPE: peptide

```
    (ix) FEATURE:
         (A) NAME/KEY: misc_feature
         (D) OTHER INFORMATION: "XMP.228"

(ix) FEATURE:
         (A) NAME/KEY: Modified-site
         (B) LOCATION: 9
         (D) OTHER INFORMATION: /label= Substituted-Phe /note=
             "Position 9 is para-amino-substituted."

(ix) FEATURE:
         (A) NAME/KEY: Modified-site
         (B) LOCATION: 14
         (D) OTHER INFORMATION: /label= Substituted-Ala /note=
             "Position 14 is beta-1-naphthyl-substituted."

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 72:

Lys Ser Lys Val Gly Trp Leu Ile Phe Leu Phe His Lys Ala
1               5                   10

(2) INFORMATION FOR SEQ ID NO: 73:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.229"

(ix) FEATURE:
         (A) NAME/KEY: Modified-site
         (B) LOCATION: 5
         (D) OTHER INFORMATION: /label= Substituted-Ala /note=
             "Position 5 is para-amino-substituted."

(ix) FEATURE:
         (A) NAME/KEY: Modified-site
         (B) LOCATION: 14
         (D) OTHER INFORMATION: /label= Substituted-Ala /note=
             "Position 14 is beta-1-naphthyl-substituted."

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 73:

Lys Ser Lys Val Phe Trp Leu Ile Gln Leu Phe His Lys Ala
1               5                   10

(2) INFORMATION FOR SEQ ID NO: 74:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.230"

(ix) FEATURE:
```

```
        (A) NAME/KEY: Modified-site
        (B) LOCATION: 14
        (D) OTHER INFORMATION: /label= Substituted-Ala /note=
            "Position 14 is beta-1-naphthyl-substituted."

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 74:

Lys Ser Lys Val Gly Trp Leu Ile Gln Leu Trp His Lys Ala
1               5                   10

(2) INFORMATION FOR SEQ ID NO: 75:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.231"

(ix) FEATURE:
        (A) NAME/KEY: Modified-site
        (B) LOCATION: 10 & 12
        (D) OTHER INFORMATION: /label= Substituted-Ala /note=
            "Positions 10 & 12 are beta-1-naphthyl-substituted."

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 75:

Lys Ser Lys Val Gly Trp Leu Ile Gln Ala Phe Ala Lys Lys
1               5                   10

(2) INFORMATION FOR SEQ ID NO: 76:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.232"

(ix) FEATURE:
        (A) NAME/KEY: Modified-site
        (B) LOCATION: 9
        (D) OTHER INFORMATION: /label= Substituted-Phe /note=
            "Position 9 is para-amino-substituted."

(ix) FEATURE:
        (A) NAME/KEY: Modified-site
        (B) LOCATION: 12
        (D) OTHER INFORMATION: /label= Substituted-Ala /note=
            "Position 12 is beta-1-naphthyl-substituted."

(ix) FEATURE:
        (A) NAME/KEY: Modified-site
        (B) LOCATION: C-Terminus
        (D) OTHER INFORMATION: /label= Amidation /note=
            "The C-Terminus is Amidated."
```

(xi) SEQUENCE DESCRIPTION: SEQ ID NO: 76:

Lys Ser Lys Val Gly Trp Leu Ile Phe Leu Phe Ala Lys Lys
1               5                   10

(2) INFORMATION FOR SEQ ID NO: 77:

(i) SEQUENCE CHARACTERISTICS:
           (A) LENGTH: 14 amino acids
           (B) TYPE: amino acid
           (D) TOPOLOGY: linear (ii) MOLECULE TYPE: peptide (ix) FEATURE:
           (A) NAME/KEY: misc_feature
           (D) OTHER INFORMATION: "XMP.233"

(ix) FEATURE:
           (A) NAME/KEY: Modified-site
           (B) LOCATION: 5
           (D) OTHER INFORMATION: /label= Substituted-Phe /note=
               "Position 5 is para-amino-substituted."

(ix) FEATURE:
           (A) NAME/KEY: Modified-site
           (B) LOCATION: 12
           (D) OTHER INFORMATION: /label= Substituted-Ala /note=
               "Position 12 is beta-1-naphthyl-substituted."

(ix) FEATURE:
           (A) NAME/KEY: Modified-site
           (B) LOCATION: C-Terminus
           (D) OTHER INFORMATION: /label= Amidation /note=
               "The C-Terminus is Amidated."

(xi) SEQUENCE DESCRIPTION: SEQ ID NO: 77:

Lys Ser Lys Val Phe Trp Leu Ile Gln Leu Phe Ala Lys Lys
1               5                   10

(2) INFORMATION FOR SEQ ID NO: 78:

(i) SEQUENCE CHARACTERISTICS:
           (A) LENGTH: 14 amino acids
           (B) TYPE: amino acid
           (D) TOPOLOGY: linear (ii) MOLECULE TYPE: peptide (ix) FEATURE:
           (A) NAME/KEY: misc_feature
           (D) OTHER INFORMATION: "XMP.234"

(ix) FEATURE:
           (A) NAME/KEY: Modified-site
           (B) LOCATION: 12
           (D) OTHER INFORMATION: /label= Substituted-Ala /note=
               "Position 12 is beta-1-naphthyl-substituted."

(ix) FEATURE:
           (A) NAME/KEY: Modified-site
           (B) LOCATION: C-Terminus
           (D) OTHER INFORMATION: /label= Amidation /note=
               "The C-Terminus is Amidated."

(xi) SEQUENCE DESCRIPTION: SEQ ID NO: 78:

Lys Ser Lys Val Gly Trp Leu Ile Gln Leu Trp Ala Lys Lys
1               5                   10

(2) INFORMATION FOR SEQ ID NO: 79:

(i) SEQUENCE CHARACTERISTICS:
           (A) LENGTH: 14 amino acids
           (B) TYPE: amino acid

```
            (D) TOPOLOGY: linear (ii) MOLECULE TYPE: peptide (ix) FEATURE:
         (A) NAME/KEY: misc_feature
         (D) OTHER INFORMATION: "XMP.235"

(ix) FEATURE:
         (A) NAME/KEY: Modified-site
         (B) LOCATION: 9
         (D) OTHER INFORMATION: /label= Substituted-Phe /note=
             "Position 9 is para-amino-substituted."

(ix) FEATURE:
         (A) NAME/KEY: Modified-site
         (B) LOCATION: 10
         (D) OTHER INFORMATION: /label= Substituted-Ala /note=
             "Position 10 is beta-1-naphthyl-substituted."

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 79:

Lys Ser Lys Val Gly Trp Leu Ile Phe Ala Phe His Lys Lys
1               5                   10

(2) INFORMATION FOR SEQ ID NO: 80:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.236"

(ix) FEATURE:
         (A) NAME/KEY: Modified-site
         (B) LOCATION: 5
         (D) OTHER INFORMATION: /label= Substituted-Phe /note=
             "Position 5 is para-amino-substituted."

(ix) FEATURE:
         (A) NAME/KEY: Modified-site
         (B) LOCATION: 10
         (D) OTHER INFORMATION: /label= Substituted-Ala /note=
             "Position 10 is beta-1-naphthyl-substituted."

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 80:

Lys Ser Lys Val Phe Trp Leu Ile Gln Ala Phe His Lys Lys
1               5                   10

(2) INFORMATION FOR SEQ ID NO: 81:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
```

```
        (A) NAME/KEY: misc_feature
        (D) OTHER INFORMATION: "XMP.237"

(ix) FEATURE:
        (A) NAME/KEY: Modified-site
        (B) LOCATION: 10
        (D) OTHER INFORMATION: /label= Substituted-Ala /note=
        "Position 10 is beta-1-naphthyl-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 81:

Lys Ser Lys Val Gly Trp Leu Ile Gln Ala Trp His Lys Lys
1               5                   10

(2) INFORMATION FOR SEQ ID NO: 82:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.238"

(ix) FEATURE:
        (A) NAME/KEY: Modified-site
        (B) LOCATION: 5
        (D) OTHER INFORMATION: /label= Substituted-Phe /note=
        "Position 5 is para-amino-substituted."

(ix) FEATURE:
        (A) NAME/KEY: Modified-site
        (B) LOCATION: 9
        (D) OTHER INFORMATION: /label= Substituted-Phe /note=
        "Position 9 is para-amino-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 82:

Lys Ser Lys Val Phe Trp Leu Ile Phe Leu Phe His Lys Lys
1               5                   10

(2) INFORMATION FOR SEQ ID NO: 83:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.239"

(ix) FEATURE:
        (A) NAME/KEY: Modified-site
        (B) LOCATION: 9
        (D) OTHER INFORMATION: /label= Substituted-Phe /note=
        "Position 9 is para-amino-substituted."

(ix) FEATURE:
        (A) NAME/KEY: Modified-site
```

```
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 83:

Lys Ser Lys Val Gly Trp Leu Ile Phe Leu Trp His Lys Lys
1               5                   10

(2) INFORMATION FOR SEQ ID NO: 84:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.240"

(ix) FEATURE:
        (A) NAME/KEY: Modified-site
        (B) LOCATION: 5
        (D) OTHER INFORMATION: /label= Substituted-Phe /note=
            "Position 5 is para-amino-substituted."

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 84:

Lys Ser Lys Val Phe Trp Leu Ile Gln Leu Trp His Lys Lys
1               5                   10

(2) INFORMATION FOR SEQ ID NO: 85:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.241"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 85:

Lys Ser Lys Val Gly Trp Leu Ile Leu Leu Trp His Lys Lys
1               5                   10

(2) INFORMATION FOR SEQ ID NO: 86:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.242"
```

```
    (ix) FEATURE:
         (A) NAME/KEY: Modified-site
         (B) LOCATION: 6
         (D) OTHER INFORMATION: /label= Substituted-Ala /note=
             "Position 6 is D-beta-2-naphthyl-substituted."

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 86:

Lys Ser Lys Val Gly Ala Leu Ile Leu Leu Phe His Lys Lys
1               5                   10

(2) INFORMATION FOR SEQ ID NO: 87:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.243"

(ix) FEATURE:
         (A) NAME/KEY: Modified-site
         (B) LOCATION: 6
         (D) OTHER INFORMATION: /label= Substituted-Ala /note=
             "Position 6 is D-beta-2-naphthyl-substituted."

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 87:

Lys Ser Lys Val Gly Ala Leu Ile Gln Leu Trp His Lys Lys
1               5                   10

(2) INFORMATION FOR SEQ ID NO: 88:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.244"

(ix) FEATURE:
         (A) NAME/KEY: Modified-site
         (B) LOCATION: 6
         (D) OTHER INFORMATION: /label= Substituted-Ala /note=
             "Position 6 is D-beta-2-naphthyl-substituted."

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 88:

Lys Ser Lys Val Gly Ala Leu Ile Leu Leu Trp His Lys Lys
1               5                   10
```

(2) INFORMATION FOR SEQ ID NO: 89:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.249"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 89:

```
Lys Ser Lys Val Gly Gly Leu Ile Gln Leu Phe His Lys Lys
1               5                   10
```

(2) INFORMATION FOR SEQ ID NO: 90:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.250"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 90:

```
Lys Ser Lys Val Gly Leu Leu Ile Gln Leu Phe His Lys Lys
1               5                   10
```

(2) INFORMATION FOR SEQ ID NO: 91:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.251"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 91:

```
Lys Ser Lys Val Gly Ile Leu Ile Gln Leu Phe His Lys Lys
1               5                   10
```

(2) INFORMATION FOR SEQ ID NO: 92:

(i) SEQUENCE CHARACTERISTICS:

```
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.252"

(ix) FEATURE:
        (A) NAME/KEY: Modified-site
        (B) LOCATION: 6
        (D) OTHER INFORMATION: /label= D-Ala /note=
            "Position 6 is D-alanine"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 92:

Lys Ser Lys Val Gly Ala Leu Ile Gln Leu Phe His Lys Lys
1               5                   10

(2) INFORMATION FOR SEQ ID NO: 93:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.253"

(ix) FEATURE:
        (A) NAME/KEY: Modified-site
        (B) LOCATION: 6
        (D) OTHER INFORMATION: /label= D-Val /note=
            "Position 6 is D-valine"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 93:

Lys Ser Lys Val Gly Val Leu Ile Gln Leu Phe His Lys Lys
1               5                   10

(2) INFORMATION FOR SEQ ID NO: 94:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.254"

(ix) FEATURE:
        (A) NAME/KEY: Modified-site
        (B) LOCATION: 6
        (D) OTHER INFORMATION: /label= beta-Ala /note=
            "Position 6 is beta-alanine"

(ix) FEATURE:
```

(A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 94:

Lys Ser Lys Val Gly Ala Leu Ile Gln Leu Phe His Lys Lys
1               5                   10

(2) INFORMATION FOR SEQ ID NO: 95:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.255"

(ix) FEATURE:
        (A) NAME/KEY: Modified-site
        (B) LOCATION: 6
        (D) OTHER INFORMATION: /label= alpha-aba /note=
        "Position 6 is alpha-aminobutyric acid"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 95:

Lys Ser Lys Val Gly Xaa Leu Ile Gln Leu Phe His Lys Lys
1               5                   10

(2) INFORMATION FOR SEQ ID NO: 96:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.256"

(ix) FEATURE:
        (A) NAME/KEY: Modified-site
        (B) LOCATION: 6
        (D) OTHER INFORMATION: /label= gaba /note=
        "Position 6 is gamma-aminobutyric acid"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 96:

Lys Ser Lys Val Gly Xaa Leu Ile Gln Leu Phe His Lys Lys
1               5                   10

(2) INFORMATION FOR SEQ ID NO: 97:

(i) SEQUENCE CHARACTERISTICS:
        (A) LENGTH: 14 amino acids
        (B) TYPE: amino acid
        (D) TOPOLOGY: linear

```
        (ii) MOLECULE TYPE: peptide (ix) FEATURE:
             (A) NAME/KEY: misc_feature
             (D) OTHER INFORMATION: "XMP.257"

(ix) FEATURE:
             (A) NAME/KEY: Modified-site
             (B) LOCATION: 6
             (D) OTHER INFORMATION: /label= .-methyl-A /note=
             "Position 6 is alpha-Methyl-alanine"

(ix) FEATURE:
             (A) NAME/KEY: Modified-site
             (B) LOCATION: C-Terminus
             (D) OTHER INFORMATION: /label= Amidation /note=
             "The C-Terminus is Amidated."

(xi) SEQUENCE DESCRIPTION: SEQ ID NO: 97:

Lys Ser Lys Val Gly Ala Leu Ile Gln Leu Phe His Lys Lys
1               5                   10

(2) INFORMATION FOR SEQ ID NO: 98:

(i) SEQUENCE CHARACTERISTICS:
             (A) LENGTH: 14 amino acids
             (B) TYPE: amino acid
             (D) TOPOLOGY: linear (ii) MOLECULE TYPE: peptide (ix) FEATURE:
             (A) NAME/KEY: misc_feature
             (D) OTHER INFORMATION: "XMP.258"

(ix) FEATURE:
             (A) NAME/KEY: Modified-site
             (B) LOCATION: 6
             (D) OTHER INFORMATION: /label= t-butyl-G /note=
             "Position 6 is tert-butyl-glycine"

(ix) FEATURE:
             (A) NAME/KEY: Modified-site
             (B) LOCATION: C-Terminus
             (D) OTHER INFORMATION: /label= Amidation /note=
             "The C-Terminus is Amidated."

(xi) SEQUENCE DESCRIPTION: SEQ ID NO: 98:

Lys Ser Lys Val Gly Gly Leu Ile Gln Leu Phe His Lys Lys
1               5                   10

(2) INFORMATION FOR SEQ ID NO: 99:

(i) SEQUENCE CHARACTERISTICS:
             (A) LENGTH: 14 amino acids
             (B) TYPE: amino acid
             (D) TOPOLOGY: linear (ii) MOLECULE TYPE: peptide (ix) FEATURE:
             (A) NAME/KEY: misc_feature
             (D) OTHER INFORMATION: "XMP.259"

(ix) FEATURE:
             (A) NAME/KEY: Modified-site
             (B) LOCATION: 6
             (D) OTHER INFORMATION: /label= N-methyl-G /note=
             "Position 6 is N-Methyl-glycine"

(ix) FEATURE:
             (A) NAME/KEY: Modified-site
             (B) LOCATION: C-Terminus
             (D) OTHER INFORMATION: /label= Amidation /note=
```

"The C-Terminus is Amidated."

(xi) SEQUENCE DESCRIPTION: SEQ ID NO: 99:

Lys Ser Lys Val Gly Gly Leu Ile Gln Leu Phe His Lys Lys
1               5                   10

(2) INFORMATION FOR SEQ ID NO: 100:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.260"

(ix) FEATURE:
        (A) NAME/KEY: Modified-site
        (B) LOCATION: 6
        (D) OTHER INFORMATION: /label= N-methyl-V /note=
        "Position 6 is N-Methyl-valine"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 100:

Lys Ser Lys Val Gly Val Leu Ile Gln Leu Phe His Lys Lys
1               5                   10

(2) INFORMATION FOR SEQ ID NO: 101:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.261"

(ix) FEATURE:
        (A) NAME/KEY: Modified-site
        (B) LOCATION: 6
        (D) OTHER INFORMATION: /label= N-methyl-L /note=
        "Position 6 is N-Methyl-leucine"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 101:

Lys Ser Lys Val Gly Leu Leu Ile Gln Leu Phe His Lys Lys
1               5                   10

(2) INFORMATION FOR SEQ ID NO: 102:

(i) SEQUENCE CHARACTERISTICS:
        (A) LENGTH: 14 amino acids
        (B) TYPE: amino acid
        (D) TOPOLOGY: linear (ii) MOLECULE TYPE: peptide

```
    (ix) FEATURE:
         (A) NAME/KEY: misc_feature
         (D) OTHER INFORMATION: "XMP.262"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 102:

Lys Ser Lys Val Gly Trp Leu Ile Asn Leu Phe His Lys Lys
1               5                   10

(2) INFORMATION FOR SEQ ID NO: 103:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.263"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 103:

Lys Ser Lys Val Gly Trp Leu Ile Glu Leu Phe His Lys Lys
1               5                   10

(2) INFORMATION FOR SEQ ID NO: 104:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.264"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 104:

Lys Ser Lys Val Gly Trp Leu Ile Asp Leu Phe His Lys Lys
1               5                   10

(2) INFORMATION FOR SEQ ID NO: 105:

(i) SEQUENCE CHARACTERISTICS:
         (A) LENGTH: 14 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.265"
```

```
    (ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 105:

Lys Ser Lys Val Gly Trp Leu Ile Arg Leu Phe His Lys Lys
1               5                   10

(2) INFORMATION FOR SEQ ID NO: 106:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.266"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 106:

Lys Ser Lys Val Lys Val Leu Ile Gln Leu Phe His Lys Lys
1               5                   10

(2) INFORMATION FOR SEQ ID NO: 107:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.267"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 107:

Lys Ser Lys Val Lys Trp Ala Ile Gln Leu Phe His Lys Lys
1               5                   10

(2) INFORMATION FOR SEQ ID NO: 108:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.268"

(ix) FEATURE:
         (A) NAME/KEY: Modified-site
         (B) LOCATION: C-Terminus
         (D) OTHER INFORMATION: /label= Amidation /note=
```

"The C-Terminus is Amidated."

(xi) SEQUENCE DESCRIPTION: SEQ ID NO: 108:

Lys Ser Lys Val Gly Val Ala Ile Gln Leu Phe His Lys Lys
1               5                   10

(2) INFORMATION FOR SEQ ID NO: 109:

(i) SEQUENCE CHARACTERISTICS:
       (A) LENGTH: 14 amino acids
       (B) TYPE: amino acid
       (D) TOPOLOGY: linear (ii) MOLECULE TYPE: peptide (ix) FEATURE:
       (A) NAME/KEY: misc_feature
       (D) OTHER INFORMATION: "XMP.269"

(ix) FEATURE:
       (A) NAME/KEY: Modified-site
       (B) LOCATION: C-Terminus
       (D) OTHER INFORMATION: /label= Amidation /note=
       "The C-Terminus is Amidated."

(xi) SEQUENCE DESCRIPTION: SEQ ID NO: 109:

Lys Ser Lys Val Lys Val Ala Ile Gln Leu Phe His Lys Lys
1               5                   10

(2) INFORMATION FOR SEQ ID NO: 110:

(i) SEQUENCE CHARACTERISTICS:
       (A) LENGTH: 28 amino acids
       (B) TYPE: amino acid
       (D) TOPOLOGY: linear (ii) MOLECULE TYPE: peptide (ix) FEATURE:
       (A) NAME/KEY: misc_feature
       (D) OTHER INFORMATION: "XMP.270"

(ix) FEATURE:
       (A) NAME/KEY: Modified-site
       (B) LOCATION: C-Terminus
       (D) OTHER INFORMATION: /label= Amidation /note=
       "The C-Terminus is Amidated."

(xi) SEQUENCE DESCRIPTION: SEQ ID NO: 110:

Lys Ser Lys Val Gly Trp Leu Ile Leu Leu Phe His Lys Lys Ser
1               5                   10                  15

Lys Val Gly Trp Leu Ile Gln Leu Phe His Lys Lys
                    20                  25

(2) INFORMATION FOR SEQ ID NO: 111:

(i) SEQUENCE CHARACTERISTICS:
       (A) LENGTH: 28 amino acids
       (B) TYPE: amino acid
       (D) TOPOLOGY: linear (ii) MOLECULE TYPE: peptide (ix) FEATURE:
       (A) NAME/KEY: misc_feature
       (D) OTHER INFORMATION: "XMP.271"

(ix) FEATURE:
       (A) NAME/KEY: Modified-site
       (B) LOCATION: C-Terminus
       (D) OTHER INFORMATION: /label= Amidation /note=
       "The C-Terminus is Amidated."

(xi) SEQUENCE DESCRIPTION: SEQ ID NO: 111:

Lys Ser Lys Val Gly Trp Leu Ile Gln Leu Phe His Lys Lys Ser
1               5                   10                  15
    Lys Val Gly Trp Leu Ile Leu Leu Phe His Lys Lys
                20                  25

(2) INFORMATION FOR SEQ ID NO: 112:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.272"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 112:

Lys Ser Lys Val Gly Trp Leu Ile Leu Leu Phe His Lys Lys Ser
1               5                   10                  15
    Lys Val Gly Trp Leu Ile Leu Leu Phe His Lys Lys
                20                  25

(2) INFORMATION FOR SEQ ID NO: 113:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.273"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 113:

Lys Ser Lys Val Gly Trp Leu Ile Phe Leu Phe His Lys Lys Ser
1               5                   10                  15
    Lys Val Gly Trp Leu Ile Gln Leu Phe His Lys Lys
                20                  25

(2) INFORMATION FOR SEQ ID NO: 114:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.274"

```
    (ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 114:

Lys Ser Lys Val Gly Trp Leu Ile Gln Leu Phe His Lys Lys Ser
1               5                   10                  15
    Lys Val Gly Trp Leu Ile Phe Leu Phe His Lys Lys
                20                  25

(2) INFORMATION FOR SEQ ID NO: 115:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.275"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 115:

Lys Ser Lys Val Gly Trp Leu Ile Phe Leu Phe His Lys Lys Ser
1               5                   10                  15
    Lys Val Gly Trp Leu Ile Phe Leu Phe His Lys Lys
                20                  25

(2) INFORMATION FOR SEQ ID NO: 116:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.283"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 116:

Lys Ser Lys Val Lys Phe Leu Ile Lys Leu Phe His Lys Lys
1               5                   10

(2) INFORMATION FOR SEQ ID NO: 117:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: misc_feature
```

```
            (D) OTHER INFORMATION: "XMP.284"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 117:

Ser Lys Val Lys Trp Leu Ile Gln Leu Phe His Lys Lys
 1               5                   10

(2) INFORMATION FOR SEQ ID NO: 118:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: misc_feature (ix) FEATURE:
        (A) NAME/KEY: Modified-site
        (B) LOCATION: C-Terminus
        (D) OTHER INFORMATION: /label= Amidation /note=
            "The C-Terminus is Amidated."

(ix) FEATURE:
        (A) NAME/KEY: misc_feature
        (D) OTHER INFORMATION: "XMP.285"

(xi) SEQUENCE DESCRIPTION: SEQ ID NO: 118:

Ser Lys Val Lys Trp Leu Ile Gln Leu Phe His Lys
 1               5                   10

(2) INFORMATION FOR SEQ ID NO: 119:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.286"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 119:

Lys Val Lys Trp Leu Ile Gln Leu Phe His Lys Lys
 1               5                   10

(2) INFORMATION FOR SEQ ID NO: 120:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.287"
```

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 120:

Ser Lys Val Lys Trp Leu Ile Gln Leu Phe His
1               5                   10

(2) INFORMATION FOR SEQ ID NO: 121:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.288"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 121:

Lys Val Lys Trp Leu Ile Gln Leu Phe His Lys
1               5                   10

(2) INFORMATION FOR SEQ ID NO: 122:

(i) SEQUENCE CHARACTERISTICS:
            (A) LENGTH: 11 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.289"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 122:

Val Lys Trp Leu Ile Gln Leu Phe His Lys Lys
1               5                   10

(2) INFORMATION FOR SEQ ID NO: 123:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.290"

(ix) FEATURE:
            (A) NAME/KEY: Modified-site
            (B) LOCATION: C-Terminus

```
         (D) OTHER INFORMATION: /label= Amidation /note=
             "The C-Terminus is Amidated."

(xi) SEQUENCE DESCRIPTION: SEQ ID NO: 123:

Ser Lys Val Lys Trp Leu Ile Gln Leu Phe
1               5                   10

(2) INFORMATION FOR SEQ ID NO: 124:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.291"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 124:

Lys Val Lys Trp Leu Ile Gln Leu Phe His
1               5                   10

(2) INFORMATION FOR SEQ ID NO: 125:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.292"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 125:

Val Lys Trp Leu Ile Gln Leu Phe His Lys
1               5                   10

(2) INFORMATION FOR SEQ ID NO: 126:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.293"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 126:
```

Lys Trp Leu Ile Gln Leu Phe His Lys Lys
1               5                   10

(2) INFORMATION FOR SEQ ID NO: 127:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.294"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 127:

Ser Lys Val Lys Trp Leu Ile Gln Leu
1               5

(2) INFORMATION FOR SEQ ID NO: 128:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.295"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 128:

Lys Val Lys Trp Leu Ile Gln Leu Phe
1               5

(2) INFORMATION FOR SEQ ID NO: 129:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.296"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 129:

Val Lys Trp Leu Ile Gln Leu Phe His
1               5

(2) INFORMATION FOR SEQ ID NO: 130:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.297"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 130:

Lys Trp Leu Ile Gln Leu Phe His Lys
1               5

(2) INFORMATION FOR SEQ ID NO: 131:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.298"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 131:

Trp Leu Ile Gln Leu Phe His Lys Lys
1               5

(2) INFORMATION FOR SEQ ID NO: 132:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.299"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 132:

Ser Lys Val Lys Trp Leu Ile Gln
1               5

(2) INFORMATION FOR SEQ ID NO: 133:

(i) SEQUENCE CHARACTERISTICS:

(A) LENGTH: 8 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.300"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 133:

Lys Val Lys Trp Leu Ile Gln Leu
1               5

(2) INFORMATION FOR SEQ ID NO: 134:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.301"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 134:

Val Lys Trp Leu Ile Gln Leu Phe
1               5

(2) INFORMATION FOR SEQ ID NO: 135:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.302"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 135:

Lys Trp Leu Ile Gln Leu Phe His
1               5

(2) INFORMATION FOR SEQ ID NO: 136:

(i) SEQUENCE CHARACTERISTICS:
        (A) LENGTH: 8 amino acids
        (B) TYPE: amino acid
        (D) TOPOLOGY: linear

```
        (ii) MOLECULE TYPE: peptide (ix) FEATURE:
             (A) NAME/KEY: misc_feature
             (D) OTHER INFORMATION: "XMP.303"

(ix) FEATURE:
             (A) NAME/KEY: Modified-site
             (B) LOCATION: C-Terminus
             (D) OTHER INFORMATION: /label= Amidation /note=
                 "The C-Terminus is Amidated."

(xi) SEQUENCE DESCRIPTION: SEQ ID NO: 136:

Trp Leu Ile Gln Leu Phe His Lys
1               5

(2) INFORMATION FOR SEQ ID NO: 137:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (ix) FEATURE:
             (A) NAME/KEY: misc_feature
             (D) OTHER INFORMATION: "XMP.304"

(ix) FEATURE:
             (A) NAME/KEY: Modified-site
             (B) LOCATION: C-Terminus
             (D) OTHER INFORMATION: /label= Amidation /note=
                 "The C-Terminus is Amidated."

(xi) SEQUENCE DESCRIPTION: SEQ ID NO: 137:

Leu Ile Gln Leu Phe His Lys Lys
1               5

(2) INFORMATION FOR SEQ ID NO: 138:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
             (A) NAME/KEY: misc_feature
             (D) OTHER INFORMATION: "XMP.305"

(ix) FEATURE:
             (A) NAME/KEY: Modified-site
             (B) LOCATION: C-Terminus
             (D) OTHER INFORMATION: /label= Amidation /note=
                 "The C-Terminus is Amidated."

(xi) SEQUENCE DESCRIPTION: SEQ ID NO: 138:

Ser Lys Val Lys Trp Leu Ile
1               5

(2) INFORMATION FOR SEQ ID NO: 139:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
             (A) NAME/KEY: misc_feature
```

(D) OTHER INFORMATION: "XMP.306"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 139:

Lys Val Lys Trp Leu Ile Gln
1               5

(2) INFORMATION FOR SEQ ID NO: 140:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.307"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 140:

Val Lys Trp Leu Ile Gln Leu
1               5

(2) INFORMATION FOR SEQ ID NO: 141:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.308"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 141:

Lys Trp Leu Ile Gln Leu Phe
1               5

(2) INFORMATION FOR SEQ ID NO: 142:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.309"

(ix) FEATURE:
            (A) NAME/KEY: Modified-site (B) LOCATION: C-Terminus
        (D) OTHER INFORMATION: /label= Amidation /note=
            "The C-Terminus is Amidated."

(xi) SEQUENCE DESCRIPTION: SEQ ID NO: 142:

Trp Leu Ile Gln Leu Phe His
1               5

(2) INFORMATION FOR SEQ ID NO: 143:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.310"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 143:

Leu Ile Gln Leu Phe His Lys
1               5

(2) INFORMATION FOR SEQ ID NO: 144:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.311"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 144:

Ile Gln Leu Phe His Lys Lys
1               5

(2) INFORMATION FOR SEQ ID NO: 145:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.312"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 145:

Ser Lys Val Lys Trp Leu
1               5

(2) INFORMATION FOR SEQ ID NO: 146:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.313"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 146:

Lys Val Lys Trp Leu Ile
1               5

(2) INFORMATION FOR SEQ ID NO: 147:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.314"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 147:

Val Lys Trp Leu Ile Gln
1               5

(2) INFORMATION FOR SEQ ID NO: 148:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.315"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 148:

Lys Trp Leu Ile Gln Leu
1               5

(2) INFORMATION FOR SEQ ID NO: 149:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.316"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 149:

Trp Leu Ile Gln Leu Phe
1           5

(2) INFORMATION FOR SEQ ID NO: 150:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.317"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 150:

Leu Ile Gln Leu Phe His
1           5

(2) INFORMATION FOR SEQ ID NO: 151:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.318"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 151:

Ile Gln Leu Phe His Lys
1           5

(2) INFORMATION FOR SEQ ID NO: 152:

```
        (i) SEQUENCE CHARACTERISTICS:
            (A) LENGTH: 6 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.319"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 152:

Gln Leu Phe His Lys Lys
1               5

(2) INFORMATION FOR SEQ ID NO: 153:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.320"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 153:

Trp Leu Ile Gln Leu
1               5

(2) INFORMATION FOR SEQ ID NO: 154:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.321"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 154:

Trp Leu Ile Gln Leu Lys
1               5

(2) INFORMATION FOR SEQ ID NO: 155:

(i) SEQUENCE CHARACTERISTICS:
            (A) LENGTH: 7 amino acids
            (B) TYPE: amino acid
            (D) TOPOLOGY: linear
```

```
    (ii) MOLECULE TYPE: peptide (ix) FEATURE:
         (A) NAME/KEY: misc_feature
         (D) OTHER INFORMATION: "XMP.322"

(ix) FEATURE:
         (A) NAME/KEY: Modified-site
         (B) LOCATION: C-Terminus
         (D) OTHER INFORMATION: /label= Amidation /note=
         "The C-Terminus is Amidated."

(xi) SEQUENCE DESCRIPTION: SEQ ID NO: 155:

Trp Leu Ile Gln Leu Lys Lys
1               5

(2) INFORMATION FOR SEQ ID NO: 156:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.323"

(ix) FEATURE:
         (A) NAME/KEY: Modified-site
         (B) LOCATION: C-Terminus
         (D) OTHER INFORMATION: /label= Amidation /note=
         "The C-Terminus is Amidated."

(xi) SEQUENCE DESCRIPTION: SEQ ID NO: 156:

Lys Trp Leu Ile Gln Leu Lys
1               5

(2) INFORMATION FOR SEQ ID NO: 157:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.324"

(ix) FEATURE:
         (A) NAME/KEY: Modified-site
         (B) LOCATION: C-Terminus
         (D) OTHER INFORMATION: /label= Amidation /note=
         "The C-Terminus is Amidated."

(xi) SEQUENCE DESCRIPTION: SEQ ID NO: 157:

Lys Trp Leu Ile Gln Leu Lys Lys
1               5

(2) INFORMATION FOR SEQ ID NO: 158:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
```

(A) NAME/KEY: misc_feature
            (D) OTHER INFORMATION: "XMP.325"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 158:

Lys Lys Trp Leu Ile Gln Leu
1               5

(2) INFORMATION FOR SEQ ID NO: 159:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.326"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 159:

Lys Lys Trp Leu Ile Gln Leu Lys
1               5

(2) INFORMATION FOR SEQ ID NO: 160:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.327"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 160:

Lys Lys Trp Leu Ile Gln Leu Lys Lys
1               5

(2) INFORMATION FOR SEQ ID NO: 161:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.330"

(ix) FEATURE:

(A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 161:

Trp Leu Ile Gln
1

(2) INFORMATION FOR SEQ ID NO: 162:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.331"

(ix) FEATURE:
        (A) NAME/KEY: Modified-site
        (B) LOCATION: 1
        (D) OTHER INFORMATION: /label= Acetylated /note=
            "Position 1 is acetylated."

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 162:

Lys Lys Trp Leu Ile Gln Leu Lys Lys
1               5

(2) INFORMATION FOR SEQ ID NO: 163:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.332"

(ix) FEATURE:
        (A) NAME/KEY: Modified-site
        (B) LOCATION: 1-9
        (D) OTHER INFORMATION: /label= D-Amino Acids /note=
            "Positions 1-9 are D-amino acids"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 163:

Lys Lys Leu Gln Ile Leu Trp Lys Lys
1               5

(2) INFORMATION FOR SEQ ID NO: 164:

(i) SEQUENCE CHARACTERISTICS:
        (A) LENGTH: 9 amino acids
        (B) TYPE: amino acid
        (D) TOPOLOGY: linear

```
    (ii) MOLECULE TYPE: peptide (ix) FEATURE:
         (A) NAME/KEY: misc_feature
         (D) OTHER INFORMATION: "XMP.333"

(ix) FEATURE:
         (A) NAME/KEY: Modified-site
         (B) LOCATION: 1
         (D) OTHER INFORMATION: /label= D-Lys /note=
         "Position 1 is D-lysine"

(ix) FEATURE:
         (A) NAME/KEY: Modified-site
         (B) LOCATION: C-Terminus
         (D) OTHER INFORMATION: /label= Amidation /note=
         "The C-Terminus is Amidated."

(xi) SEQUENCE DESCRIPTION: SEQ ID NO: 164:

Lys Lys Trp Leu Ile Gln Leu Lys Lys
1               5

(2) INFORMATION FOR SEQ ID NO: 165:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.334"

(ix) FEATURE:
         (A) NAME/KEY: Modified-site
         (B) LOCATION: 1
         (D) OTHER INFORMATION: /label= D-Pro /note=
         "Position 1 is D-proline"

(ix) FEATURE:
         (A) NAME/KEY: Modified-site
         (B) LOCATION: C-Terminus
         (D) OTHER INFORMATION: /label= Amidation /note=
         "The C-Terminus is Amidated."

(xi) SEQUENCE DESCRIPTION: SEQ ID NO: 165:

Pro Lys Trp Leu Ile Gln Leu Lys Lys
1               5

(2) INFORMATION FOR SEQ ID NO: 166:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.335"

(ix) FEATURE:
         (A) NAME/KEY: Modified-site
         (B) LOCATION: C-Terminus
         (D) OTHER INFORMATION: /label= Amidation /note=
         "The C-Terminus is Amidated."

(xi) SEQUENCE DESCRIPTION: SEQ ID NO: 166:

Pro Lys Trp Leu Ile Gln Leu Lys Lys
1               5
```

(2) INFORMATION FOR SEQ ID NO: 167:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.336"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 167:

```
Arg Arg Trp Leu Ile Gln Leu Arg Arg
1               5
```

(2) INFORMATION FOR SEQ ID NO: 168:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.337"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 168:

```
His His Trp Leu Ile Gln Leu His His
1               5
```

(2) INFORMATION FOR SEQ ID NO: 169:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.338"

(ix) FEATURE:
        (A) NAME/KEY: Modified-site
        (B) LOCATION: 1, 2, 8 & 9
        (D) OTHER INFORMATION: /label= Orn /note=
        "Positions 1, 2, 8 & 9 are Ornithine"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 169:

```
Xaa Xaa Trp Leu Ile Gln Leu Xaa Xaa
1               5
```

(2) INFORMATION FOR SEQ ID NO: 170:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.339"

(ix) FEATURE:
        (A) NAME/KEY: Modified-site
        (B) LOCATION: 1, 2, 8 & 9
        (D) OTHER INFORMATION: /label= Dbu /note=
        "Positions 1, 2, 8 & 9 are Diaminobutyric
           acid"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 170:

```
Xaa Xaa Trp Leu Ile Gln Leu Xaa Xaa
1               5
```

(2) INFORMATION FOR SEQ ID NO: 171:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.340"

(ix) FEATURE:
        (A) NAME/KEY: Modified-site
        (B) LOCATION: 1, 2, 8 & 9
        (D) OTHER INFORMATION: /label= Substituted-Phe /note=
        "Positions 1, 2, 8 & 9 are para-amino-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 171:

```
Phe Phe Trp Leu Ile Gln Leu Phe Phe
1               5
```

(2) INFORMATION FOR SEQ ID NO: 172:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.341"

```
        (ix) FEATURE:
              (A) NAME/KEY: Modified-site
              (B) LOCATION: 1, 2, 8 & 9
              (D) OTHER INFORMATION: /label= Substituted-Ala /note=
                  "The alanine at positions 1, 2, 8 & 9 is
                     pyridyl-substituted."

(ix) FEATURE:
              (A) NAME/KEY: Modified-site
              (B) LOCATION: C-Terminus
              (D) OTHER INFORMATION: /label= Amidation /note=
                  "The C-Terminus is Amidated."

(xi) SEQUENCE DESCRIPTION: SEQ ID NO: 172:

Ala Ala Trp Leu Ile Gln Leu Ala Ala
1               5

(2) INFORMATION FOR SEQ ID NO: 173:

(i) SEQUENCE CHARACTERISTICS:
              (A) LENGTH: 9 amino acids
              (B) TYPE: amino acid
              (D) TOPOLOGY: linear (ii) MOLECULE TYPE: peptide (ix) FEATURE:
              (A) NAME/KEY: misc_feature
              (D) OTHER INFORMATION: "XMP.342"

(ix) FEATURE:
              (A) NAME/KEY: Modified-site
              (B) LOCATION: 1, 2, 8 & 9
              (D) OTHER INFORMATION: /label= D-Lys /note=
                  "Positions 1, 2, 8 & 9 are D-lysine"

(ix) FEATURE:
              (A) NAME/KEY: Modified-site
              (B) LOCATION: C-Terminus
              (D) OTHER INFORMATION: /label= Amidation /note=
                  "The C-Terminus is Amidated."

(xi) SEQUENCE DESCRIPTION: SEQ ID NO: 173:

Lys Lys Trp Leu Ile Gln Leu Lys Lys
1               5

(2) INFORMATION FOR SEQ ID NO: 174:

(i) SEQUENCE CHARACTERISTICS:
              (A) LENGTH: 9 amino acids
              (B) TYPE: amino acid
              (D) TOPOLOGY: linear (ii) MOLECULE TYPE: peptide (ix) FEATURE:
              (A) NAME/KEY: misc_feature
              (D) OTHER INFORMATION: "XMP.343"

(ix) FEATURE:
              (A) NAME/KEY: Modified-site
              (B) LOCATION: C-Terminus
              (D) OTHER INFORMATION: /label= Amidation /note=
                  "The C-Terminus is Amidated."

(xi) SEQUENCE DESCRIPTION: SEQ ID NO: 174:

Lys Lys Val Leu Ile Gln Leu Lys Lys
1               5

(2) INFORMATION FOR SEQ ID NO: 175:

(i) SEQUENCE CHARACTERISTICS:
```

(A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.344"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 175:

Lys Lys Trp Ala Ile Gln Leu Lys Lys
1               5

(2) INFORMATION FOR SEQ ID NO: 176:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.345"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 176:

Lys Lys Trp Leu Ile Gln Ala Lys Lys
1               5

(2) INFORMATION FOR SEQ ID NO: 177:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.346"

(ix) FEATURE:
        (A) NAME/KEY: Modified-site
        (B) LOCATION: 3
        (D) OTHER INFORMATION: /label= Substituted-Phe /note=
        "The phenylalanine at position 3 is p-amino-substituted."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 177:

Lys Lys Phe Leu Ile Gln Leu Lys Lys
1               5

(2) INFORMATION FOR SEQ ID NO: 178:

```
        (i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.347"

(ix) FEATURE:
            (A) NAME/KEY: Modified-site
            (B) LOCATION: 3
            (D) OTHER INFORMATION: /label= Substituted-Ala /note=
            "Position 3 is D-beta-2-naphthyl-substituted."

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 178:

Lys Lys Ala Leu Ile Leu Leu Lys Lys
1               5

(2) INFORMATION FOR SEQ ID NO: 179:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.348"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 179:

Lys Lys Lys Trp Leu Ile Gln Leu Lys Lys
1               5                   10

(2) INFORMATION FOR SEQ ID NO: 180:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.349"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 180:

Lys Lys Trp Leu Ile Gln Leu Lys Lys Lys
1               5                   10
```

(2) INFORMATION FOR SEQ ID NO: 181:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.350"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 181:

Lys Lys Lys Trp Leu Ile Gln Leu Lys Lys Lys
1               5                   10

(2) INFORMATION FOR SEQ ID NO: 182:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.351"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 182:

Lys Lys Trp Leu Ile Gln Leu Phe Lys Lys
1               5                   10

(2) INFORMATION FOR SEQ ID NO: 183:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.352"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 183:

Lys Lys Trp Leu Ile Gln Leu Phe His Lys Lys
1               5                   10

(2) INFORMATION FOR SEQ ID NO: 184:

(i) SEQUENCE CHARACTERISTICS:

(A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.353"

(xi) SEQUENCE DESCRIPTION: SEQ ID NO: 184:

Pro Trp Leu Ile Gln Leu Phe His Lys Lys
1               5                   10

(2) INFORMATION FOR SEQ ID NO: 185:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.354"

(ix) FEATURE:
        (A) NAME/KEY: Modified-site
        (B) LOCATION: 1
        (D) OTHER INFORMATION: /label= Acetylated /note=
        "Position 1 is acetylated."

(xi) SEQUENCE DESCRIPTION: SEQ ID NO: 185:

Pro Trp Leu Ile Gln Leu Phe His Lys Lys
1               5                   10

(2) INFORMATION FOR SEQ ID NO: 186:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.355"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 186:

Pro Trp Leu Ile Gln Leu Phe His Lys Lys
1               5                   10

(2) INFORMATION FOR SEQ ID NO: 187:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.356"

```
    (ix) FEATURE:
         (A) NAME/KEY: Modified-site
         (B) LOCATION: 1
         (D) OTHER INFORMATION: /label= Acetylated /note=
             "Position 1 is acetylated."

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 187:

Pro Trp Leu Ile Gln Leu Phe His Lys Lys
1               5                   10

(2) INFORMATION FOR SEQ ID NO: 188:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.357"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 188:

Lys Trp Leu Ile Gln Leu Phe His Lys Pro
1               5                   10

(2) INFORMATION FOR SEQ ID NO: 189:

(i) SEQUENCE CHARACTERISTICS:
         (A) LENGTH: 11 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.358"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 189:

Lys Lys Trp Leu Ile Gln Leu Phe His Lys Pro
1               5                   10

(2) INFORMATION FOR SEQ ID NO: 190:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (ix) FEATURE:
         (A) NAME/KEY: misc_feature
```

(D) OTHER INFORMATION: "XMP.359"

(ix) FEATURE:
        (A) NAME/KEY: Modified-site
        (B) LOCATION: 1
        (D) OTHER INFORMATION: /label= D-Cys /note=
            "Position 1 is D-cysteine."

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 190:

Cys Trp Leu Ile Gln Leu Phe His Lys Lys
1               5                   10

(2) INFORMATION FOR SEQ ID NO: 191:

(i) SEQUENCE CHARACTERISTICS:
        (A) LENGTH: 9 amino acids
        (B) TYPE: amino acid
        (D) TOPOLOGY: circular (ii) MOLECULE TYPE: peptide (ix) FEATURE:
        (A) NAME/KEY: misc_feature
        (D) OTHER INFORMATION: "XMP.360"

(ix) FEATURE:
        (A) NAME/KEY: Modified-site
        (B) LOCATION: 1 & 9
        (D) OTHER INFORMATION: /label= D-Lys /note=
            "Positions 1 & 9 are D-lysine."

(ix) FEATURE:
        (A) NAME/KEY: Modified-site
        (B) LOCATION: 2
        (D) OTHER INFORMATION: /label= D-Cys /note=
            "Position 2 is D-cysteine."

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 191:

Lys Cys Leu Ile Gln Leu Phe Cys Lys
1               5

(2) INFORMATION FOR SEQ ID NO: 192:

(i) SEQUENCE CHARACTERISTICS:
        (A) LENGTH: 9 amino acids
        (B) TYPE: amino acid
        (D) TOPOLOGY: circular (ii) MOLECULE TYPE: peptide (ix) FEATURE:
        (A) NAME/KEY: misc_feature
        (D) OTHER INFORMATION: "XMP.361"

(ix) FEATURE:
        (A) NAME/KEY: Modified-site
        (B) LOCATION: 1 & 9
        (D) OTHER INFORMATION: /label= D-Lys /note=
            "Positions 1 & 9 are D-lysine."

(ix) FEATURE:
        (A) NAME/KEY: Modified-site
        (B) LOCATION: C-Terminus (D) OTHER INFORMATION: /label= Amidation /note=
                    "The C-Terminus is Amidated."

(xi) SEQUENCE DESCRIPTION: SEQ ID NO: 192:

Lys Cys Leu Ile Gln Leu Phe Cys Lys
1               5

(2) INFORMATION FOR SEQ ID NO: 193:

(i) SEQUENCE CHARACTERISTICS:
            (A) LENGTH: 11 amino acids
            (B) TYPE: amino acid
            (D) TOPOLOGY: circular (ii) MOLECULE TYPE: peptide (ix) FEATURE:
            (A) NAME/KEY: misc_feature
            (D) OTHER INFORMATION: "XMP.362"

(ix) FEATURE:
            (A) NAME/KEY: Modified-site
            (B) LOCATION: 1 & 11
            (D) OTHER INFORMATION: /label= D-Lys /note=
                "Positions 1 & 11 are D-lysine."

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 193:

Lys Lys Cys Leu Ile Gln Leu Phe Cys Lys Lys
1               5                   10

(2) INFORMATION FOR SEQ ID NO: 194:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.363"

(ix) FEATURE:
            (A) NAME/KEY: Modified-site
            (B) LOCATION: 1, 9 & 10
            (D) OTHER INFORMATION: /label= D-Lys /note=
                "Positions 1, 9 & 10 are D-lysine."

(ix) FEATURE:
            (A) NAME/KEY: Modified-site
            (B) LOCATION: 2
            (D) OTHER INFORMATION: /label= D-Trp /note=
                "Position 2 is D-tryptophan."

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 194:

Lys Trp Leu Ile Gln Leu Phe His Lys Lys
1               5                   10

(2) INFORMATION FOR SEQ ID NO: 195:

```
        (i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.364"

(ix) FEATURE:
            (A) NAME/KEY: Modified-site
            (B) LOCATION: 1
            (D) OTHER INFORMATION: /label= Acetylated /note=
                "Position 1 is acetylated."

(ix) FEATURE:
            (A) NAME/KEY: Modified-site
            (B) LOCATION: 1, 9 & 10
            (D) OTHER INFORMATION: /label= D-Lys /note=
                "Positions 1, 9 & 10 are D-lysine."

(ix) FEATURE:
            (A) NAME/KEY: Modified-site
            (B) LOCATION: 2
            (D) OTHER INFORMATION: /label= D-Trp /note=
                "Position 2 is D-tryptophan."

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 195:

Lys Trp Leu Ile Gln Leu Phe His Lys Lys
1               5                   10

(2) INFORMATION FOR SEQ ID NO: 196:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.365"

(ix) FEATURE:
            (A) NAME/KEY: Modified-site
            (B) LOCATION: 1-10
            (D) OTHER INFORMATION: /label= D-Amino Acids /note=
                "Positions 1-10 are D-amino acids"

(ix) FEATURE:
            (A) NAME/KEY: Modified-site
            (B) LOCATION: C-Terminus
            (D) OTHER INFORMATION: /label= Amidation /note=
                "The C-Terminus is Amidated."

(xi) SEQUENCE DESCRIPTION: SEQ ID NO: 196:

Lys Trp Leu Ile Gln Leu Phe His Lys Lys
1               5                   10

(2) INFORMATION FOR SEQ ID NO: 197:

(i) SEQUENCE CHARACTERISTICS:
            (A) LENGTH: 10 amino acids
            (B) TYPE: amino acid
            (D) TOPOLOGY: linear
```

```
    (ii) MOLECULE TYPE: peptide (ix) FEATURE:
         (A) NAME/KEY: misc_feature
         (D) OTHER INFORMATION: "XMP.366"

(ix) FEATURE:
         (A) NAME/KEY: Modified-site
         (B) LOCATION: 1
         (D) OTHER INFORMATION: /label= Acetylated /note=
             "Position 1 is acetylated."

(ix) FEATURE:
         (A) NAME/KEY: Modified-site
         (B) LOCATION: 1-10
         (D) OTHER INFORMATION: /label= D-Amino Acids /note=
             "Positions 1-10 are D-amino acids"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 197:

Lys Trp Leu Ile Gln Leu Phe His Lys Lys
1               5                   10

(2) INFORMATION FOR SEQ ID NO: 198:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.367"

(ix) FEATURE:
         (A) NAME/KEY: Modified-site
         (B) LOCATION: 1-10
         (D) OTHER INFORMATION: /label= D-Amino Acids /note=
             "Positions 1-10 are D-amino acids"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 198:

Lys Lys His Phe Leu Gln Ile Leu Trp Lys
1               5                   10

(2) INFORMATION FOR SEQ ID NO: 199:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.368"

(ix) FEATURE:
         (A) NAME/KEY: Modified-site
         (B) LOCATION: 1
         (D) OTHER INFORMATION: /label= Acetylated /note=
             "Position 1 is acetylated."
```

```
    (ix) FEATURE:
         (A) NAME/KEY: Modified-site
         (B) LOCATION: 1-10
         (D) OTHER INFORMATION: /label= D-Amino Acids /note=
             "Positions 1-10 are D-amino acids"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 199:

Lys Lys His Phe Leu Gln Ile Leu Trp Lys
1               5                   10

(2) INFORMATION FOR SEQ ID NO: 200:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.369"

(ix) FEATURE:
         (A) NAME/KEY: Modified-site
         (B) LOCATION: 5
         (D) OTHER INFORMATION: /label= Orn /note=
             "Position 5 is Ornithine"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 200:

Lys Trp Leu Ile Xaa Leu Phe His Lys Lys
1               5                   10

(2) INFORMATION FOR SEQ ID NO: 201:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.370"

(ix) FEATURE:
         (A) NAME/KEY: Modified-site
         (B) LOCATION: 5
         (D) OTHER INFORMATION: /label= Orn /note=
             "Position 5 is Ornithine"

(ix) FEATURE:
         (A) NAME/KEY: Modified-site
         (B) LOCATION: 1
         (D) OTHER INFORMATION: /label= Acetylated /note=
             "Position 1 is acetylated."

(ix) FEATURE:
         (A) NAME/KEY: Modified-site
         (B) LOCATION: C-Terminus
         (D) OTHER INFORMATION: /label= Amidation /note=
```

"The C-Terminus is Amidated."

(xi) SEQUENCE DESCRIPTION: SEQ ID NO: 201:

Lys Trp Leu Ile Xaa Leu Phe His Lys Lys
1               5                   10

(2) INFORMATION FOR SEQ ID NO: 202:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.371"

(ix) FEATURE:
        (A) NAME/KEY: Modified-site
        (B) LOCATION: 5
        (D) OTHER INFORMATION: /label= Dbu /note=
        "Position 5 is Diaminobutyric acid"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 202:

Lys Trp Leu Ile Xaa Leu Phe His Lys Lys
1               5                   10

(2) INFORMATION FOR SEQ ID NO: 203:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.372"

(ix) FEATURE:
        (A) NAME/KEY: Modified-site
        (B) LOCATION: 5
        (D) OTHER INFORMATION: /label= Dbu /note=
        "Position 5 is Diaminobutyric acid"

(ix) FEATURE:
        (A) NAME/KEY: Modified-site
        (B) LOCATION: 1
        (D) OTHER INFORMATION: /label= Acetylated /note=
        "Position 1 is acetylated."

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 203:

Lys Trp Leu Ile Xaa Leu Phe His Lys Lys
1               5                   10

(2) INFORMATION FOR SEQ ID NO: 204:

(i) SEQUENCE CHARACTERISTICS:

```
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.373"

(ix) FEATURE:
        (A) NAME/KEY: Modified-site
        (B) LOCATION: 1
        (D) OTHER INFORMATION: /label= Acetylated /note=
            "Position 1 is acetylated."

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(xi) SEQUENCE DESCRIPTION: SEQ ID NO: 204:

Lys Trp Leu Ile Gln Leu Phe His Lys Lys
1               5                   10

(2) INFORMATION FOR SEQ ID NO: 205:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.374"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(ix) FEATURE:
        (A) NAME/KEY: Modified-site
        (B) LOCATION: 1-8
        (D) OTHER INFORMATION: /label= D-Amino Acids /note=
            "Positions 1-8 are D-Amino Acids."

(xi) SEQUENCE DESCRIPTION: SEQ ID NO: 205:

Lys Leu Gln Ile Leu Trp Lys Lys
1               5

(2) INFORMATION FOR SEQ ID NO: 206:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.375"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(ix) FEATURE:
```

```
            (A) NAME/KEY: Modified-site
            (B) LOCATION: 1-9
            (D) OTHER INFORMATION: /label= D-Amino Acids /note=
                "Positions 1-9 are D-Amino Acids."

(xi) SEQUENCE DESCRIPTION: SEQ ID NO: 206:

Lys Lys Trp Ala Ile Gln Leu Lys Lys
1               5

(2) INFORMATION FOR SEQ ID NO: 207:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.376"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(ix) FEATURE:
         (A) NAME/KEY: Modified-site
         (B) LOCATION: 1-9
         (D) OTHER INFORMATION: /label= D-Amino Acids /note=
             "Positions 1-9 are D-Amino Acids."

(xi) SEQUENCE DESCRIPTION: SEQ ID NO: 207:

Lys Lys Leu Gln Ile Ala Trp Lys Lys
1               5

(2) INFORMATION FOR SEQ ID NO: 208:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.377"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 208:

Lys Lys Lys Trp Ala Ile Gln Leu Lys Lys
1               5                   10

(2) INFORMATION FOR SEQ ID NO: 209:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.378"
```

```
    (ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 209:

Pro Trp Ala Ile Gln Leu Lys Lys
1               5

(2) INFORMATION FOR SEQ ID NO: 210:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.379"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 210:

Lys Lys Pro Trp Ala Ile Gln Leu Lys Lys
1               5                   10

(2) INFORMATION FOR SEQ ID NO: 211:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.380"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 211:

Lys Lys Gln Leu Leu Leu Leu Lys Lys
1               5

(2) INFORMATION FOR SEQ ID NO: 212:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.381"

(ix) FEATURE:
         (A) NAME/KEY: Modified-site
         (B) LOCATION: C-Terminus
```

```
            (D) OTHER INFORMATION: /label= Amidation /note=
                "The C-Terminus is Amidated."

(xi) SEQUENCE DESCRIPTION: SEQ ID NO: 212:

Lys Lys Leu Gln Leu Leu Leu Lys Lys
1               5

(2) INFORMATION FOR SEQ ID NO: 213:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.382:

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 213:

Lys Lys Leu Leu Gln Leu Leu Lys Lys
1               5

(2) INFORMATION FOR SEQ ID NO: 214:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.383"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 214:

Lys Lys Leu Leu Leu Gln Leu Lys Lys
1               5

(2) INFORMATION FOR SEQ ID NO: 215:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (ix) FEATURE:
         (A) NAME/KEY: misc_feature
         (D) OTHER INFORMATION: "XMP.384"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(xi) SEQUENCE DESCRIPTION: SEQ ID NO: 215:
```

Lys Lys Leu Leu Leu Leu Gln Lys Lys
1               5

(2) INFORMATION FOR SEQ ID NO: 216:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.385"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 216:

Lys Lys Leu Leu Leu Leu Leu Lys Lys
1               5

(2) INFORMATION FOR SEQ ID NO: 217:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.386"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 217:

Lys Trp Ala Ile Gln Leu Phe His Lys Lys Ile
1               5                   10

(2) INFORMATION FOR SEQ ID NO: 218:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.387"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 218:

Pro Trp Ala Ile Gln Leu Phe His Lys Lys
1               5                   10

-continued (2) INFORMATION FOR SEQ ID NO: 219:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.388"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 219:

Gly Trp Leu Ile Gln Leu Phe His Lys Lys
1               5                   10

(2) INFORMATION FOR SEQ ID NO: 220:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.389"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 220:

Lys Gly Trp Leu Ile Gln Leu Phe His Lys Lys
1               5                   10

(2) INFORMATION FOR SEQ ID NO: 221:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.390"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 221:

Lys Pro Trp Leu Ile Gln Leu Phe His Lys Lys
1               5                   10

(2) INFORMATION FOR SEQ ID NO: 222:

(i) SEQUENCE CHARACTERISTICS:

(A) LENGTH: 12 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.391"

(ix) FEATURE:
(A) NAME/KEY: Modified-site
(B) LOCATION: C-Terminus
(D) OTHER INFORMATION: /label= Amidation /note=
"The C-Terminus is Amidated."

(xi) SEQUENCE DESCRIPTION: SEQ ID NO: 222:

Lys Val Gly Trp Leu Ile Gln Leu Phe His Lys Lys
1               5                   10

(2) INFORMATION FOR SEQ ID NO: 223:

(i) SEQUENCE CHARACTERISTICS:
(A) LENGTH: 12 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.392"

(ix) FEATURE:
(A) NAME/KEY: Modified-site
(B) LOCATION: C-Terminus
(D) OTHER INFORMATION: /label= Amidation /note=
"The C-Terminus is Amidated."

(xi) SEQUENCE DESCRIPTION: SEQ ID NO: 223:

Lys Val Pro Trp Leu Ile Gln Leu Phe His Lys Lys
1               5                   10

(2) INFORMATION FOR SEQ ID NO: 224:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: misc_feature
(D) OTHER INFORMATION: "XMP.393"

(ix) FEATURE:
(A) NAME/KEY: Modified-site
(B) LOCATION: C-Terminus
(D) OTHER INFORMATION: /label= Amidation /note=
"The C-Terminus is Amidated."

(xi) SEQUENCE DESCRIPTION: SEQ ID NO: 224:

Lys Ser Lys Val Pro Trp Leu Ile Gln Leu Phe His Lys Lys
1               5                   10

(2) INFORMATION FOR SEQ ID NO: 225:

(i) SEQUENCE CHARACTERISTICS:
(A) LENGTH: 15 amino acids
(B) TYPE: amino acid
(D) TOPOLOGY: linear

```
    (ii) MOLECULE TYPE: peptide (ix) FEATURE:
         (A) NAME/KEY: misc_feature
         (D) OTHER INFORMATION: "XMP.394"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(ix) FEATURE:
         (A) NAME/KEY: Modified-site
         (B) LOCATION: 1-15
         (D) OTHER INFORMATION: /label= D-Amino Acids /note=
             "Positions 1-15 are D-Amino Acids."

(ix) FEATURE:
         (A) NAME/KEY: Modified-site
         (B) LOCATION: 5 & 9
         (D) OTHER INFORMATION: /label= Substituted-Ala /note=
             "Positions 5 & 9 are beta-1-naphthyl-substituted."

(xi) SEQUENCE DESCRIPTION: SEQ ID NO: 225:

Lys Leu Phe Arg Ala Gln Ala Lys Ala Lys Gly Ser Ile Lys Ile
1               5                   10                  15

(2) INFORMATION FOR SEQ ID NO: 226:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.395"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(ix) FEATURE:
         (A) NAME/KEY: Modified-site
         (B) LOCATION: 6
         (D) OTHER INFORMATION: /label= Substituted-Ala /note=
             "Position 6 is beta-1-naphthyl-substituted."

(xi) SEQUENCE DESCRIPTION: SEQ ID NO: 226:

Lys Ser Lys Val Gly Ala Leu Ile Leu Leu Phe His Lys Lys
1               5                   10

(2) INFORMATION FOR SEQ ID NO: 227:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.396"

(ix) FEATURE:
         (A) NAME/KEY: Modified-site
         (B) LOCATION: C-Terminus
         (D) OTHER INFORMATION: /label= Amidation /note=
             "The C-Terminus is Amidated."
```

```
   (ix) FEATURE:
        (A) NAME/KEY: Modified-site
        (B) LOCATION: 6
        (D) OTHER INFORMATION: /label= Substituted-Ala /note=
            "Position 6 is beta-1-naphthyl-substituted."

(xi) SEQUENCE DESCRIPTION: SEQ ID NO: 227:

Lys Ser Lys Val Gly Ala Leu Ile Phe Leu Phe His Lys Lys
1               5                   10

(2) INFORMATION FOR SEQ ID NO: 228:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.397"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(ix) FEATURE:
        (A) NAME/KEY: Modified-site
        (B) LOCATION: 5
        (D) OTHER INFORMATION: /label= Substituted-Phe /note=
            "Position 5 is para-amino-substituted."

(ix) FEATURE:
        (A) NAME/KEY: Modified-site
        (B) LOCATION: 6
        (D) OTHER INFORMATION: /label= Substituted-Ala /note=
            "Position 6 is beta-1-naphthyl-substituted."

(xi) SEQUENCE DESCRIPTION: SEQ ID NO: 228:

Lys Ser Lys Val Phe Ala Leu Ile Gln Leu Trp His Lys Lys
1               5                   10

(2) INFORMATION FOR SEQ ID NO: 229:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.398"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(ix) FEATURE:
        (A) NAME/KEY: Modified-site
        (B) LOCATION: 10
        (D) OTHER INFORMATION: /label= Substituted-Ala /note=
            "Position 10 is D-beta-1-naphthyl-substituted."

(xi) SEQUENCE DESCRIPTION: SEQ ID NO: 229:

Lys Ser Lys Val Gly Trp Leu Ile Leu Ala Phe His Lys Lys
1               5                   10
```

(2) INFORMATION FOR SEQ ID NO: 230:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.399"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(xi) SEQUENCE DESCRIPTION: SEQ ID NO: 230:

Lys Ser Lys Val Gly Trp Leu Ile Phe Leu Trp His Lys Lys
1               5                   10

(2) INFORMATION FOR SEQ ID NO: 231:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.400"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(ix) FEATURE:
        (A) NAME/KEY: Modified-site
        (B) LOCATION: 6
        (D) OTHER INFORMATION: /label= Substituted-Ala /note=
        "Position 6 is beta-1-naphthyl-substituted."

(xi) SEQUENCE DESCRIPTION: SEQ ID NO: 231:

Lys Ser Lys Val Gly Ala Leu Ile Leu Leu Trp His Lys Lys
1               5                   10

(2) INFORMATION FOR SEQ ID NO: 232:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.401"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(ix) FEATURE:
        (A) NAME/KEY: Modified-site (B) LOCATION: 10
        (D) OTHER INFORMATION: /label= Substituted-Ala /note=
            "Position 10 is beta-1-naphthyl-substituted."

(xi) SEQUENCE DESCRIPTION: SEQ ID NO: 232:

Lys Ser Lys Val Gly Trp Leu Ile Phe Ala Phe His Lys Lys
1               5                   10

(2) INFORMATION FOR SEQ ID NO: 233:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.402"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(ix) FEATURE:
        (A) NAME/KEY: Modified-site
        (B) LOCATION: 6
        (D) OTHER INFORMATION: /label= Substituted-Ala /note=
            "Position 6 is beta-1-naphthyl-substituted."

(xi) SEQUENCE DESCRIPTION: SEQ ID NO: 233:

Lys Ser Lys Val Gly Ala Leu Ile Phe Leu Trp His Lys Lys
1               5                   10

(2) INFORMATION FOR SEQ ID NO: 234:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.403"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(ix) FEATURE:
        (A) NAME/KEY: Modified-site
        (B) LOCATION: 6 & 10
        (D) OTHER INFORMATION: /label= Substituted-Ala /note=
            "Position 6 & 10 is beta-1-naphthyl-substituted."

(xi) SEQUENCE DESCRIPTION: SEQ ID NO: 234:

Lys Ser Lys Val Gly Ala Leu Ile Gln Ala Trp His Lys Lys
1               5                   10

(2) INFORMATION FOR SEQ ID NO: 235:

(i) SEQUENCE CHARACTERISTICS:
        (A) LENGTH: 14 amino acids
        (B) TYPE: amino acid
        (D) TOPOLOGY: linear

```
    (ii) MOLECULE TYPE: peptide (ix) FEATURE:
         (A) NAME/KEY: misc_feature
         (D) OTHER INFORMATION: "XMP.404"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(ix) FEATURE:
         (A) NAME/KEY: Modified-site
         (B) LOCATION: 10
         (D) OTHER INFORMATION: /label= Substituted-Ala /note=
             "Position 10 is beta-1-naphthyl-substituted."

(xi) SEQUENCE DESCRIPTION: SEQ ID NO: 235:

Lys Ser Lys Val Gly Trp Leu Ile Phe Ala Trp His Lys Lys
1               5                   10

(2) INFORMATION FOR SEQ ID NO: 236:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.405"

(ix) FEATURE:
         (A) NAME/KEY: Modified-site
         (B) LOCATION: C-Terminus
         (D) OTHER INFORMATION: /label= Amidation /note=
             "The C-Terminus is Amidated."

(ix) FEATURE:
         (A) NAME/KEY: Modified-site
         (B) LOCATION: 10
         (D) OTHER INFORMATION: /label= Substituted-Ala /note=
             "Position 10 is beta-1-naphthyl-substituted."

(xi) SEQUENCE DESCRIPTION: SEQ ID NO: 236:

Lys Ser Lys Val Gly Trp Leu Ile Leu Ala Trp His Lys Lys
1               5                   10

(2) INFORMATION FOR SEQ ID NO: 237:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
         (A) NAME/KEY: misc_feature
         (D) OTHER INFORMATION: "XMP.406"

(xi) SEQUENCE DESCRIPTION: SEQ ID NO: 237:

Pro Lys Ser Lys Val Gly Ala Leu Ile Gln Leu Phe His Lys Lys
1               5                   10                  15

(2) INFORMATION FOR SEQ ID NO: 238:

(i) SEQUENCE CHARACTERISTICS:
        (A) LENGTH: 16 amino acids
        (B) TYPE: amino acid
```

```
            (D) TOPOLOGY: linear (ii) MOLECULE TYPE: peptide (ix) FEATURE:
            (A) NAME/KEY: misc_feature
            (D) OTHER INFORMATION: "XMP.407"

(xi) SEQUENCE DESCRIPTION: SEQ ID NO: 238:

Pro Lys Ser Lys Val Gly Ala Leu Ile Gln Leu Phe His Lys Lys Asp
1               5                   10                  15

(2) INFORMATION FOR SEQ ID NO: 239:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.408"

(ix) FEATURE:
            (A) NAME/KEY: misc_feature
            (D) OTHER INFORMATION: "Peptide is Cyclized Head to Tail"

(xi) SEQUENCE DESCRIPTION: SEQ ID NO: 239:

Leu Lys Lys Lys Trp Ala Ile Gln
1               5

(2) INFORMATION FOR SEQ ID NO: 240:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.409"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 240:

Ser Lys Trp Ala Ile Gln Leu Lys Lys
1               5

(2) INFORMATION FOR SEQ ID NO: 241:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.410"

(ix) FEATURE:
            (A) NAME/KEY: Modified-site
            (B) LOCATION: C-Terminus
            (D) OTHER INFORMATION: /label= Amidation /note=
```

"The C-Terminus is Amidated."

(ix) FEATURE:
        (A) NAME/KEY: Modified-site
        (B) LOCATION: N-Terminus
        (D) OTHER INFORMATION: /label= caprylyl group /note=
        "CH3-(CH2)6-CO at N-Terminus."

(xi) SEQUENCE DESCRIPTION: SEQ ID NO: 241:

Lys Lys Trp Ala Ile Gln Leu Lys Lys
1               5

(2) INFORMATION FOR SEQ ID NO: 242:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.411"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(ix) FEATURE:
        (A) NAME/KEY: Modified-site
        (B) LOCATION: N-Terminus
        (D) OTHER INFORMATION: /label= lauryl group /note=
        "CH3-(CH2)10-CO at N-Terminus."

(xi) SEQUENCE DESCRIPTION: SEQ ID NO: 242:

Lys Lys Trp Ala Ile Gln Leu Lys Lys
1               5

(2) INFORMATION FOR SEQ ID NO: 243:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.412"

(xi) SEQUENCE DESCRIPTION: SEQ ID NO: 243:

Leu Lys Lys Lys Trp Ala Ile Gln
1               5

(2) INFORMATION FOR SEQ ID NO: 244:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.414"

(ix) FEATURE:
        (A) NAME/KEY: Modified-site

```
        (B) LOCATION: 1-10
        (D) OTHER INFORMATION: /label= D-Amino Acids /note=
            "Positions 1-10 are D-amino acids"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(ix) FEATURE:
        (A) NAME/KEY: Modified-site
        (B) LOCATION: N-Terminus
        (D) OTHER INFORMATION: /label= caprylyl group /note=
            "CH3-(CH2)6-CO at N-Terminus."

(xi) SEQUENCE DESCRIPTION: SEQ ID NO: 244:

Lys Trp Leu Ile Gln Leu Phe His Lys Lys
1               5                   10

(2) INFORMATION FOR SEQ ID NO: 245:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.415"

(ix) FEATURE:
        (A) NAME/KEY: Modified-site
        (B) LOCATION: 1-10
        (D) OTHER INFORMATION: /label= D-Amino Acids /note=
            "Positions 1-10 are D-amino acids"

(ix) FEATURE:
        (A) NAME/KEY: Modified-site
        (B) LOCATION: C-Terminus
        (D) OTHER INFORMATION: /label= Amidation /note=
            "The C-Terminus is Amidated."

(ix) FEATURE:
        (A) NAME/KEY: Modified-site
        (B) LOCATION: N-Terminus
        (D) OTHER INFORMATION: /label= lauryl group /note=
            "CH3-(CH2)10-CO at N-Terminus."

(xi) SEQUENCE DESCRIPTION: SEQ ID NO: 245:

Lys Trp Leu Ile Gln Leu Phe His Lys Lys
1               5                   10

(2) INFORMATION FOR SEQ ID NO: 246:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.416"

(ix) FEATURE:
        (A) NAME/KEY: Modified-site
        (B) LOCATION: 1-10
        (D) OTHER INFORMATION: /label= D-Amino Acids /note=
            "Positions 1-10 are D-amino acids"

(ix) FEATURE:
```

(A) NAME/KEY: Modified-site
            (B) LOCATION: C-Terminus
            (D) OTHER INFORMATION: /label= Amidation /note=
            "The C-Terminus is Amidated."

(ix) FEATURE:
            (A) NAME/KEY: Modified-site
            (B) LOCATION: N-Terminus
            (D) OTHER INFORMATION: /label= 8-amino-octanyl group /note=
            "NH2-(CH2)7-CO at N-Terminus."

(xi) SEQUENCE DESCRIPTION: SEQ ID NO: 246:

Lys Trp Leu Ile Gln Leu Phe His Lys Lys
1               5                   10

(2) INFORMATION FOR SEQ ID NO: 247:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.417"

(ix) FEATURE:
            (A) NAME/KEY: Modified-site
            (B) LOCATION: 1-10
            (D) OTHER INFORMATION: /label= D-Amino Acids /note=
            "Positions 1-10 are D-amino acids"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(ix) FEATURE:
            (A) NAME/KEY: Modified-site
            (B) LOCATION: N-Terminus
            (D) OTHER INFORMATION: /label= 12-amino-dodecanyl group /note=
            "NH2-(CH2)11-CO at N-Terminus."

(xi) SEQUENCE DESCRIPTION: SEQ ID NO: 247:

Lys Trp Leu Ile Gln Leu Phe His Lys Lys
1               5                   10

(2) INFORMATION FOR SEQ ID NO: 248:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (ix) FEATURE:
            (A) NAME/KEY: misc_feature
            (D) OTHER INFORMATION: "XMP.418"

(ix) FEATURE:
            (A) NAME/KEY: Modified-site
            (B) LOCATION: C-Terminus
            (D) OTHER INFORMATION: /label= Amidation /note=
            "The C-Terminus is Amidated."

(xi) SEQUENCE DESCRIPTION: SEQ ID NO: 248:

Lys Ser Lys Val Pro Trp Leu Ile Gln Leu Phe His Lys Lys
1               5                   10

(2) INFORMATION FOR SEQ ID NO: 249:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.419"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(ix) FEATURE:
        (A) NAME/KEY: Modified-site
        (B) LOCATION: 1-9
        (D) OTHER INFORMATION: /label= D-Amino Acids /note=
        "Positions 1-9 are D-Amino Acids."

(xi) SEQUENCE DESCRIPTION: SEQ ID NO: 249:

```
Lys Trp Leu Ile Leu Phe His Lys Lys
1               5
```

(2) INFORMATION FOR SEQ ID NO: 250:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: misc_feature
        (D) OTHER INFORMATION: "XMP.420"

(ix) FEATURE:
        (A) NAME/KEY: Modified-site
        (B) LOCATION: C-Terminus
        (D) OTHER INFORMATION: /label= Amidation /note=
        "The C-Terminus is Amidated."

(ix) FEATURE:
        (A) NAME/KEY: Modified-site
        (B) LOCATION: N-Terminus
        (D) OTHER INFORMATION: /label= /note=
        "The N-Terminus is protected by 1-Fluorenylmethyl-
            oxycarbonyl (Fmoc)"

(ix) FEATURE:
        (A) NAME/KEY: misc_feature
        (D) OTHER INFORMATION: "XMP.365"

(ix) FEATURE:
        (A) NAME/KEY: Modified-site
        (B) LOCATION: 1-10
        (D) OTHER INFORMATION: /label= D-Amino Acids /note=
        "Positions 1-10 are D-amino acids"

(xi) SEQUENCE DESCRIPTION: SEQ ID NO: 250:

```
Lys Trp Leu Ile Gln Leu Phe His Lys Lys
1               5                   10
```

(2) INFORMATION FOR SEQ ID NO: 251:

(i) SEQUENCE CHARACTERISTICS:
        (A) LENGTH: 1813 base pairs
        (B) TYPE: nucleic acid
        (C) STRANDEDNESS: single

```
        (D) TOPOLOGY: linear (ii) MOLECULE TYPE: cDNA (ix) FEATURE:
         (A) NAME/KEY: CDS
         (B) LOCATION: 31..1491

(ix) FEATURE:
         (A) NAME/KEY: mat_peptide
         (B) LOCATION: 124..1491

(ix) FEATURE:
         (A) NAME/KEY: misc_feature
         (D) OTHER INFORMATION: "rBPI"

(xi) SEQUENCE DESCRIPTION: SEQ ID NO: 251:

CAGGCCTTGA GGTTTTGGCA GCTCTGGAGG ATG AGA GAG AAC ATG GCC AGG GGC        54
                              Met Arg Glu Asn Met Ala Arg Gly
                              -31 -30                 -25

CCT TGC AAC GCG CCG AGA TGG GTG TCC CTG ATG GTG CTC GTC GCC ATA        102
Pro Cys Asn Ala Pro Arg Trp Val Ser Leu Met Val Leu Val Ala Ile
            -20                 -15                 -10

GGC ACC GCC GTG ACA GCG GCC GTC AAC CCT GGC GTC GTG GTC AGG ATC        150
Gly Thr Ala Val Thr Ala Ala Val Asn Pro Gly Val Val Val Arg Ile
        -5                   1               5

TCC CAG AAG GGC CTG GAC TAC GCC AGC CAG CAG GGG ACG GCC GCT CTG        198
Ser Gln Lys Gly Leu Asp Tyr Ala Ser Gln Gln Gly Thr Ala Ala Leu
 10              15                  20                  25

CAG AAG GAG CTG AAG AGG ATC AAG ATT CCT GAC TAC TCA GAC AGC TTT        246
Gln Lys Glu Leu Lys Arg Ile Lys Ile Pro Asp Tyr Ser Asp Ser Phe
             30                  35                  40

AAG ATC AAG CAT CTT GGG AAG GGG CAT TAT AGC TTC TAC AGC ATG GAC        294
Lys Ile Lys His Leu Gly Lys Gly His Tyr Ser Phe Tyr Ser Met Asp
             45                  50                  55

ATC CGT GAA TTC CAG CTT CCC AGT TCC CAG ATA AGC ATG GTG CCC AAT        342
Ile Arg Glu Phe Gln Leu Pro Ser Ser Gln Ile Ser Met Val Pro Asn
         60                  65                  70

GTG GGC CTT AAG TTC TCC ATC AGC AAC GCC AAT ATC AAG ATC AGC GGG        390
Val Gly Leu Lys Phe Ser Ile Ser Asn Ala Asn Ile Lys Ile Ser Gly
     75                  80                  85

AAA TGG AAG GCA CAA AAG AGA TTC TTA AAA ATG AGC GGC AAT TTT GAC        438
Lys Trp Lys Ala Gln Lys Arg Phe Leu Lys Met Ser Gly Asn Phe Asp
 90                  95                 100                 105

CTG AGC ATA GAA GGC ATG TCC ATT TCG GCT GAT CTG AAG CTG GGC AGT        486
Leu Ser Ile Glu Gly Met Ser Ile Ser Ala Asp Leu Lys Leu Gly Ser
             110                 115                 120

AAC CCC ACG TCA GGC AAG CCC ACC ATC ACC TGC TCC AGC TGC AGC AGC        534
Asn Pro Thr Ser Gly Lys Pro Thr Ile Thr Cys Ser Ser Cys Ser Ser
             125                 130                 135

CAC ATC AAC AGT GTC CAC GTG CAC ATC TCA AAG AGC AAA GTC GGG TGG        582
His Ile Asn Ser Val His Val His Ile Ser Lys Ser Lys Val Gly Trp
             140                 145                 150

CTG ATC CAA CTC TTC CAC AAA AAA ATT GAG TCT GCG CTT CGA AAC AAG        630
Leu Ile Gln Leu Phe His Lys Lys Ile Glu Ser Ala Leu Arg Asn Lys
             155                 160                 165

ATG AAC AGC CAG GTC TGC GAG AAA GTG ACC AAT TCT GTA TCC TCC AAG        678
Met Asn Ser Gln Val Cys Glu Lys Val Thr Asn Ser Val Ser Ser Lys
170                 175                 180                 185

CTG CAA CCT TAT TTC CAG ACT CTG CCA GTA ATG ACC AAA ATA GAT TCT        726
Leu Gln Pro Tyr Phe Gln Thr Leu Pro Val Met Thr Lys Ile Asp Ser
                 190                 195                 200

GTG GCT GGA ATC AAC TAT GGT CTG GTG GCA CCT CCA GCA ACC ACG GCT        774
```

```
Val Ala Gly Ile Asn Tyr Gly Leu Val Ala Pro Pro Ala Thr Thr Ala
            205                 210                 215

GAG ACC CTG GAT GTA CAG ATG AAG GGG GAG TTT TAC AGT GAG AAC CAC      822
Glu Thr Leu Asp Val Gln Met Lys Gly Glu Phe Tyr Ser Glu Asn His
        220                 225                 230

CAC AAT CCA CCT CCC TTT GCT CCA CCA GTG ATG GAG TTT CCC GCT GCC      870
His Asn Pro Pro Pro Phe Ala Pro Pro Val Met Glu Phe Pro Ala Ala
            235                 240                 245

CAT GAC CGC ATG GTA TAC CTG GGC CTC TCA GAC TAC TTC TTC AAC ACA      918
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA      966
Ala Gly Leu Val Tyr Gln Glu Ala Gly Val Leu Lys Met Thr Leu Arg
                270                 275                 280

GAT GAC ATG ATT CCA AAG GAG TCC AAA TTT CGA CTG ACA ACC AAG TTC     1014
Asp Asp Met Ile Pro Lys Glu Ser Lys Phe Arg Leu Thr Thr Lys Phe
            285                 290                 295

TTT GGA ACC TTC CTA CCT GAG GTG GCC AAG AAG TTT CCC AAC ATG AAG     1062
Phe Gly Thr Phe Leu Pro Glu Val Ala Lys Lys Phe Pro Asn Met Lys
        300                 305                 310

ATA CAG ATC CAT GTC TCA GCC TCC ACC CCG CCA CAC CTG TCT GTG CAG     1110
Ile Gln Ile His Val Ser Ala Ser Thr Pro Pro His Leu Ser Val Gln
    315                 320                 325

CCC ACC GGC CTT ACC TTC TAC CCT GCC GTG GAT GTC CAG GCC TTT GCC     1158
Pro Thr Gly Leu Thr Phe Tyr Pro Ala Val Asp Val Gln Ala Phe Ala
330                 335                 340                 345

GTC CTC CCC AAC TCC TCC CTG GCT TCC CTC TTC CTG ATT GGC ATG CAC     1206
Val Leu Pro Asn Ser Ser Leu Ala Ser Leu Phe Leu Ile Gly Met His
                350                 355                 360

ACA ACT GGT TCC ATG GAG GTC AGC GCC GAG TCC AAC AGG CTT GTT GGA     1254
Thr Thr Gly Ser Met Glu Val Ser Ala Glu Ser Asn Arg Leu Val Gly
            365                 370                 375

GAG CTC AAG CTG GAT AGG CTG CTC CTG GAA CTG AAG CAC TCA AAT ATT     1302
Glu Leu Lys Leu Asp Arg Leu Leu Leu Glu Leu Lys His Ser Asn Ile
        380                 385                 390

GGC CCC TTC CCG GTT GAA TTG CTG CAG GAT ATC ATG AAC TAC ATT GTA     1350
Gly Pro Phe Pro Val Glu Leu Leu Gln Asp Ile Met Asn Tyr Ile Val
    395                 400                 405

CCC ATT CTT GTG CTG CCC AGG GTT AAC GAG AAA CTA CAG AAA GGC TTC     1398
Pro Ile Leu Val Leu Pro Arg Val Asn Glu Lys Leu Gln Lys Gly Phe
410                 415                 420                 425

CCT CTC CCG ACG CCG GCC AGA GTC CAG CTC TAC AAC GTA GTG CTT CAG     1446
Pro Leu Pro Thr Pro Ala Arg Val Gln Leu Tyr Asn Val Val Leu Gln
                430                 435                 440

CCT CAC CAG AAC TTC CTG CTG TTC GGT GCA GAC GTT GTC TAT AAA         1491
Pro His Gln Asn Phe Leu Leu Phe Gly Ala Asp Val Val Tyr Lys
            445                 450                 455

TGAAGGCACC AGGGGTGCCG GGGGCTGTCA GCCGCACCTG TTCCTGATGG GCTGTGGGGC   1551

ACCGGCTGCC TTTCCCCAGG GAATCCTCTC CAGATCTTAA CCAAGAGCCC CTTGCAAACT   1611

TCTTCGACTC AGATTCAGAA ATGATCTAAA CACGAGGAAA CATTATTCAT TGGAAAAGTG   1671

CATGGTGTGT ATTTTAGGGA TTATGAGCTT CTTTCAAGGG CTAAGGCTGC AGAGATATTT   1731

CCTCCAGGAA TCGTGTTTCA ATTGTAACCA AGAAATTTCC ATTTGTGCTT CATGAAAAAA   1791

AACTTCTGGT TTTTTTCATG TG                                           1813

(2) INFORMATION FOR SEQ ID NO: 252:

(i) SEQUENCE CHARACTERISTICS:
```

(A) LENGTH: 487 amino acids
(B) TYPE: amino acid
(D) TOPOLOGY: linear (ii) MOLECULE TYPE: protein (xi) SEQUENCE DESCRIPTION: SEQ ID NO: 252:

```
Met Arg Glu Asn Met Ala Arg Gly Pro Cys Asn Ala Pro Arg Trp Val
-31 -30                 -25                 -20

Ser Leu Met Val Leu Val Ala Ile Gly Thr Ala Val Thr Ala Ala Val
-15             -10                 -5                        1

Asn Pro Gly Val Val Arg Ile Ser Gln Lys Gly Leu Asp Tyr Ala
             5                 10                 15

Ser Gln Gly Thr Ala Ala Leu Gln Lys Glu Leu Lys Arg Ile Lys
         20                  25                 30

Ile Pro Asp Tyr Ser Asp Ser Phe Lys Ile Lys His Leu Gly Lys Gly
         35                  40                 45

His Tyr Ser Phe Tyr Ser Met Asp Ile Arg Glu Phe Gln Leu Pro Ser
 50                 55                  60                   65

Ser Gln Ile Ser Met Val Pro Asn Val Gly Leu Lys Phe Ser Ile Ser
             70                 75                  80

Asn Ala Asn Ile Lys Ile Ser Gly Lys Trp Lys Ala Gln Lys Arg Phe
             85                 90                 95

Leu Lys Met Ser Gly Asn Phe Asp Leu Ser Ile Glu Gly Met Ser Ile
            100                 105                 110

Ser Ala Asp Leu Lys Leu Gly Ser Asn Pro Thr Ser Gly Lys Pro Thr
            115                 120                 125

Ile Thr Cys Ser Ser Cys Ser Ser His Ile Asn Ser Val His Val His
130             135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
                165                 170                 175

Val Thr Asn Ser Val Ser Ser Lys Leu Gln Pro Tyr Phe Gln Thr Leu
            180                 185                 190

Pro Val Met Thr Lys Ile Asp Ser Val Ala Gly Ile Asn Tyr Gly Leu
            195                 200                 205

Val Ala Pro Pro Ala Thr Thr Ala Glu Thr Leu Asp Val Gln Met Lys
210             215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
            260                 265                 270

Gly Val Leu Lys Met Thr Leu Arg Asp Asp Met Ile Pro Lys Glu  Ser
275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
            340                 345                 350
```

```
Ser Leu Phe Leu Ile Gly Met His Thr Thr Gly Ser Met Glu Val Ser
    355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
                405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
    435                 440                 445

Gly Ala Asp Val Val Tyr Lys
450                 455
```

(2) INFORMATION FOR SEQ ID NO: 253:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 253:

```
Leu Ile Gln Leu
1
```

(2) INFORMATION FOR SEQ ID NO: 254:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 254:

```
Ile Gln Leu Phe
1
```

(2) INFORMATION FOR SEQ ID NO: 255:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 255:

```
Trp Leu Ile Gln Leu
1               5
```

(2) INFORMATION FOR SEQ ID NO: 256:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 256:

```
                                -continued

Leu Ile Gln Leu Phe
1               5

(2) INFORMATION FOR SEQ ID NO: 257:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 257:

Trp Leu Ile Gln Leu Phe
1               5
```

ANTI-FUNGAL PEPTIDES

This is a continuation of U.S. application Ser. No. 09/227,659, filed Jan. 8, 1999, now U.S. Pat. No. 6,156,730, which is a continuation of U.S. application Ser. No. 08/621,259, filed Mar. 21, 1996, now U.S. Pat. No. 5,858,974, which is a continuation-in-part of U.S. patent application Ser. No. 08/504,841 filed Jul. 20, 1995, now abandoned, which a is CIP of Ser. No. 08/372,105 filed Jan. 13, 1995, now U.S. Pat. No. 5,627,153, which is a CIP of Ser. No. 08/306,473 filed Sep. 15, 1994, now U.S. Pat. No. 5,652,332, and is a CIP of Ser. No. 08/273,540 filed Jul. 11, 1994, now abandoned, which is a CIP of Ser. No. 08/209,762 filed Mar. 11, 1994, now U.S. Pat. No. 5,733,872, which is a CIP of Ser. No. 08/183,222 filed Jan. 14, 1994, now abandoned, which is a CIP of Ser. No. 08/093,202 filed Jul. 15, 1993, now abandoned, which is a CIP of Ser. No. 08/030,644 filed Mar. 12, 1993, now U.S. Pat. No. 5,348,942

BACKGROUND OF THE INVENTION

The present invention relates generally to anti-fungal peptides derived from or based on Domain III (amino acids 142–169) of bactericidal/permeability-increasing protein (BPI) and therapeutic uses of such peptides.

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254:11000 (1979)] or *E. coli* affinity chromatography [Weiss, et al., *Blood*, 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J. Biol. Chem.*, 264:9505 (1989), incorporated herein by reference. The Gray et al. DNA and amino acid sequences are set out in SEQ ID NOS: 251 and 252 hereto.

BPI is a strongly cationic protein. The N-terminal half of BPI accounts for the high net positive charge; the C-terminal half of the molecule has a net charge of −3. [Elsbach and Weiss (1981), supra.] A proteolytic N-terminal fragment of BPI having a molecular weight of about 25 kD has an amphipathic character, containing alternating hydrophobic and hydrophilic regions. This N-terminal fragment of human BPI possesses the anti-bacterial efficacy of the naturally-derived 55 kD human BPI holoprotein. [Ooi et al., *J. Bio. Chem.*, 262: 14891–14894 (1987)]. In contrast to the N-terminal portion, the C-terminal region of the isolated human BPI protein displays only slightly detectable anti-bacterial activity against gram-negative organisms. [Ooi et al., *J. Exp. Med.*, 174:649 (1991).] An N-terminal BPI fragment of approximately 23 kD, refereed to as "rBPI$_{23}$," has been produced by recombinant means and also mains anti-bacterial activity against gram-negative organisms [Gazzano-Santoro et al., *Infect. Immun.* 60:4754–4761 (1992)]. In that publication, an expression vector was used as a source of DNA encoding a recombinant expression product (rBPI$_2$). The vector was constructed to encode the 31-residue signal sequence and the first 199 amino acids of the N-terminus of the mature human BPI, as set out in SEQ ID NOS: 251 and 252 taken from Gray et al., supra, except that valine at position 151 is specified by GTG rather than GTC and residue 185 is glutamic acid (specified by GAG) rather than lysine (specified by AAG). Recombinant holoprotein, also referred to as rBPI, has also been produced having the sequence set out in SEQ ID NOS: 251 and 252 taken from Gray et al., supra, with the exceptions noted for rBPI$_{23}$. An N-terminal fragment analog designated rBPI$_{21}$, or rBPI$_{21}$Δcys has been described in co-owned, copending U.S. Pat. No. 5,420,019 which is incorporated herein by reference. This analog comprises the first 193 amino acids of BPI holoprotein as set out in SEQ ID NOS: 251 and 252 but wherein the cysteine at residue number 132 is substituted with alanine, and with the exceptions noted for rBPI23.

The bactericidal effect of BPI has been reported to be highly specific to gram-negative species, e.g., in Elsbach and Weiss, *Inflammation: Basic Pnnciples and Clinical Correlates*, eds. Gallin et al., Chapter 30. Raven Press, Ltd. (1992). BPI is commonly thought to be non-toxic for other microorganisms, including yeast, and for higher eukaryotic cells. Elsbach and Weiss (1992), supra, reported that BPI exhibits anti-bacterial activity towards a broad range of gram-negative bacteria at concentrations as low as $10^{-8}$ to $10^{-9}$ M, but that 100- to 1,000-fold higher concentrations of BPI were non-toxic to all of the gram-positive bacterial species, yeasts, and higher eukaryotic cells tested at that time. It was also reported that BPI at a concentration of $10^{-6}$ M or 160 μg/ml had no toxic effect, when tested at a pH of either 7.0 or 5.5, on the gram-positive organisms *Staphylococcus aureus* (four strains), *Staphylococcus epidermidis, Streptococcus faecalis, Bacillus subtilis, Micrococcus lysodeikricus*, and *Listeria monocytogenes*. BPI at $10^{-6}$ M reportedly had no toxic effect on the fungi *Candida albicans* and *Candida parapsilosis* at pH 7.0 or 5.5, and was non-toxic to higher eukaryotic cells such as human, rabbit and sheep red blood cells and several human tumor cell lines. See also Elsbach and Weiss, *Advances in Inflammation Research*, ed. G. Weissmann, Vol. 2, pages 95–113 Raven Press (1981). This reported target cell specificity was believed to be the result of the strong attraction of BPI for lipopolysaccharide (LPS), which is unique to the outer membrane (or envelope) of gram-negative organisms.

The precise mechanism by which BPI kills gram-negative bacteria is not yet completely elucidated, but it is believed that BPI must first bind to the surface of the bacteria through hydrophobic and electrostatic interactions between the cationic BPI protein and negatively charged sites on LPS. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. BPI is thought to act in two stages. The first is a sublethal stage that is characterized by immediate growth arrest, permeabilization of the outer membrane and selective activation of bacterial enzymes that hydrolyze phospholipids and peptidoglycans. Bacteria at this stage can be rescued by growth in serum albumin supplemented media [Mannion et al., *J. Clin. Invest.*, 85:853–860 (1990)]. The second stage, defined by growth inhibition that cannot be reversed by serum albumin, occurs after prolonged exposure of the bacteria to BPI and is characterized by extensive physiologic and structural changes, including apparent damage to the inner cytoplasmic membrane.

Initial binding of BPI to LPS leads to organizational changes that probably result from binding to the anionic groups in the KDO region of LPS, which normally stabilize the outer membrane through binding of $Mg^{++}$ and $Ca^{++}$. Attachment of BPI to the outer membrane of gram-negative bacteria produces rapid permeabilization of the outer membrane to hydrophobic agents such as actinomycin D. Binding of BPI and subsequent gram-negative bacterial killing depends, at least in part, upon the LPS polysaccharide chain length, with long O-chain bearing, "smooth" organisms being more resistant to BPI bactericidal effects than short O-chain bearing, "rough" organisms [weiss et al., *J. Clin. invest.* 65: 619–628 (1980)]. This first stage of BPI action, permeabilization of the gram-negative outer envelope, is reversible upon dissociation of the BPI, a process requiring the presence of divalent cations and synthesis of new LPS [Weiss et al., *J. Immunol.* 132: 3109–3115 (1984)]. Loss of gram-negative bacterial viability, however, is not reversed by processes which restore the envelope integrity, suggesting that the bactericidal action is mediated by additional lesions induced in the target organism and which may be situated at the cytoplasmic membrane [Mannion et al., *J. Clin. Invest.* 86: 631–641 (1990)]. Specific investigation of this possibility has shown that on a molar basis BPI is at least as inhibitory of cytoplasmic membrane vesicle function as polymyxin B [In't Veld et al., *Infection and Immunity* 56: 1203–1208 (1988)] but the exact mechanism as well as the relevance of such vesicles to studies of intact organisms has not yet been elucidated.

Three separate functional domains within the recombinant 23 kD N-terminal BPI sequence have been discovered [Little et al., *J. Biol. Chem.* 269: 1865 (1994)]. These functional domains of BPI designate a region of the amino acid sequence of BPI that contributes to the total biological activity of the protein and were essentially defined by the activities of proteolytic cleavage fragments, overlapping 15-mer peptides and other synthetic peptides. Domain I is defined as the amino acid sequence of BPI comprising from about amino acid 17 to about amino acid 45. Peptides based on this domain are moderately active in both the inhibition of LPS-induced LAL activity and in heparin binding assays, and do not exhibit significant bactericidal activity. Domain II is defined as the amino acid sequence of BPI comprising from about amino acid 65 to about amino acid 99. Peptides based on this domain exhibit high LPS and heparin binding capacity and are bactericidal. Domain III is defined as the amino acid sequence of BPI comprising from about amino acid 142 to about amino acid 169. Peptides based on this domain exhibit high LPS and heparin binding activity and are bactericidal. The biological activities of functional domain peptides may include LPS binding, LPS neutralization, heparin binding, heparin neutralization or bactericidal activity.

Fungi are eukaryotic cells that may reproduce sexually or asexually and may be biphasic, with one form in nature and a different form in the infected host. Fungal diseases are referred to as mycoses. Some mycoses are endemic, i.e. infection is acquired in the geographic area that is the natural habitat of that fungus. These endemic mycoses are usually self-limited and minimally symptomatic. Some mycoses are chiefly opportunistic, occurring in immunocompromised patients such as organ transplant patients, cancer patients undergoing chemotherapy, burn patients, AIDS patients, or patients with diabetic ketoacidosis.

Fungal infections are becoming a major health concern for a number of reasons, including the limited number of anti-fungal agents available, the increasing incidence of species resistant to older anti-fungal agents, and the growing population of immunocompromised patients at risk for opportunistic fungal infections. The incidence of systemic fungal infections increased 600% in teaching hospitals and 220% in non-teaching hospitals during the 1980's. The most common clinical isolate is *Candida albicans* (comprising about 19% of all isolates). In one study, nearly 40% of all deaths from hospital-acquired infections were due to fungi. [Sternberg, *Science*, 266:1632–1634 (1994).]

Anti-fungal agents include three main groups. The major group includes polyene derivatives, including amphotericin B and the structurally related compounds nystatin and pinaricin. These are broad-spectrum anti-fungals that bind to ergosterol, a component of fungal cell membranes, and thereby disrupt the membranes. Amphotericin B is usually effective for systemic mycoses, but its administration is limited by toxic effects that include fever and kidney damage, and other accompanying side effects such as anemia, low blood pressure, headache, nausea, vomiting and phlebitis. The unrelated anti-fungal agent flucytosine (5-fluorocytosine), an orally absorbed drug, is frequently used as an adjunct to amphotericin B treatment for some forms of candidiasis and cryptococcal meningitis. Its adverse effects include bone marrow depression with leukopenia and thrombocytopenia.

The second major group of anti-fungal agents includes azole derivatives which impair synthesis of ergosterol and lead to accumulation of metabolites that disrupt the function of fungal membrane-bound enzyme systems (e.g., cytochrome P450) and inhibit fungal growth. Significant inhibition of mammalian P450 results in significant drug interactions. This group of agents includes ketoconazole, clotrimazole, miconazole, econazole, butoconazole, oxiconazole, sulconazole, terconazole, fluconazole and itraconazole. These agents may be administered to treat systemic mycoses. Ketoconazole, an orally administered imidazole, is used to treat nonmeningeal blastomycosis, histoplasmosis, coccidioidomycosis and paracoccidioidomycosis in non-immunocompromised patients, and is also useful for oral and esophageal candidiasis. Adverse effects include rare drug-induced hepatitis; ketoconazole is also contraindicated in pregnancy. Itraconazole appears to have fewer side effects than ketoconazole and is used for most of the same indications. Fluconazole also has fewer side effects than ketoconazole and is used for oral and esophageal candidiasis and cryptococcal meningitis. Miconazole is a parenteral imidazole with efficacy in coccidioidomycosis and several other mycoses, but has side effects including hyperlipidemia and hyponatremia.

The third major group of anti-fungal agents includes allylarines-thiocarbamates, which are generally used to treat skin infections. This group includes tolnaftate and naftifine.

Another anti-fungal agent is griseofulvin, a fungistatic agent which is administered orally for fungal infections of skin, hair or nails that do not respond to topical treatment.

Most endemic mycoses are acquired by the respiratory route and are minimally symptomatic; cough, fever, headache, and pleuritic pain may be seen. Occasionally, endemic mycoses may cause progressive pulmonary disease or systemic infection. Histoplasmosis, caused by Histoplasmu, is the most common endemic respiratory mycosis in the United States; over 40 million people have been infected. The disease is noncontagious and ordinarily self-limited, but chronic pulmonary infection and disseminated infection may occur. Pulmonary infection rarely requires treatment, but disseminated infection may be treated with amphotericin B. Coccidioidomycosis, caused by Coccidioides, is a noncontagious respiratory mycosis prevalent in the southwest United States. It also is usually self-limited but may lead to chronic pulmonary infection or disseminated infection. Amphotericin B or miconazole may be given for treatment. Blastomycosis, caused by Blastomyces is a noncontagious, subacute or chronic endemic mycosis most commonly seen in the southeast United States. Most pulmonary infections are probably self-limited. Patients with progressive lung disease or disseminated disease, and immunocompromised patients, may be treated systemically with amphotericin B. Paracoccidioidomycosis, caused by Paracocddioides, is a noncontagious respiratory mycosis that is the most common systemic mycosis in South America. It may be acute and self-limited or may produce progressive pulmonary disease or extripulmonary dissemination. Disseminated disease is generally fatal in the absence of therapy. Sulfonamides may be used but have a low success rate. Amphotericin B produces a higher response rate but relapses may still occur.

Cryptococcosis is a noncontagious, often opportunistic mycosis. It is characterized by respiratory involvement or hematogenous dissemination, often with meningitis. A major etiologic agent is *C. neoformans*. Most pulmonary infections are probably overlooked, but cryptococcal meningitis, which accounts for 90% of reported disease, is dramatic and seldom overlooked. Cryptococcosis is a particular problem in immunocompromised patients; cryptococcal meningitis occurs in 7 to 10% of AIDS patients. The principal symptom of meningitis is headache; associated findings include mental changes, ocular symptoms, hearing deficits, nausea, vomiting, and seizures. Without treatment, 80% of patients die within two years. in meningitis, cryptococci can be observed in India ink preparations of cerebrospinal fluid sediment, and can be cultured from the cerebrospinal fluid. Treatment is generally with fluconazole or the combination of amphotericin B and flucytosine, although amphotericin B does not cross the blood brain barrier.

Aspergillosis is a term that encompasses a variety of disease processes caused by Aspergillus species. Aspergillus species are ubiquitous; their spores are constantly being inhaled. Of the more than 300 species known, only a few are ordinarily pathogenic for man: *A. fumigatus, A. flavus, A. niger, A. nidulans, A. terreus, A. sydowi, A. flavarus*, and *A. glaucus*. Aspergillosis is increasing in prevalence and is particularly a problem among patients with chronic respiratory disease or immunocompromised patients. Among immunocompromised patients, aspergillosis is second only to candidiasis as the most common opportunistic mycosis and accounts for about 15% of the systemic mycoses in this group. Opportunistic pulmonary aspergillosis is characterized by widespread bronchial erosion and ulceration, followed by invasion of the pulmonary vessels, with thrombosis, embolization and infarction. Clinically, infection manifests as a necrotizing patchy bronchopneumonia, sometimes with hemorrhagic pulmonary infarction. In about 40% of cases, there is hematogenous spread to other sites. Aspergillosis is also a rare but devastating complication of burn wounds; amputation is often required for cure. Invasive aspergillosis is commonly fatal, so aggressive diagnosis and treatment is required. Blood, urine and cerebrospinal fluid cultures are rarely positive, but fungi can be seen in smears and biopsies. Amphotericin B can be given for treatment.

Mucormycosis is an acute suppurative opportunistic mycosis that produces rhinocerebral, pulmonary or disseminated disease in immunocompromised patients, and local or disseminated disease in patients with burns or open wounds. Infection is caused by fungi in the class Zygomycetes, and include Basidiobolus, Conidiobolus, Rhizopus, Mucor, Absidia, Morrierella, Cunninghamella, and Saksenaea. Rhinocerebral mucormycosis accounts for about half of all cases of mucormycosis. It is one of the most rapidly fatal fungal diseases, with death occurring within 2–10 days in untreated patients. Early clinical signs include nasal stuffiness, bloody nasal discharge, facial swelling and facial pain. The infection then spreads to the eyes, cranial nerves and brain. Pulmonary mucormycosis is nearly as common as rhinocerebral disease and manifests with the same necrotizing and infarction as aspergiulosis. Fungi are virtually never seen or cultured from blood, sputum or cerebrospinal fluid. Disseminated mucormycosis may follow pulmonary or burn wound infection. Treatment is with amphotericin B.

Candidiasis is a general term for a variety of local and systemic processes caused by colonization or infection of the host by species of the yeast Candida. Candidiasis occurs worldwide; superficial infections of the skin, mouth and other mucus membranes are universal. Invasive systemic disease has become a problem due to the use of high doses of antibiotics that destroy normal bacterial flora, immunosuppressive agents, and agents toxic to bone marrow, e.g., during cancer therapy. Neutropenia is a major risk factor for candida dissemination. Candidiasis is also seen among immunocompromised individuals such as AIDS patients, organ transplant patients, patients receiving parenteral nutrition, and cancer patients undergoing radiation treatment and chemotherapy. It is the most common opportunistic mycosis in the world. The most common etiologic agent is *Candida albicans*. Other infectious species include *C. tropicalis, C. parapsilosis, C. stellatoidea, C. krusei, C. parakrusei, C. lusitaniae, C. pseudotropicalis, C. guilliermondi* and *C. glabrata*. *Candida albicans* is normally found in the mouth, throat, gastrointestinal tract and vagina of humans. Non-albicans species frequently colonize skin. candida species occur in two forms that are not temperature- or host-dependent. The usual colonizing forms are yeasts that may assume a pseudomycelial configuration, especially during tissue invasion. Pseudomyceliae result from the sequential budding of yeasts into branching chains of elongated organisms.

*Candida albicans* contains cell wall mannoproteins that appear to be responsible for attachment of the yeast cells to specific host tissues. It has been reported that the mannan portion, rather than the protein portion, of the mannoproteins is responsible for adherence of fungal cells to spleen and lymph node tissues in mice. [Kanbe et al., *Infection Immunity*, 61:2578–2584 (1993).]

*C. albicans* also binds avidly to extracellular matrix (ECM) proteins such as fibronectin, laminin, and types I and IV collagen, all of which contain heparin-binding domains. This suggests *C. albicans* may express a heparin-like surface molecule. Adherence of *C. albicans* to the ECM may be important in the pathogenesis of disseminated candidiasis. It has been demonstrated that heparin, heparan sulfate and dextran sulfate glycosaminoglycans (GAGs) inhibit adherence of *C. albicans* to ECM and ECM proteins, possibly by a mechanism involving binding of GAGs to ECM proteins, thus masking these selective ligands. [Klotz et al., *FEMS Microbiology Letters*, 78:205–208 (1992).]

Clinically, candidiasis manifests as superficial mucocutaneous infections, chronic mucocutaneous candidiasis, or systemic infection. Superficial mucocutaneous infections can occur in any area of skin or mucus membrane. Thrush, commonly seen in AIDS patients, is characterized by a patchy or continuous, creamy to gray pseudomembrane that covers the tongue, mouth, or other oropharyngeal surfaces and may be accompanied by ulceration and necrosis. Laryngeal involvement results in hoarseness. Esophagitis is often an extension of oropharyngeal disease and may manifest with symptoms of retrostemal pain and dysphagia. Intestinal candidiasis is commonly asymptomatic, but is a major source of hematogenous invasion in immunocompromised individuals. Intertrigo involves the axillae, groins, inframammary folds, and other warm, moist areas, and may manifest as red, oozing or dry, scaly lesions. Infections may occur in other areas, including perianal and genital areas. Paronychia, infection of the nails, often follows chronic exposure of the hands or feet to moisture. Some patients with limited T-cell immunodeficiency develop chronic mucocutaneous candidiasis. These patients suffer from persistent superficial Candida infection of the skin, scalp, nails and mucus membranes.

Most cases of systemic candidiasis are caused by *Candida albicans* and *C. tropicalis*, and increasingly, *C. glabrata*. Clinical manifestations of Candida infection appear mainly in the eyes, kidneys and skin. In the eyes, there may be single or multiple raised, white, fluffy chorioretinal lesions. These lesions are a potential cause of blindness. Involvement of the kidneys includes diffuse abscesses, capillary necrosis and obstruction of the ureters. Infection may result in progressive renal insufficiency. Systemic Candida infection can also manifest as maculonodular skin lesions surrounded by a reddened area; these lesions have an appearance similar to acne but are a major clue to a potentially lethal disease. Other manifestations of systemic candidiasis may include osteomyelitis, arthritis, meningitis, and abscesses in the brain, heart, liver, spleen and thyroid. Involvement of the lungs is also common, but pulmonary lesions are usually too small to be seen on chest X-ray. Finally, Candida endocarditis can occur in patients receiving prolonged intravenous therapy or cardiac valve implants, or in intravenous drug abusers. Fungal lesions appear on the valves, and can embolize and occlude large blood vessels.

Superficial infections are diagnosed by microscopic examination of scrapings or swabs of infected lesions in the presence of 10% potassium hydroxide. Candida organisms can also be seen on gram stain. Endocarditis is diagnosed by blood cultures or demonstration of bulky valvular lesions on echocardiography. Systemic candidiasis may be difficult to diagnose because the presence of heavy colonization at the usual sites of infection indicates, but does not prove, that dissemination has occurred. The most reliable evidence of systemic candidiasis is biopsy demonstration of tissue invasion or recovery of yeast from fluid in a closed body cavity, such as cerebral spinal fluid, pleural or peritoneal fluid. Similarly, positive blood or urine or sputum cultures may indicate invasive disease or simply localized disease around indwelling devices, e.g., catheters or intravenous lines.

Mucocutaneous infections may be treated with topical preparations of nystatin, amphotericin B, clotrimazole, miconazole, haloprogin or gentian violet. Oropharyngeal or esophageal candidiasis can be treated with systemic agents such as ketoconazole or fluconazole. Chronic mucocutaneous candidiasis syndrome may respond to topical or systemic therapeutic agents such as amphotericin B or ketoconazole, but often relapses when medication is discontinued. Cystitis may be treated with amphotericin B bladder rinses, or a brief low-dose intravenous course of amphotericin B with or without oral flucytosine. Endocarditis is essentially incurable without valve replacement, accompanied by a 6 to 10 week course of amphotericin B and flucytosine. Even with therapy, however, complete cure of endocarditis is not always possible.

The mortality rate from systemic candidiasis is about 50%. Systemic candidiasis may be treated with fluconazole, a fungistatic agent, or amphotericin B, a fungicidal agent although systemic use of the latter is limited by its toxicity. Both, drugs have substantial adverse reactions when used in combination with cyclosporine A, which itself can be nephrotoxic. The removal of precipitating factors such as intravenous lines or catheters is also important for controlling infection. Flucytosine therapy can be added to the amphotericin B therapy for treatment of systemic candidiasis, especially in patients that are not immunocompromised. In immunocompromised patients, however, these infections are problematic and resist effective treatment. Mortality with systemic candidiasis can be over 90% in such patients. Furthermore, chronic mucocutaneous candidiasis and candidal endocarditis often show evidence of disease after having been declared cured.

There continues to exist a need in the art for new anti-fungal methods and materials. In particular, effective anti-fungal therapy for systemic mycoses is limited. Products and methods responsive to this need would ideally involve substantially non-toxic compounds available in large quantities by means of synthetic or recombinant methods. Ideal compounds would have a rapid effect and a broad spectrum of fungicidal or fungistatic activity against a variety of different fungal species when administered or applied as the sole anti-fungal agent. Ideal compounds would also be useful in combinative therapies with other anti-fungal agents, particularly where these activities would reduce the amount of anti-fungal agent required for therapeutic effectiveness, enhance the effect of such agents, or limit potential toxic responses and high cost of treatment.

SUMMARY OF THE INVENTION

The present invention provides novel peptides derived from or based on Domain m (amino acids 142–169) of bactericidal/permeability-increasing protein (BPI) and therapeutic uses of such peptides as anti-fungal agents. Peptides of the invention are useful in methods of treating a subject suffering from a fungal infection by administering a therapeutically effective amount of the peptide. This is based on the surprising discovery that Domain III derived peptides have fungicidal/fungistatic effects. A second surprising discovery is that such peptides have LPS-neutralizing activity. This activity provides an additional benefit in the use of peptides of the invention for treating fungal infections. Domain m derived peptides may be administered alone or in conjunction with known anti-fungal agents. When made the subject of adjunctive therapy, the administration of Domain m derived peptides may reduce the amount of anti-fungal agent needed for effective therapy, thus limiting potential toxic response and/or high cost of treatment. Administration of Domain III derived peptides may also enhance the effect of such agents, accelerate the effect of such agents, or reverse resistance of fungi to such agents. Peptides according to the invention include peptides SEQ ID NOS: 1–250.

In addition, the invention provides a method of killing or inhibiting growth of fungi comprising contacting the fungi with a Domain III derived peptide. This method can be practiced in vivo or in a variety of in vitro uses such as to decontaminate fluids and surfaces and to sterilize surgical and other medical equipment and implantable devices, including prosthetic joints and indwelling invasive devices.

A further aspect of the invention involves use of a Domain III derived peptide for the manufacture of a medicament for treatment of fungal infection. The medicament may include, in addition to a Domain III derived peptide, other chemotherapeutic agents such as anti-fungal agents.

Numerous additional aspects and advantages of the invention will become apparent to those skilled in the art upon considering the following detailed description of the invention, which describes the presently preferred embodiments thereof.

DETAILED DESCRIPTION OF THE INVENTION

Figure 1:
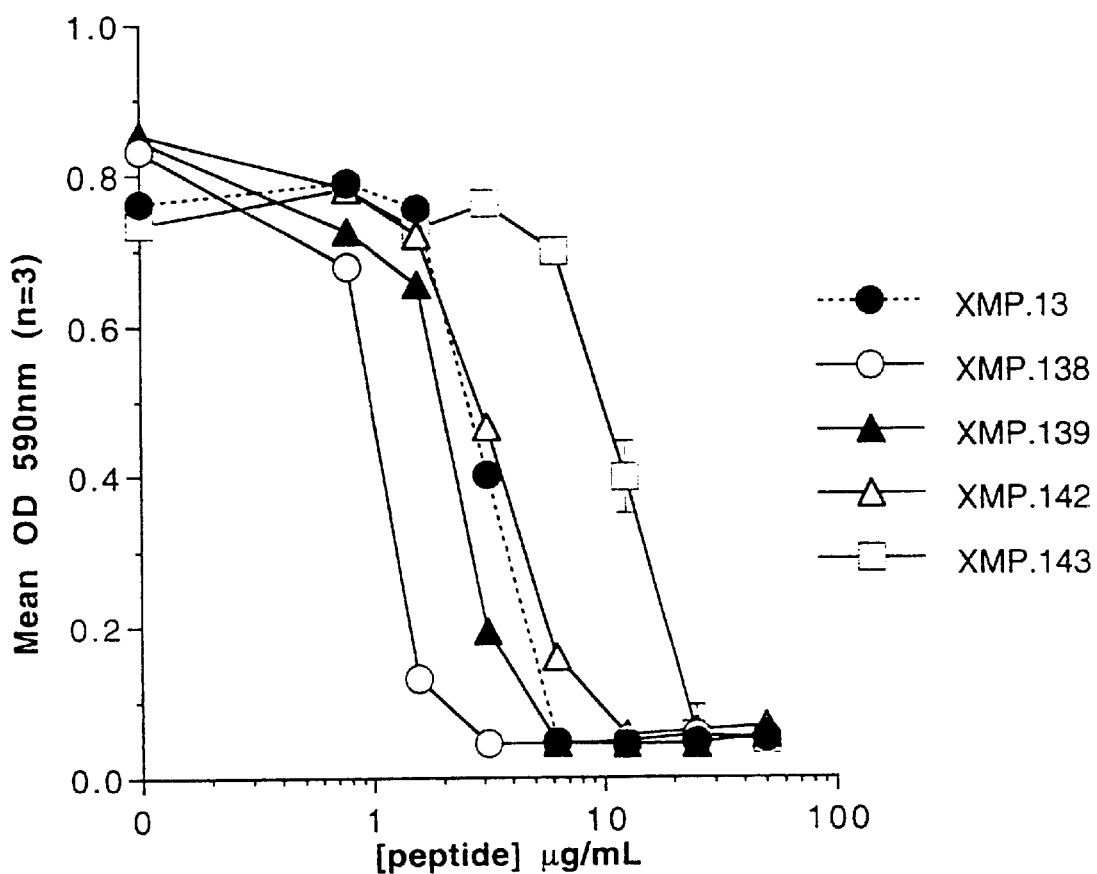
FIG. 1 provides results of broth assay tests of the activity of various peptides against *C. albicans*.

The present invention relates to the surprising discovery that a Domain III derived peptide has fungicidal activity and can be administered to treat subjects suffering from fungal infection. As used herein, "subject" is meant to refer to higher organisms, including animals (e.g., humans; companion animals such as dogs; livestock such as horses, cows and pigs; poultry; insects; fish; avian species) and plants. Also provided are methods of treating fungal infections with such peptides. Unexpectedly, Domain III derived peptides were demonstrated to have anti-fungal activities both in vitro killing assays and in in vivo models of fungal infection, as measured, for example, by improved survival or reduction of colony-forming units in circulation after fungal challenge. A variety of fungal infections, including infections caused by Aspergillus, infections caused by Cryptococcus, such as cryptococcal meningitis, and mucocutaneous and systemic candidiasis caused by Candida species, may be treated according to the invention. Also, unexpectedly, Domain III derived peptides were demonstrated to have LPS-neutralizing activity both in an in vitro assay and an in vivo model. This activity provides an additional benefit in the treatment of fungal infections where bacterial LPS from translocation or additional infection is associated with the fungal infection.

As used herein "Domain III derived peptide" includes peptides having an amino acid sequence of BPI protein from about position 142 to about position 169, subsequences thereof and variants of the sequence or subsequence thereof, which posses antifungal activity. Specifically included are those antifungal peptides having six to fourteen amino acids and having the amino acid sequence of BPI protein from about position 148 to about position 161, subsequences thereof and variants of the sequence or subsequence. amino acid sequence of BPI protein from about position 148 to about position 161, subsequences thereof and variants of the sequence or subsequence. Certain preferred peptides have fourteen amino acids and among the preferred variant sequences and subsequences are those having K as an amino acid corresponding to G at position 152. Preferred peptide sequences with fourteen amino acids have a core amino acid sequence selected from the group consisting of LIQL, IQLF, WLIQL, LIQLF and WLIQLF or a variant core amino acid sequence having at least 75% homology to said core amino acid sequence and include the peptides of SEQ ID NOS: 4 (XMP.13), 6–19 (XMP.31–44), 21–22 (XMP.82–83), 23–25 (XMP.85–87), 26–27 (XMP.91–92), 28–31 (XMP.94–97), 32–33 (XMP.100–101), 34 (XMP.104), 35–40 (XMP.106–111), 41 (XMP.113), 42 (XMP.116), 43–55 (XMP.123–135), 57–58 (XMP.138–139), 59–61 (XMP.142–144), 62 (XMP.146), 66–78 (XMP.222–234), 80–88 (XMP.236–244), 89–109 (XMP.249–269) and 116 (XMP.283). This group of antifungal 14 mer peptides includes variant sequence peptides wherein at least one BPI sequence residue has been replaced by a D-isomer amino acid. See, e.g., SEQ ID NOS: 46(XMP.126), 48 (XMP.128), 86–87 (XMP.242–243) and 92–93 (XMP.252–253). Variants involving BPI sequence replacements by atypical amino acids such as β(1-naphthyl)A, β(2-naphthyl)A, para-amino F, cyclohexyl A, α- and γ-aminobutyric acids, α methyl A and N-methyl G, V and L are also included within this group.

Among the presently preferred Domain III derived antifungal peptides of the invention having from seven to twelve amino acids comprising: (a) a core sequence of amino acids selected from the group consisting of LIQL, IQLF, WLIQL, LIQLF and WLIQLF; and (b) one or more cationic amino acids selected from the group consisting of K, R, H, ornithine and diaminobutyric acid at the amino and/or carboxy terminal portion of the core sequence. A subset of peptides have from seven to nine amino acids comprising: (a) a core sequence of amino acids selected from the group consisting of LIQL and IQLF; and (b) at least two cationic amino acids selected from the group consisting of K, R, H, ornithine and diaminobutyric acid at the amino and/or carboxy terminal portion of the core sequence. Another subset of peptides has from eight to ten amino acids comprising: (a) a core sequence of amino acids selected from the group consisting of LIQLF and WLIQLF; and (b) at least two cationic amino acids selected from the group consisting of K, R, H, ornithine and diaminobutyric acid at the amino and/or carboxy terminal portion of the core sequence. Still another subset of peptides has nine to twelve amino acids comprising: (a) a core sequence of amino acids selected from the group consisting of WLIQLF; and (b) at least three cationic amino acids selected from the group consisting of K, R, H, ornithine and diaminobutyric acid at the amino and/or carboxy terminal portion of the core sequence. Illustrating these subsets are the peptides of SEQ ID NOS: 118–137 (XMP.285–304), 140–144 (XMP.307–311), 155–160 (XMP.322–327), 166–170 (XMP.335–339), 174–177 (XMP.343–346), 179–184 (XMP.348–353), 186 (XMP.355), 188–190 (XMP.357–359).

It will be apparent from consideration of the structures of the above-described peptides that the Domain III sequence of BPI amino acids from 148 to 161 includes the core sequence(s) noted above as well as multiple cationic residues (K and H) flanking the core. This motif is carried forward in the structures of subsequences of the 148 to 161 sequence providing antifungal peptides of the invention and also preserved in antifungal variants of the 148 to 161 sequence and subsequences thereof. Note, for example that when the G residue normally in the BPI sequence at position 152 is replaced by K, this replacement serves to provide a cationic residue immediately adjacent to the predominantly hydrophobic core residues. Sequence and subsequence variants providing antifungal peptides according to the invention thus include those peptides wherein one or more existing non-cationic residues ordinarily flanking the core sequence (s) are replaced by cationic residues. 158) are replaceable by a different aromatic amino acid residues or by neutral aliphatic residues G, A, V, I and L. Moreover, the core sequence Q (BPI residue 156) is replaceable preferably by a neutral hydrophilic amino acid T. S and N. As noted above, where variations are introduced into core subsequence(s), it is preferable that the variant core sequence(s) retain 75% homology to the sequences occurring in BPI.

Antifungal Domain III peptides of the invention have one or more D-isomer amino acids, as illustrated by the peptides of SEQ ID NOS: 164 (XMP.333), 165 (XMP.334), 173 (XMP.342), 194 (XMP.363) and 196 (XMP.365) and have the core sequence amino acids comprise D-isomer amino acids in reverse sequence order as illustrated by peptides having the amino acid sequence set out in SEQ ID NOS: 163 (XMP.332) and 198 (XMP.367). The antifungal peptides can have an acetylated amino terminal amino acid residue as illustrated by the peptides of SEQ ID NOS: 162 (XMP.331), 185 (XMP.354), 187 (XMP.356), 195 (XMP.364), 199 (XMP.368) and 204 (XMP.373). Cyclic antifungal peptides as illustrated by SEQ ID NOS: 191–193 (XMP.360–362) are also within the scope of the invention.

Additional Domain III antifungal peptides of the invention include antifungal peptides SEQ ID NOS: 1 (XMP.5), 2–4 (XMP.11–13), 5 (XMP.29), 20 (XMP.55), 56 (XMP.137), 79 (XMP.235), 111–115 (XMP.271–275), 117 (XMP.284), 132 (XMP.299), 138–139 (XMP.305–306), 145–154 (XMP.312–321), 200–203 (XMP.369–372), 171–172 (XMP.340–341) and BPI residues 145–159 and 149–163 of SEQ ID NO:206.

Additional Domain III antifungal peptides of the invention include antifungal peptides SEQ ID NOS:205–243 (XMP.374–412) and SEQ ID NOS:244–250 (XMP.414–420). Thus, peptides of the invention include peptides that have SEQ ID NOS: 1–250 as shown in Table 1 herein.

Pharmaceutical compositions of the invention comprise a Domain III derived peptide and a pharmaceutically acceptable diluent, adjuvant or carrier and are administered topically, intravenously, orally or as an aerosol.

In vitro methods of the invention permit killing or inhibiting replication of fungi through contacting the fungi with an antifungal peptide or pharmaceutical composition containing the same. Fungal infection treatment methods of the invention comprise administering to a subject suffering from a fungal infection a therapeutically effective amount of a Domain III antifungal peptide and such treatment methods are applicable to infections by fungal infection involves a fungal species selected from the group consisting of Candida (especially, *C. albicans, C. glabrata, C. krusei, C. lusitaniae, C. parapsilosis* and *C. tropicalis*), Aspergillus and Cryptococcus species.

As described in detail medicaments/pharmaceutical compositions developed according to the invention can include other antifungal agents including non-peptide agents or can be used in combinative therapeutic methods with other such agents.

Peptides derived from or based on BPI produced by recombinant or synthetic means (BPI-derived peptides) have been described in co-owned and copending PCT Application No. US94/10427 filed Sep. 15, 1994, which corresponds to U.S. patent application Ser. No. 08/306,473, filed Sep. 15, 1994. and PCT Application No. US94/02465 filed Mar. 11, 1994, which corresponds to U.S. patent application Ser. No. 08/209,762, filed Mar. 11, 1994, which is a continuation-in-part of U.S. patent application Ser. No. 08/183,222, filed Jan. 14, 1994, which is a continuation-in-part of U.S. patent application Ser. No. 08/093,202 filed Jul. 15, 1993 (for which the corresponding international application is PCT Application No. US94/02401 filed Mar. 11, 1994), which is a continuation-in-part of U.S. patent application Ser. No. 08/030,644 filed Mar. 12, 1993 (disclosing, inmer aila, overlapping 15-mer peptides having BPI residues 145-159 and 149–163 of SEQ ID NO. 206), the disclosures of all of which are incorporated herein by reference. BPI-derived peptides having an amino acid sequence of BPI protein from about position 142 to about position 169, subsequences thereof and variants of the sequence or subsequence thereof, which possess a BPI anti-fungal biological activity, were disclosed in co-owned and co-pending U.S. priority application Ser. No. 08/372,105 filed Jan. 13, 1995, the disclosure of which is incorporated herein by reference.

The Domain III derived peptide may be administered systemically or topically. Systemic routes of administration include oral, intravenous, intramuscular or subcutaneous injection (including into depots for long-term release), intraocular or retrobulbar, intrathecal, intraperitoneal (e.g. by intraperitoneal lavage), transpulmonary using aerosolized or nebulized drug, or transdermal. Topical routes include administration in the form of salves, ophthalmic drops, ear drops, or irrigation fluids (for, e.g., irrigation of wounds).

The Domain III derived peptide may be administered in conjunction with other anti-fungal agents. Preferred antifungal agents for this purpose are amphotericin B and fluconazole. Concurrent administration of Domain III derived peptide with anti-fungal agents is expected to improve the therapeutic effectiveness of the anti-fungal agents. This may occur through reducing the concentration of anti-fungal agent required to eradicate or inhibit fungal growth, e.g., replication. Because the use of some agents is limited by their systemic toxicity or prohibitive cost, lowering the concentration of anti-fungal agent required for therapeutic effectiveness reduces toxicity and/or cost of treatment, and thus allows wider use of the agent. Concurrent administration of Domain III derived peptide and another anti-fungal agent may produce a more rapid or complete fungicidal/fungistatic effect than could be achieved with either agent alone. Domain III derived peptide administration may reverse the resistance of fungi to anti-fungal agents. Domain III derived peptide administration may also convert a fungistatic agent into a fungicidal agent.

An advantage provided by the present invention is the ability to treat fungal infections, particularly Candida infections, that are presently considered incurable. Another advantage is the ability to treat fungi that have acquired resistance to known anti-fungal agents. A further advantage of concurrent administration of Domain III derived peptide with an anti-fungal agent having undesirable side effects, e.g., amphotericin B, is the ability to reduce the amount of anti-fungal agent needed for effective therapy. The present invention may also provide quality of life benefits due to, e.g., decreased duration of therapy, reduced stay in intensive care units or reduced stay overall in the hospital, with the concomitant reduced risk of serious nosocomial (hospital-acquired) infections.

"Concurrent administration" as used herein includes administration of the agents together, simultaneously or before or after each other. The Domain III derived peptide and anti-fungal agents may be administered by different routes. For example, the Domain III derived peptide may be administered intravenously while the anti-fungal agents are administered intramuscularly, intravenously, subcutaneously, orally or intraperitoneally. Alternatively, the Domain III derived peptide may be administered intraperitoneally while the anti-fungal agents are administered intraperitoneally or intravenously, or the Domain III derived peptide may be administered in an aerosolized or nebulized form while the anti-fungal agents are administered, e.g., intravenously. The Domain III derived peptide and anti-fungal agents may be both administered intravenously. The Domain III derived peptide and anti-fungal agents may be given sequentially in the same intravenous line, after an intermediate flush, or may be given in different intravenous lines. The Domain III derived peptide and anti-fungal agents may be administered simultaneously or sequentially, as long as they are given in a manner sufficient to allow both agents to achieve effective concentrations at the site of infection.

Concurrent administration of Domain III derived peptide and another anti-fungal agent is expected to provide more effective treatment of fungal infections. Concurrent administration of the two agents may provide greater therapeutic effects in vivo than either agent provides when administered singly. For example, concurrent administration may permit a reduction in the dosage of one or both agents with achievement of a similar therapeutic effect. Alternatively, the concurrent administration may produce a more rapid or complete fungicidal/fungistatic effect than could be achieved with either agent alone.

Therapeutic effectiveness is based on a successful clinical outcome, and does not require that the anti-fungal agent or agents kill 100% of the organisms involved in the infection. Success depends on achieving a level of anti-fungal activity at the site of infection that is sufficient to inhibit the fungi in a manner that tips the balance in favor of the host. When host defenses are maximally effective, the anti-fungal effect required may be minimal. Reducing organism load by even one log (a factor of 10) may permit the host's own defenses to control the infection. In addition, augmenting an early fungicidal/fungistatic effect can be more important than long-term fungicidal/fungistatic effect. These early events are a significant and critical part of therapeutic success, because they allow time for host defense mechanisms to activate.

A Domain III derived peptide may interact with a variety of host defense elements present in whole blood or serum, including complement, p15 and LBP, and other cells and components of the immune system. Such interactions may result in potentiation of the activities of the peptide. Because of these interactions, Domain III derived peptides can be expected to exert even greater activity in vivo than in vitro. Thus, while in vitro tests are predictive of in vivo utility, absence of activity in vitro does not necessarily indicate absence of activity in vivo. For example, BPI has been observed to display a greater bactericidal effect on gram-negative bacteria in whole blood or plasma assays than in assays using conventional media. [Weiss et al., *J. Clin. Invest.* 90:1122–1130 (1992)]. This may be because conventional in vitro systems lack the blood elements that facilitate or potentiate BPI's function in vivo, or because conventional media contain higher than physiological concentrations of magnesium and calcium, which are typically inhibitors of the activity of BPI protein products. Furthermore, in the host, Domain III derived peptides are available to neutralize translocation of gram-negative bacteria and concomitant release of endotoxin, a further clinical benefit not seen in or predicted by in virro tests of anti-fungal activity.

It is also contemplated that the Domain III derived peptides be administered with other products that potentiate the activity of the peptide, including the anti-fungal activity of the peptides. For example, serum complement potentiates the gram-negative bactericidal activity of BPI protein products; the combination of BPI protein product and serum complement provides synergistic bactericidal/growth inhibitory effects. See, e.g., Ooi et al. *J. Biol. Chem.*, 265: 15956 (1990) and Levy et al. *J. Biol. Chem.*, 268:6038–6083 (1993) which address naturally-occuring 15 kD proteins potentiating BPI antibacterial activity. See also co-owned, co-pending PCT Application No. US94/07834 filed Jul. 13, 1994, which corresponds to U.S. patent application Ser. No. 08/274,303 filed Jul. 11, 1994 as a continuation-in-part of U.S. patent application Ser. No. 08/093,201 filed Jul. 14, 1993. These applications, which are all incorporated herein by reference, describe methods for potentiating gram-negative bactericidal activity of BPI protein products by administering lipopolysaccharide binding protein (LBP) and LBP protein products. LBP protein derivatives and derivative hybrids which lack CD-14 immunostimulatory properties are described in PCT Application No. US94/06931 filed Jun. 17, 1994; which corresponds to co-owned, co-pending U.S. patent application Ser. No. 08/261,660, filed Jun. 17, 1994 as a continuation-in-part of U.S. patent application Ser. No. 08/079,510, filed Jun. 17, 1993, the disclosures of all of which are hereby incorporated by reference. It has also been observed that poloxamer surfactants enhance the antibacterial activity of BPI protein products, as, described in Lambert, U.S. application Ser. No. 081372, 104 filed Jan. 13, 1995; poloxamer surfactants may also enhance the activity of anti-fungal agents.

Without being bound by a theory of the invention, it is believed that Domain III derived peptides may have several modes of action. The peptide, through its heparin-binding ability, may interfere with the binding of fungi to the extracellular matrix. For example, heparin-like surface molecules of Candida are believed to mediate adhesion of the yeast to extracellular matrix and host tissues. The peptide may also act directly on the cytoplasmic membrane of fungi. In addition, the peptide may bind to fungal cell wall mannoproteins that are structurally similar to the LPS of gram-negative organisms or that are responsible for adherence to target host tissues, thus interfering with fungal interaction with host tissues. Binding to fungal mannans may also promote access of the peptide to the inner cytoplasmic membrane. In addition, because fungal infection may cause stress-induced translocation of bowel flora and/or LPS, the peptide may also act beneficially by killing gram-negative bacteria and neutralizing LPS. Finally, the antifungal activity of Domain III peptides according to the invention may result from unique structural features. For example, a six amino acid sequence within Domain III (WLIQLF) and the included five and four amino acid sequences (LIQL, IQLF, WLQL and LIQLF) are composed of hydrophobic amino acids with the exception of glutamine (Q) that is a neutral hydrophilic amino acid. This hydrophobic stretch is bounded by highly cationic (polar) lysines on the N- and C-termini. This motif is reminiscent of leader/signal peptides as well as transmembrane segments of membrane proteins. Aliphatic amino acids such as I, L, V, M, A, have a high propensity to form transmembrane c-helical structures within the hydrophobic membrane environment when found in sequences of 12–15 nonpolar amino acids due to their ability to form backbone hydrogen bonds. Aromatic hydrophobic amino acids such as W and F can also incorporate into a membrane α-helix. The neutral, hydrophilic glutamine in the middle of a Domain III hydrophobic stretch may participate in hydrogen bonding with other fungal membrane components such as ergosterol and thus play an important role in the fungicidal activity. A short 10 amino acid peptide (e.g., XMP.293) is not expected to be long enough to span a lipid bilayer and probably has a much different mechanism of action than a membrane disrupting, amphipathic type of cationic antimicrobial peptide. The short motif of six to twelve amino acid peptides with a core of neutral amino acids bounded by cationic amino acids is not long enough to span a fungal lipid bilayer and thus may be allowed to traverse the membrane bilayer more efficiently than longer peptides. If transported inside the cell, the cationic/neutrallcationic molecules may inhibit the function of endogenous polyamines (spermidine, spermine, putrescine) by either competitive inhibition of the polyamine regulation of cell wall carbohydrate synthesis and/or by feedback inhibition of polyamine synthesis.

In addition, the invention provides a method of killing or inhibiting growth of fungi comprising contacting the fungi with a Domain III derived peptide. This method can be practiced in vivo or in a variety of in vitro uses such as use in food preparations or to decontaminate fluids and surfaces or to sterilize surgical and other medical equipment and implantable devices, including prosthetic joints. These methods can also be used for in situ sterilization of indwelling invasive devices such as intravenous lines and catheters, which are often foci of infection.

A further aspect of the invention involves use of a Domain III derived peptide for the manufacture of a medicament for treatment of fungal infection. The medicament may include, in addition to a BPI protein product, other chemotherapeutic agents such as anti-fungal agents. The medicament can optionally comprise a pharmaceutically acceptable diluent, adjuvant or carrier.

The administration of antifungal peptides is suitably accomplished with a pharmaceutical composition comprising a peptide and a pharmaceutically acceptable diluent, adjuvant, or carrier. The peptide may be administered without or in conjunction with known surfactants, other chemotherapeutic agents or additional known anti-fungal agents.

Other aspects and advantages of the present invention will be understood upon consideration of the following illustrative examples wherein Example 1 addresses peptide preparation and purification; Example 2 addresses in vitro antifungal testing of peptides; Example 3 addresses additional in vitro and in vivo testing of the anti-fungal effect of peptides on a variety of fungal species, including Candida strains and antibiotic resistant strains; Example 4 addresses the in vivo effect of peptides on survival of mice challenged with Candida; Example 5 addresses the serum stability of peptides; Example 6 addresses the design and assay of anti-fungal peptides for structural motif and minimum functional sequence analysis; Example 7 addresses LPS neutralization activities of anti-fungal peptides; and Example 8 addresses peptide formulations.

EXAMPLE 1

Peptide Preparation and Purification

This example addresses the preparation and purification of Domain III derived peptides.

Peptides may be prepared according to a variety of synthetic procedures. Some peptides (e.g., XMP.5) were prepared by solid phase peptide synthesis as described in parent U.S. patent application Ser. Nos. 08/209,762 and 08/183,222 according to the methods of Merrifield, *J. Am Chem. Soc.* 85: 2149 (1963) and Merrifield et al. *Anal. Chem.*, 38: 1905–1914 (1966) using an Applied Biosystems, Inc. Model 432 peptide synthesizer.

Alternatively, peptides were synthesized on a larger scale using solid phase peptide synthesis on an Advanced Chemtech (ACT-Model 357 MPS) synthesizer utilizing a 1-Fluorenylmethyl-oxycarbonyl (Fmoc) protection strategy with a double coupling procedure employing N,N-diisopropylcarbodiimide (DIC)/1-hydroxybenzotrazole (HOBt) and 2-(1-H-benzotriazol-1-yl)-1,1,3,3,-tetramethyluronium hexa-fluorophosphate (HBTU)/HOBt/ diisopropylethylamine (DIEA). The solid support used was a polystyrene resin with 1% divinylbenzene (DVB) cross-linking and an 4-(2',4'-dimethoxyphenyl-Fmoc-aminomethyl)-phenoxy (Fmoc-Rink amide) linker with a substitution rate of 0.44 mmoles/gram. The scale used was between 0.1 grams and 5 grams of starting resin.

Dimethylformamide (DMF) was the primary solvent with a 50/50 solution of piperidine/DMF used for Fmoc deprotection in three consecutive treatments of 1, 5, and 10 minutes, respectively. A double coupling procedure was used in each cycle with a 4:1 amino acid to peptide ratio used in each coupling. The amino acids were dissolved in a 0.5M HOBt solution in N-methylpyrrolidinone (NMP) at a concentration also of 0.5M. For the first coupling, an equimolar (to amino acid) amount of a 0.5M solution of diisopropyl-carbodiimide (DIPCDI) in NMP was used and allowed to react for 45 minutes. The second coupling utilized an equimolar (to amino acid) volume of a 0.5M HBTU solution in DMF with an equal volume of a 1M DIEA solution in NMP (2:1, DIEA:amino acid) for a period of 30 minutes.

Upon completion of the synthesis, the resin was treated with MeOH, dried under vacuum, and then cleaved using a cocktail composed of trifluoroacetic acid (TFA) :thioanisole:ethanedithiol EDT):water, at a ratio of 36:2:1:1 (volume was dependent on the amount of resin) for a minimum of 2 hours with an additional 30 minutes added for each arginine (but not exceeding 3 hours) with the first 15 minutes occurring in a wet ice bath. The solutions were then dissolved in a 10% TFA in water solution, washed 3 times with methyl t-butyl ether (MTBE) and lyophilized.

The amino termini of selected peptides were acetylated after synthesis on solid phase using an N-terminal Fmoc protection strategy as described above. Subsequent to Fmoc removal with piperidine and prior to peptide cleavage with TFA, the peptide on the resin was derivatized with a 10-fold molar excess of acetic anhydride with a 2-fold molar excess of diisopropylethylamine in dimethylformamide for one hour or a double coupling procedure employing N,N-diisopropylcarbodiimide (DIC)/1-hydroxybenzotriazole (HOBt) and 2-(1-H-benzotriazol-1-yl)-1,1,3,3,-tetramethyluronium hexa-fluorophosphate (HBTU)/HOBt/ diisopropylethylamine (DIEA) and one of the following building blocks was used for derivatization: caprylic acid, lauric acid, Fmoc-8-amino-ctonoic acid and FMoc-12-amino-dodecanoic acid. The peptide was then cleaved from the resin with the TFA cleavage cocktail as described above and purified as described below. N-terminal acacylation of the purified peptide was verified by mass spectrometry.

For purity analysis of each newly synthesized peptide, dilute solutions of crude lyophilized peptides were prepared and analyzed on a Michrom Ultrafast Microprotein Analyzer equipped with a 150 mm×1 mm, 5 μparticle, 300 Å pore C-8 Zorbax column. The column oven was set to 40° C., the flow rate was 100 μL/minute, and injection volumes were typically 5–10 μL. HPLC was performed using 5% acetonitrile/ 0.1% TFA in water as mobile phase A, and 80% acetonitrile/ 0.065% TFA as mobile phase B. The eluate was monitored spectrophotometrically at 214 nm. Percent purity is calculated from the peak area of the individual peptides (see Table 1).

Selected peptides were purified by high performance liquid chromatography (HPLC), using a Waters Prep LC 2000 Preparative Chromatography System (Water Corp., Milford, Mass.) equipped with a Delta Pak C-18, 15 μm, 300 Å cartridge column consisting of a 40×10 mm guard cartridge and a 40×100 mm Prep Pak cartridge. The column was equilibrated in 25% buffer B, where A=5% acetonitrile/ 0.1% trifluoroacetic acid and B=80% acetonitrile/0.065% trifluoroacetic acid. Peptides were dissolved to ~20 mg/mL in buffer A and 200–800 mg were applied to the column through the LC pump operating at a flow rate of 8–17 mL/minute bound material was eluted with a gradient of 25–35% buffer B/30 min applied at 8–17 mL/minute. (Some peptides were purified with a gradient of 23–33%B/30 minute). The eluate was monitored at 220 and/or 280 and 300 nm with a Waters 490E Programmable Multiwavelength Detector. Fractions were collected and assayed for the peptide of interest on an Ultrafast Micoprotein Analyzer (Michrom BioResources, Inc., Pleasanton, Calif.) equipped with a Zorbax C-8, 150×1 mm, 5 μm, 300 Å maintained at 40° C. Fractions containing the peptide of interest at ≧95% purity were pooled and lyophilized to dryness. The purity of the recovered material was determined with analytical reverse-phase HPLC.

EXAMPLE 2

In Vitro Anti-fungal Effects

This example addresses in vitro screening of Domain III derived peptides for anti-fungal activity in a broth assay and/or in a radial diffusion assay.

Table 1 below sets out peptides derived from or based on Domain III BPI sequences. Such peptides may be identified by peptide number with a prefix XMP or BPI (e.g., XMP.1 or BPI.1, XMP.2 or BPI.2, etc.). Table 1 also sets out the SEQ ID NO: of each peptide, the amino acid sequence based on reference to position within BPI and the designation of amino acid substitutions and additions. Also set out in Table 1 are HPLC estimates of purity of the peptides. The HPLC purity analysis was performed as described in Example 1.

In each broth assay screening procedure, a colony of C. albicans designated CA-1, Strain SLU-1 that was received from the laboratories of G. Matuschak and A. Lechner, St. Louis University Hospital, St. Louis, Mo., where the strain was maintained, was inoculated into a tube containing 5 mL Sabouraud Dextrose broth (2% dextrose, 1% neopeptone) and incubated overnight at 37° C. with shaking. The overnight culture was diluted 1:50 into 5 mL of fresh broth and incubated for 3 hours at 37° C. Organisms were pelleted by centrifugation in a Beckman J-6M centrifuge for 5 minutes at 3000 rpm (1500×g) and the pellets were resuspended in 5 mL phosphate buffered saline (PBS) and the optical density at 570 nm was determined. On the basis of the determination that one OD unit equals $3 \times 10^7$ colony forming units/mL, yeast cells were diluted to $2 \times 10^6$ cells/mL in Sabouraud Dextrose broth.

Domain III peptides derived from or based on BPI to be screened were originally constituted in Dulbecco's-PBS, were diluted to 100 μg/mL in broth and were serially diluted 2-fold into wells of a 96 well sterile, flat bottom, non-pyrogenic tissue culture plate (Costar, Cambridge, Mass.). All assays were performed in triplicate. $2 \times 10^5$ organisms were added at 100 μl per well; final volume was 200 μL/well; the plate was incubated on a shaker at 37° C. for 18 hours; and the optical densities for each well were read at 590 nm. FIG. 1 hereto graphically illustrates the dose response curves for five peptides (XMP.13, XMP.138, XMP.139, XMP.142 and XMP.143). All illustrated peptides reduced optical density of the cultures to below 0.1 at doses of less than about 50 μg/L, with XMP.138 displaying the best results of the illustrated peptides at low dosages. The broth assay data may be set out in terms of minimum inhibitory concentration (MIC), i.e. the lowest concentration required to reduce the optical density at 590 nm to below 0.1. The MIC (μg/mL) of each of the five peptides listed above in FIG. 1 is 12.5, 3.13, 6.25, 12.5 and 25.0, respectively.

In the radial diffusion assay procedures, the CA-1 cultures and peptide solutions were prepared as in the broth assay procedure described above. Ten mL of molten underlayer agarose comprising 3% Sabouraud Dextrose broth, 1% agarose (Pharmacia, Piscataway, N.J.), 0.02% Tween 20, and 10 mM sodium phosphate at pH 7.4, was added to polystyrene tubes and maintained in a 56° C. water bath until the addition of yeast. Tubes were cooled to approximately 45° C., yeast were added to give a final concentration of $1 \times 10^6$ CFU/mL, and the tubes were mixed again by inverting. The contents were poured into level square petri dishes and distributed evenly. The agarose solidified in less than 30 seconds and had a uniform thickness of about 1 mm. A series of wells were punched into the hardened agarose using a sterile 3 mm punch attached to a vacuum apparatus.

Peptides to be assayed were 2-fold serially diluted in Dulbecco's PBS (D-PBS) starting from a concentration of approximately 1 mg/mL. Five μL of each dilution were added to each well and the plates were incubated at 37° C. for 3 hours. An overlayer of 10 mL of molten agarose comprising 6% Sabouraud Dextrose broth, 1% agarose, and 10 mM sodium phosphate, pH 7.4, (at approximately 45° C.) was then added and plates were incubated overnight at 37° C. Following this overnight incubation, a dilute Coomassie solution was poured into the plates and allowed to stain for 24 hours.

Clear zones of growth inhibition around each well were measured with calipers. The actual area of growth inhibition (mm$^2$) was calculated by subtracting the area of the well. Table 1 below sets out the results of the radial diffusion assays for tested peptides in terms of the number of picomoles (pmol) of peptide required to establish a 30 mm$^2$ area of growth inhibition calculated by PROBIT analysis (e.g., calculated from regression of the linear portion of log-concentration dose-response curve, log pmol/well vs. net area of inhibition).

TABLE 1

| Peptide (SEQ ID NO:) | Peptide Amino Acid Segment | HPLC % Purity | C. albicans pmol/ 30 mm² zone[a] |
|---|---|---|---|
| XMP.5 (1) | 142–163 | 18 | >2151 |
| XMP.11 (2) | 148–151, 153–161 | 76 | 645 |
| XMP.12 (3) | 141–169 | 26 | >2099 |
| XMP.13 (4) | 148–161 | 69 | 541 |
| XMP.13P' (4) | 148–161 | 98 | 222 |
| XMP.29 (5) | (148–161) × 2 | 26 | >1469 |
| XMP.31 (6) | 148–161, A @ 148 (K) | 68 | 426 |
| XMP.32 (7) | 148–161, A @ 149 (S) | 70 | 294 |
| XMP.33 (8) | 148–161, A @ 150 (K) | 58 | 603 |
| XMP.34 (9) | 148–161, A @ 151 (V) | 51 | 319 |
| XMP.35 (10) | 148–161, A @ 152 (G) | 72 | 442 |
| XMP.36 (11) | 148–161, A @ 153 (W) | 64 | 197 |
| XMP.36 (11) | 148–161, A @ 153 (W) | 99 | 231 |
| XMP.37 (12) | 148–161, A @ 154 (L) | 51 | 253 |
| XMP.38 (13) | 148–161, A @ 155 (I) | 70 | 391 |
| XMP.39 (14) | 148–161, A @ 156 (Q) | 53 | 1792 |
| XMP.40 (15) | 148–161, A @ 157 (L) | 53 | 253 |
| XMP.41 (16) | 148–161, A @ 158 (F) | 63 | 734 |
| XMP.42 (17) | 148–161, A @ 159 (R) | 59 | 548 |
| XMP.43 (18) | 148–161, A @ 160 (K) | 53 | 785 |
| XMP.44 (19) | 148–161, A @ 161 (K) | 70 | 578 |
| XMP.55 (20) | 152–172 | 28 | >2666 |
| XMP.82 (21) | 148–161, W @ 158 (P) | 58 | 518 |
| XMP 83 (22) | 148–161, β(1-naphthyl)-A @ 153 (W) | 63 | 1804 |
| XMP.85 (23) | 148–161, L @ 152 (G) | 74 | >1881 |
| XMP.86 (24) | 148–161, L @ 156 (Q) | 51 | >2048 |
| XMP.87 (25) | 148–161, L @ 159 (H) | 63 | >1536 |
| XMP.91 (26) | 148–161, F @ 156 (Q) | 31 | >3844 |
| XMP.92 (27) | 148–161, K @ 156 (Q) | 50 | 299 |
| XMP.94 (28) | 148–161, F @ 159 (H) | 59 | >923 |
| XMP.95 (29) | 148–161, F @ 152 (G) | 57 | >1398 |
| XMP.96 (30) | 148–161, F @ 161 (K) | 60 | 1856 |
| XMP.97 (31) | 148–161, K @ 152 (G) | 67 | 213 |
| XMP.97P' (31) | 148–161, K @ 152 (G) | 98 | 303.5 |
| XMP.100 (32) | 148–161, K @ 152 (G) & 156 (Q) | 61 | 462 |
| XMP.101 (33) | (148–161) × 2[K @ 152(G) & 156 (Q), F @ 159 (H) & 161 (K)] | 16 | >1040 |
| XMP.104 (34) | 148–161, S @ 156 (Q) | 34 | >5569 |
| XMP.106 (35) | 148–161, T @ 156 (Q) | 26 | 1032 |
| XMP.107 (36) | 148–161, W @ 159 (H) | 55 | >2796 |
| XMP.108 (37) | 148–161, W @ 161 (K) | 50 | >3219 |
| XMP.109 (38) | 148–161, β(1-naphthyl)-A @ 158 (F) | 41 | >2839 |
| XMP.110 (39) | 148–161, β(1-naphthyl)-A @ 159 (H) | 56 | >2922 |
| XMP.111 (40) | 148–161, β(1-naphthyl)-A @ 161 (K) | 73 | >2809 |
| XMP.113 (41) | 148–161, F @ 157 (L) | 46 | 947 |
| XMP.116 (42) | 148–161, K @ 152 (G), β(1-naphthyl)-A @ 153 (W) | 72 | 670 |
| XMP.123 (43) | 148–161, p-Amino-F @ 156 (Q) | 64 | 1721 |
| XMP.124 (44) | 148–161, K @ 152(G), W @ 158 (P) | 67 | 351 |
| XMP.125 (45) | 148–161, Y @ 156 (Q) | 54 | >3150 |
| XMP.126 (46) | 148–161, $W_D$ @ 153 (W) | 54 | 1404 |
| XMP.127 (47) | 148–161, F @ 153 (W) | 63 | 226 |
| XMP.127P' (47) | 148–161, F @ 153 (W) | 94 | 935 |
| XMP.128 (48) | 148–161 $F_D$ @ 153(W) | 51 | 1179 |
| XMP.129 (49) | 148–161, β(1-naphthyl)$A_D$ @ 153 (W) | 28 | 2117 |
| XMP.130 (50) | 148–161, β(2-naphthyl)A @ 153 (W) | 80 | 1159 |
| XMP.131 (51) | 148–161, β(2-naphthyl)$A_D$ @ 153 (W) | 60 | 2493 |
| XMP.132 (52) | 148–161, PYR @ 153 (W) | 50 | 353 |
| XMP.133 (53) | 148–161, p-Amino-F @ 153 (W) | 47 | 284 |
| XMP.134 (54) | 148–161, p-Amino-F @ 152 (G) | 68 | 1255 |
| XMP.135 (55) | 148–161, K @ 153 (W) | 70 | 428 |
| XMP.137 (56) | C-148–161-C | 28 | >2286 |
| XMP.138 (57) | 148–161, K @ 152 (G), F @ 153 (W) | 61 | 257 |
| XMP.139 (58) | 148–161, Y @ 153 (W) | 60 | 323 |
| XMP.142 (59) | 148–161, W @ 157 (L) | 57 | 1244 |

TABLE 1-continued

| Peptide (SEQ ID NO:) | Peptide Amino Acid Segment | HPLC % Purity | *C. albicans* pmol/ 30 mm² zone[a] |
|---|---|---|---|
| XMP.143 (60) | 148–161, β(1-naphthyl)-A @ 157 (L) | 65 | >2839 |
| XMP.144 (61) | 148–161, Cyclohexyl-A @ 153 (W) | 60 | 695 |
| XMP.146 (62) | 148–161, β(1-naphthyl)-A @ 159 (H) & 161 (K) | 53 | b |
| XMP.148 (63) | 148–161, β(1-naphthyl)-A @ 153 (W) & 159 (H) | 62 | >2805 |
| XMP.161 (64) | 148–161, K @ 152 (G) & A @ 153 (W) | 75 | >2999 |
| XMP.166 (65) | 148–161, V @ 153 (W) | 68 | 171 |
| XMP.222 (66) | 148–161 β(1-naphthyl)-A @ 153 (W) & 161 (K) | 57 | >2,610 |
| XMP.222P' (66) | 148–161 β(1-naphthyl)-A @ 153 (W) & 161 (K) | >99 | NT |
| XMP.223 (67) | 148–161, β(1-naphthyl)-A @ 153 (W) & 157 (L) | 39 | b |
| XMP.224 (68) | 148–161, β(1-naphthyl)-A @ 153, p-amino-F @ 156 (Q) | 55 | >2,443 |
| XMP.225 (69) | 148–161, p-amino-F @ 152, β(1-naphthyl)-A @ 153 (W) | 77 | >2,506 |
| XMP.225P' (69) | 148–161, p-amino-F @ 152, β(1-naphthyl)-A @ 153 (W) | >99 | >2,736 |
| XMP.226 (70) | 148–161, β(1-naphthyl)-A @ 153, W @ 158 (F) | 50 | >2,597 |
| XMP.226P' (70) | 148–161, β(1-naphthyl)-A @ 153, W @ 158 (F) | 97 | >2,895 |
| XMP.227 (71) | 148–161, β(1-naphthyl)-A @ 157 (L) & 161 (K) | 54 | >2,365 |
| XMP.228 (72) | 148–161, p-amino-F @ 156 (Q), β(1-naphthyl)-A @ 161 (K) | 43 | b |
| XMP.229 (73) | 148–161, p-amino-F @ 152 (G), β(1-naphthyl)-A @ 161 (K) | 81 | b |
| XMP.230 (74) | 148–161, W @ 158 (F), β(1-naphthyl)-A @ 161 (K) | 5I | >2,386 |
| XMP.231 (75) | 148–161, β(1-naphthyl)-A @ 157 (L) & 159 (11) | 44 | b |
| XMP.232 (76) | 148–161, p-amino-F @ 156 (Q), β(1-naphthyl)-A @ 159 (H) | 28 | b |
| XMP.233 (77) | 148–161, p-amino-F @ 152 (G), β(1-naphthyl)-A @ (H) | 53 | b |
| XMP.234 (78) | 148–161, W @ 158 (F), β(1-naphthyl)-A @ 159 (H) | 26 | b |
| XMP.235 (79) | 148–161, p-amino-F @ 156 (Q), β(1-naphthyl)-A @ 157 (L) | 30 | b |
| XMP.236 (80) | 148–161, p-amino-F @ 152 (G), β(1-naphthyl)-A @ 157 (L) | 73 | >2,631 |
| XMP.237 (81) | 148–161, β(1-naphthyl)-A @ 157 (L), W @ 158 (P) | 34 | >2,777 |
| XMP.238 (82) | 148–161, p-amino-F @ 152 (G) & 156 (Q) | 66 | 2,702 |
| XMP.239 (83) | 148–161, p-amino-F @ 156 (Q), W @ 158 (F) | 30 | >2,802 |
| XMP.240 (84) | 148–161, p-amino-F @ 152 (G), W @ 158 (F) | 55 | >2,802 |
| XMP.241 (85) | 148–161, L @ 156 (Q), W @ 158 (F) | 55 | >2,161 |
| XMP.242 (86) | 148–161, β(2-naphthyl)A$_D$ @ 153 (W), L @ 156 (Q) | 52 | 359 |
| XMP.243 (87) | 148–161, β(2-naphthyl)A$_D$ @ 153 (W), W @ 158 (F) | Mixture | 716 |
| XMP.244 (88) | 148–161, β(2-naphthyl)A$_D$ @ 153 (W), L @ 156 (Q), W @ 158 (F) | 43 | 859 |
| XMP.249 (89) | 148–161, G @ 153 (W) | 46 | 1,242 |
| XMP.250 (90) | 148–161, L @ 153 (W) | 33 | 536 |
| XMP.251 (91) | 148–161, I @ 153 (W) | 44 | 1,289 |
| XMP.252 (92) | 148–161, A$_D$ @ 153 (W) | 52 | 1,613 |
| XMP.253 (93) | 148–161, V$_D$ @ 153 (W) | 51 | 1,108 |
| XMP.254 (94) | 148–161, β-A @ 153 (W) | 68 | 1,040 |
| XMP.255 (95) | 148–161, α-Aminobutyric Acid @ 153 (W) | 44 | 392 |
| XMP.255P' (95) | 148–161, α-Aminobutyric Acid @ 153 (W) | 94 | NT |
| XMP.256 (96) | 148–161, γ-Aminobutyric Acid @ 153 (W) | 38 | b |
| XMP.257 (97) | 148–161, α-Methyl-A @ 153 (W) | 44 | 1,321 |
| XMP.258 (98) | 148–161, t-Butyl-G @ 153 (W) | 62 | 880 |
| XMP.259 (99) | 148–161, N-Methyl-G @ 153 (W) | 88 | 2,117 |

TABLE 1-continued

| Peptide (SEQ ID NO:) | Peptide Amino Acid Segment | HPLC % Purity | *C. albicans* pmol/ 30 mm² zone[a] |
|---|---|---|---|
| XMP.260 (100) | 148–161, N-Methyl-V @ 153 (W) | 75 | 742 |
| XMP.261 (101) | 148–161, N-Methyl-L @ 153 (W) | 85 | 867 |
| XMP.262 (102) | 148–161, N @ 156 (Q) | 68 | 984 |
| XMP.263 (103) | 148–161, E @ 156 (Q) | 49 | 1,197 |
| XMP.264 (104) | 148–161, D @ 156 (Q) | 60 | 879 |
| XMP.265 (105) | 148–161, R @ 156 (Q) | 42 | 2,996 |
| XMP.266 (106) | 148–161, K @ 152 (G), V @ 153 (W) | 52 | 984 |
| XMP.267 (107) | 148–161, K @ 152 (G), A @ 154 (L) | 58 | 256 |
| XMP.267P' (107) | 148–161, K @ 152 (G), A@ 154 (L) | 97 | 106 |
| XMP.268 (108) | 148–161, V @ 153 (W), A @ 154 (L) | 62 | 308 |
| XMP.268P' (108) | 148–161, V @ 153 (W), A @ 154 (L) | 95 | 63 |
| XMP.269 (109) | 148–161, K @ 152 (G), V @ 153 (W), A 154 (L) | 30 | 635 |
| XMP.270 (110) | (148–161) + (148–161), L @ 1st 156 (Q) | 31 | >722 |
| XMP.271 (111) | (148–161) + (148–161), L @ 2nd 156 (Q) | 31 | >1,995 |
| XMP.272 (112) | (148–161) + (148–161), L @ both 156 (Q) | 32 | >2,599 |
| XMP.273 (113) | (148–161) + (148–161), F @ 1st 156 (Q) | 59 | >2,120 |
| XMP.274 (114) | (148–161) + (148–161), F @ 2nd 156 (Q) | 40 | >2,457 |
| XMP.275 (115) | (148–161) + (148–161), F @ both 156 (Q) | 34 | b |
| XMP.283 (116) | 148–161, K @ 152 (G), F @ 153 (W), K @ 156 (Q) | 36 | 1,336 |
| XMP.284 (117) | 149–161, K @ 152 (G) | 60 | 1,460 |
| XMP.284P' (117) | 149–161, K @ 152 (G) | 96 | 373 |
| XMP.285 (118) | 149–160, K @ 152 (G) | 75 | >3,024 |
| XMP.286 (119) | 150–161, K @ 152 (G) | 61 | 1,216 |
| XMP.286P' (119) | 150–161, K @ 152 (G) | 80 | 253 |
| XMP.287 (120) | 149–159, K @ 152 (G) | 58 | >3,509 |
| XMP.288 (121) | 150–160, K @ 152 (G) | 78 | >3,062 |
| XMP.288P' (121) | 150–160, K @ 152 (G) | 94 | 279 |
| XMP.289 (122) | 151–161, K @ 152 (G) | 78 | 1,542 |
| XMP.289P' (122) | 151–161, K @ 152 (G) | 94 | 658 |
| XMP.290 (123) | 149–158, K @ 152 (G) | 79 | >2,233 |
| XMP.291 (124) | 150–159, K @ 152 (G) | 55 | >5,039 |
| XMP.292 (125) | 151–160, K @ 152 (G) | 78 | >4,463 |
| XMP.293 (126) | 152–161, K @ 152 (G) | 78 | 1,156 |
| XMP.293P' (126) | 152–161, K @ 152 (G) | 95 | 215 |
| XMP.294 (127) | 149–157, K @ 152 (G) | 63 | >4,634 |
| XMP.295 (128) | 150–158, K @ 152 (G) | 82 | >1,977 |
| XMP.295P' (128) | 150–158, K @ 152 (G) | 98 | >2,612 |
| XMP.296 (129) | 151–159, K @ 152 (G) | 64 | >5,573 |
| XMP.297 (130) | 152–160 K @ 152 (G) | 81 | 1,817 |
| XMP.297P' (130) | 152–160 K @ 152 (G) | 97 | 564 |
| XMP.298 (131) | 153–161 | 84 | 2,628 |
| XMP.298P' (131) | 153–161 | 95 | 1,106 |
| XMP.299 (132) | 149–156, K @ 152 (G) | 68 | >8,768 |
| XMP.300 (133) | 150–157, K @ 152 (G) | 75 | 1,957 |
| XMP.300P' (133) | 150–157, K @ 152 (G) | 97 | 993 |
| XMP.301 (134) | 151–158, K @ 152 (G) | 41 | b |
| XMP.302 (135) | 152–159, K @ 152 (G) | 75 | >5,497 |
| XMP.302P' (135) | 152–159, K @ 152 (G) | 98 | 2,070 |
| XMP.303 (136) | 153–160 | 78 | >4,694 |
| XMP.303P' (136) | 153–160 | 98 | 1,307 |
| XMP.304 (137) | 154–161 | 84 | >8,290 |
| XMP.305 (138) | 149–155, K @ 152 (G) | 73 | >10,228 |
| XMP.306 (139) | 150–156, K @ 152 (G) | 62 | >10,485 |
| XMP.307 (140) | 151–157, K @ 152 (G) | 67 | >8,345 |
| XMP.308 (141) | 152–158, K @ 152 (G) | 72 | b |
| XMP.309 (142) | 153–159 | 76 | b |
| XMP.310 (143) | 154–160 | 56 | >9,475 |
| XMP.311 (144) | 155–161 | 77 | b |
| XMP.312 (145) | 149–154, K @ 152 (G) | 76 | >11,120 |
| XMP.313 (146) | 150–155, K @ 152 (G) | 59 | >11,050 |
| XMP.314 (147) | 151–156, K @ 152 (G) | 73 | >13,497 |
| XMP.315 (148) | 152–157, K @ 152 (G) | 84 | >5,069 |
| XMP.315P' (148) | 152–157, K @ 152 (G) | 94 | >12,853 |
| XMP.316 (149) | 153–158 | 85 | b |
| XMP.316P' (149) | 153–158 | 98 | g |
| XMP.317 (150) | 154–159 | 64 | b |
| XMP.318 (151) | 155–160 | 84 | b |
| XMP.319 (152) | 156–161 | 73 | b |
| XMP.320 (153) | 153–157 | 63 | >4,055 |
| XMP.321 (154) | 153–157 - K | 66 | >5,851 |
| XMP.322 (155) | 153–157 - K - K | 69 | 3,488 |

TABLE 1-continued

| Peptide (SEQ ID NO:) | Peptide Amino Acid Segment | HPLC % Purity | C. albicans pmol/ 30 mm² zone[a] |
|---|---|---|---|
| XMP.323 (156) | K - 153–157 - K | 63 | >4,627 |
| XMP.324 (157) | K - 153–157 - K - K | 67 | 894 |
| XMP.325 (158) | K - K - 153–157 | 66 | 4,135 |
| XMP.326 (159) | K - K - 153–157 - K | 59 | 2,182 |
| XMP.327 (160) | K - K - 153–157 - K - K | 75 | 353 |
| XMP.327P' (160) | K - K - 153–157 - K - K | 94 | 630 |
| XMP.330 (161) | 153–156 | 95 | b |
| XMP.331 (162) | † K - K - 153–157 - K - K | 66 | b |
| XMP.331P' (162) | † K - K - 153–157 - K - K | 97 | >3,493 |
| XMP.332 (163) | $K_D$ -$K_D$ - $L_D$ - $Q_D$ -$I_D$ -$L_D$ - $W_D$ - $K_D$ - $K_D$ | 64 | 356 |
| XMP.332P' (163) | $K_D$ -$K_D$ - $L_D$ - $Q_D$ -$I_D$ -$L_D$ - $W_D$ - $K_D$ - $K_D$ | 98 | 338 |
| XMP.333 (164) | $K_D$ - K - 153–157 - K - K | 62 | 673 |
| XMP.333P' (164) | $K_D$ - K - 153–157 - K - K | 98 | 361 |
| XMP.334 (165) | $P_D$ - K - 153–157 - K - K | 67 | 1,449 |
| XMP.334P' (165) | $P_D$ - K - 153–157 - K - K | 89 | 1,065 |
| XMP.335 (166) | P - K - 153–157 - K - K | 61 | 871 |
| XMP.335P' (166) | P - K - 153–157 - K - K | 98 | 1,353 |
| XMP.336 (167) | R - R - 153–157 - R - R | 22 | >7,332 |
| XMP.336P' (167) | R - R - 153–157 - R - R | 97 | h |
| XMP.337 (168) | H - H - 153–157 - H - H | 70 | b |
| XMP.337P' (168) | H - H - 153–157 - H - H | 94 | >3,350 |
| XMP.338P' (169) | ORN - ORN - 153–157 - ORN - ORN | 74 | 1,194 |
| XMP.333P' (169) | ORN - ORN - 153–157 - ORN - ORN | 96 | 1,011 |
| XMP.339 (170) | DAB - DAB - 153–157 - DAB - DAB | 74 | 2,878 |
| XMP.339P' (170) | DAB - DAB - 153–157 - DAB - DAB | 98 | 2,599 |
| XMP.340 (171) | p-amino-F - p-amino-F - 153–157 - p-amino-F - p-amino-F | 66 | b |
| XMP.340P' (171) | p-amino-F - p-amino-F - 153–157 - p-amino-F - p-amino-F | 94 | b |
| XMP.341 (172) | PYR - PYR - 153–157 - PYR - PYR | 76 | b |
| XMP.341P' (172) | PYR - PYR - 153–157 - PYR - PYR | 99 | b |
| XMP.342 (173) | $K_D$ - $K_D$ - 153–157 - $K_D$ - $K_D$ | 72 | 1,591 |
| XMP.342P' (173) | $K_D$ - $K_D$ - 153–157 - $K_D$ - $K_D$ | | 97 |
| XMP.343 (174) | K - K - 153–157 - K - K, V @ 153 (W) | 69 | NT |
| XMP.343P' (174) | K - K - 153–157 - K - K, V @ 153 (W) | | 245 |
| XMP.344 (175) | K - K - 153–157 - K - K, A @ 153 (L) | 71 | NT |
| XMP.344P' (175) | K - K - 153–157 - K - K, A @ 154 (L) | 96 | 251 |
| XMP.345 (176) | K - K - 153–157 - K - K, A @ 154 (L) | 72 | NT |
| XMP.345P' (176) | K - K - 153–157 - K - K, A @ 154 (L) | 93 | 1,211 |
| XMP.346 (177) | K - K - 153–157 - K - K, p-Amino-F @ 153 (W) | 90 | NT |
| XMP.346P' (177) | K - K - 153–157 - K - K, p-Amino-F @ 153 (W) | 98 | 640 |
| XMP.347 (178) | K - K - 153–157 - K - K, β(2-naphthyl) $A_D$ @ 153 (W), L @ 156 (Q) | 54 | NT |
| XMP.347P' (178) | K - K - 153–157 - K - K, β(2-naphthyl) $A_D$ @ 153 (W), L @ 156 (Q) | 97 | 391 |
| XMP.348 (179) | K - K - K - 153–157 - K - K | 69 | NT |
| XMP.348P' (179) | K - K - K - 153–157 - K - K | 97 | 284 |
| XMP.349 (180) | K - K - 153–157 - K - K - K | 67 | NT |
| XMP.349P' (180) | K - K - 153–157 - K - K - K | 98 | 120 |
| XMP.350 (181) | K - K - K - 153–157 - K - K | 65 | NT |
| XMp.350P' (181) | K - K - K - 153–157 - K - K | 98 | 129 |
| XMP.351 (182) | K - K - 153–158 - K - K | 59 | NT |
| XMP.351P' (182) | K - K - 153–158 - K - K | 98 | 385 |
| XMP.352 (183) | K - K - 153–161 | 66 | NT |
| XMP.352P' (183) | K - K - 153–161 | 98 | 354 |
| XMP.353 (184) | P - 153–161* | 66 | 3,093 |
| XMP.353P' (184) | P - 153–161* | 99 | 463 |
| XMP.354 (185) | † P - 153–161* | 72 | NT |
| XMP.354P' (185) | † P - 153–161* | >99 | 6,361 |
| XMP.355 (186) | P - 153–161 | 74 | 2,529 |
| XMP.355P' (186) | P - 153–161 | 99 | 218 |
| XMP.356 (187) | † P - 153–161 | 58 | NT |
| XMP.356P' (187) | † P - 153–161 | >99 | 550 |
| XMP.357 (188) | K - 153–160 - P | 64 | NT |
| XMP.357P' (188) | K - 153–160 - P | 98 | 204 |
| XMP.358 (189) | K - K - 153–160 - P | 61 | NT |
| XMP.358P' (189) | K - K - 153–160 - P | 98 | 550 |
| XMP.359 (190) | $C_D$ - 153–161 | 83 | NT |
| XMP.359P' (190) | $C_D$ - 153–161 | 96 | b |
| XMP.360 (191) | $K_D$ - $C_D$ - 154–158 - C - $K_D$ | | NT |
| XMP.361 (192) | $K_D$ - C - 154–158 - C - $K_D$ | 40 | NT |
| XMP.361' (192) | $K_D$ - C - 154–158 - C - $K_D$ | 96 | NT |
| XMP.362 (193) | $K_D$ - K - C - 154–158 - C - K - $K_D$ | 37 | NT |

TABLE 1-continued

| Peptide (SEQ ID NO:) | Peptide Amino Acid Segment | HPLC % Purity | *C. albicans* pmol/ 30 mm² zone[a] |
|---|---|---|---|
| XMP.362P' (193) | $K_D$ - K - C - 154–158 - C - K - $K_D$ | 98 | NT |
| XMP.363 (194) | $K_D$ - $W_D$ - 154–159 - $K_D$ - $K_D$ | 75 | 1,015 |
| XMP.363P' (194) | $K_D$ - $W_D$ - 154–159 - $K_D$ - $K_D$ | 97 | 741 |
| XMP.364 (195) | † $K_D$ - $W_D$ - 154–159 - $K_D$ - $K_D$ | 62 | NT |
| XMP.364P' (195) | † $K_D$ - $W_D$ - 154–159 - $K_D$ - $K_D$ | 98 | 1,523 |
| XMP.365 (196) | $K_D$ - $W_D$ - $L_D$ - $I_D$ - $Q_D$ - $L_D$ - $F_D$ - $H_D$ - $K_D$ - $K_D$ | 66 | 1,294 |
| XMP.365P' (196) | $K_D$ - $W_D$ - $L_D$ - $I_D$ - $Q_D$ - $L_D$ - $F_D$ - $H_D$ - $K_D$ - $K_D$ | 97 | 489 |
| XMP.366 (197) | † $K_D$ - $W_D$ - $L_D$ - $I_D$ - $Q_D$ - $L_D$ - $F_D$ - $H_D$ - $K_D$ - $K_D$ | 65 | NT |
| XMP.366P' (197) | $K_D$ - $W_D$ - $L_D$ - $I_D$ - $Q_D$ - $L_D$ - $F_D$ - $H_D$ - $K_D$ - $K_D$ | 99 | 725 |
| XMP.367 (198) | $K_D$ - $K_D$ - $H_D$ - $F_D$ - $L_D$ - $Q_D$ - $I_D$ - $L_D$ - $W_D$ - $K_D$ | 69 | 4,641 |
| XMP.367' (198) | $K_D$ - $K_D$ - $H_D$ - $F_D$ - $L_D$ - $Q_D$ - $I_D$ - $L_D$ - $W_D$ - $K_D$ | 99 | 1,108 |
| XMP.368 (199) | †$K_D$ - $K_D$ - $H_D$ - $F_D$ - $L_D$ - $Q_D$ - $I_D$ - $L_D$ - $W_D$ - $K_D$ | 74 | NT |
| XMP.368P' (199) | †$K_D$ - $K_D$ - $H_D$ - $F_D$ - $L_D$ - $Q_D$ - $I_D$ - $L_D$ - $W_D$ - $K_D$ | 93 | 744 |
| XMP.369 (200) | 152–161, K @ 152 (G), ORN @ 156 (Q) | 60 | 993 |
| XMP.369P' (200) | 152–161, K @ 152 (G), ORN @ 156 (Q) | 95 | 877 |
| XMP.370 (201) | † 152–161, K @ 152 (G), ORN @ 156 (Q) | 59 | NT |
| XMP.370P' (201) | † 152–161, K @ 152 (G), ORN @ 156 (Q) | >99 | 310 |
| XMP.371 (202) | 152–161, K @ 152 (G), DAB @ 156 (Q) | 74 | 843 |
| XMP.371P' (202) | 152–161, K @ 152 (G), DAB @ 156 (Q) | 97 | 523 |
| XMP.372 (203) | † 152–161, K @ 152 (G), DAB @ 156 (Q) | 50 | NT |
| XMP.372P' (203) | † 152–161, K @ 152 (G), DAB @ 156 (Q) | 99 | 328 |
| XMP.373P' (204) | † 152–161, K @ 152 (G) | 98 | 298 |
| XMP.374 (205) | $K_D$ - $L_D$ - $Q_D$ - $I_D$ - $L_D$ - $W_D$ - $K_D$ - $K_D$ | | |
| XMP.374P' (205) | $K_D$ - $L_D$ - $Q_D$ - $I_D$ - $L_D$ - $W_D$ - $K_D$ - $K_D$ | 97 | 198 |
| XMP.375P' (206) | $K_D$ - $K_D$ - $W_D$ - $A_D$ - $I_D$ - $Q_D$ - $L_D$ - $K_D$ - $K_D$ | 95 | 123 |
| XMP.376P' (207) | $K_D$ - $K_D$ - $L_D$ - $Q_D$ - $I_D$ - $A_D$ - $W_D$ - $K_D$ - $K_D$ | 92 | 138 |
| XMP.377P' (208) | K - K - K - W - A - I - Q - L - K - K | 97 | 146 |
| XMP.378P' (209) | P - W - A - I - Q - L - K - K | 97 | 2,084 |
| XMP.379P' (210) | K - K - P - W - A - I - Q - L - K - K | 98 | 547 |
| XMP.380P' (211) | K - K - Q - L - L - L - L - K - K | 99 | 886 |
| XMP.381P' (212) | K - K - L - Q - L - L - L - K - K | 99 | 391 |
| XMP.382P' (213) | K - K - L - L - Q - L - L - K - K | 99 | 1,437 |
| XMP.383P' (214) | K - K - L - L - L - Q - L - K - K | 99 | 473 |
| XMP.384P' (215) | K - K - L - L - L - L - Q - K - K | 99 | 2,804 |
| XMP.385P' (216) | K - K - L - L - L - L - L - K - K | 99 | 127 |
| XMP.386P' (217) | 152–161, K @ 152 (G), A @ 154 (L) | 97 | 113 |
| XMP.387P' (218) | 152–161, P @ 152 (G), A @ 154 (L) | 93 | 82 |
| XMP.388P' (219) | 152–161 | 97 | 170 |
| XMP.389P' (220) | 151–161, K @ 151 (V) | 99 | 206 |
| XMP.390P' (221) | 151–161, K @ 151 (V), P @ 152 (G) | 98 | 674 |
| XMP.391P' (222) | 150–161 | 97 | 68 |
| XMP.392P' (223) | 150–161, P @ 152 (G) | 98 | 569 |
| XMP.393 (224) | 148–161, P @ 152 (G) | >99 | NT |
| XMP.394 (225) | $K_D$ - $L_D$ - $F_D$ - $R_D$ - β(1-naphthyl)$A_D$ - $Q_D$ - $A_D$ - $K_D$ - β(1-naphthyl)$A_D$ - $K_D$ - $G_D$ - $S_D$ - $I_D$ - $K_D$ - $I_D$ | NT | |
| XMP.395 (226) | 148–161, β(1-naphthyl)A @ 153 (W), L 156 (Q) | | NT |
| XMP.396 (227) | 148–161, β(1-naphthyl)A @ 153 (W), F @ 156 (Q) | | NT |
| XMP.397 (228) | 148–161, p-amino-F @ 152 (G), β(1-naphthyl)A @ 153 (W), W @ 158 (F) | | NT |
| XMP.398 (229) | 148–161, L @ 156 (Q), β(1-naphthyl)A @ 157 (L) | | NT |
| XMP.399 (230) | 148–161, F @ 156 (Q), W @ 158 (F) | | NT |
| XMP.400 (231) | 148–161, β(1-naphthyl)A @ 153 (W), L @ 156, W @ 158 | | NT |
| XMP.401 (232) | 148–161, F @ 156 (Q), β(1-naphthyl)A @ 157 (L) | | NT |
| XMP.402 (233) | 148–161, β(1-naphthyl)A @ 153 (W), F 156 (Q), W @ 158 (F) | | NT |
| XMP.403 (234) | 148–161, β(1-naphthyl)A @ 153 (W) and 157 (L), W @ 158 (F) | | NT |
| XMP.404 (235) | 148–161, F @ 156 (Q), β(1-naphthyl)A @ 157 (L), W @ 158 (F) | | NT |

TABLE 1-continued

| Peptide (SEQ ID NO:) | Peptide Amino Acid Segment | HPLC % Purity | C. albicans pmol/ 30 mm² zone[a] |
|---|---|---|---|
| XMP.405 (236) | 148–161, L @ 156 (Q), β(1-naphthyl)A @ 157 (L), W @ 158 (F) | | NT |
| XMP.406P' (237) | 147–161, P @ 147 (S), A @ 153 (W) | 99 | 423 |
| XMP.407P' (238) | 147–162, P @ 147 (S), A @ 153 (W), D @ 162 (I) | 96 | 1,240 |
| XMP.408P' (239) | L - K - K - K - W - A - I - Q (cyclized head to tail) | | b |
| XMP.409P' (240) | S - K - 153–157 - K - K, A @ 154 (L) | 98 | 795 |
| XMP.410P' (241) | $CH_3 - (CH_2)_6 - CO - XMP.344$ | 95 | 599 |
| XMP.411 (242) | $CH_3 - (CH_2)_{10} - CO - XMP.344$ | | |
| XMP.412 (243) | L - K - K - K - W - A - I - Q | | NT |
| XMP.414 (244) | $CH_3 - (CH_2)_6 - CO - XMP.365$ | | |
| XMP.415 (245) | $CH_3 - (CH_2)_{10} - CO - XMP.365$ | | |
| XMP.416 (246) | $NH_2 - (CH_2)_7 - CO - XMP.365$ | | |
| XMP.417 (247) | $NH_2 - (CH_2)_{11} - CO - XMP.365$ | | |
| XMP.418 (248) | 148–150, 152–161, P @ 152 (G) | | 572 |
| XMP.419 (249) | † $K_D - W_D - L_D - I_D - L_D - F_D - H_D - K_D - K_D$ | | NT |
| XMP.420 (250) | Fmoc - $K_D - W_D - L_D - I_D - Q_D - L_D - F_D - H_D - K_D - K_D$ | | NT | a pmoles of peptide added to well to achieve a 30 mm² zone as determined by PROBIT analysis
b No detectable activity up to 5 μg/well
c NT = not tested
d † = peptide has an acetylated amino terminus; * = peptide has a non-amidated carboxy-terminus
e Abbreviations: $X_D$ refers to a D-amino acid; ORN is ornithine; DAB is diamino butyric acid; PYR is pyridinyl-alanine (free acid)
f "P" refers to XMP peptide purified as described in Example 1
g inactive to 7,194 pmol
h inactive to 5,268 pmol

EXAMPLE 3

In Vitro and In Vivo Effect of Anti-fungal Peptides On A Variety of Fungal Species This example addresses in vitro and in vivo screening of various Domain III derived peptides for anti-fungal activity against a number of fungal species, including Candida species and strains resistant to various anti-fungal agents, in a radial diffusion assay. The example also addresses the effects of combinations of peptide and amphotericin B against Candida strain SLU-1.

Domain III derived peptides were tested for their fungicidal activity on amphotericin resistant Candida. Resistant colonies of Candida were isolated using a gradient plate technique. A slanted Sabouraud dextrose agar plate was poured and allowed to harden. The plate was made level and additional agar supplemented with nystatin (Sigma, St. Louis, Mo., cat. no. N-3503) at a concentration of 10 μg/mL was poured. Cells from the CA-1 colony of *Candida albicans* SLU-1 strain described in Example 2 (10⁷ cells in a volume of 100 μL) were spread over the plate and incubated at 3° C. overnight. Initially, minute colonies were seen and required additional incubation time to achieve the size of wildtype colonies. Eleven colonies were designated SLU-2A though SLU-2K. These colonies were serially passaged in Sabouraud dextrose broth with increasing concentrations of amphotericin B, after an initial passage with 2 μg/mL amphotericin B. After the final passage in 20 μg/mL amphotericin B, colonies 2G, 2H, 21 and 2K remained viable whereas the wildtype SLU-1 strain remained sensitive to 1 μg/mL amphotericin B. None of the resistant strains demonstrated germ tube formation in fetal bovine serum. In addition, these isolates had a much slower growth rate than SLU-1 and did not form hyphae at 37° C.

For the radial diffusion assays, *Candida albicans* SLU-1 were grown as described above and SLU-2G were grown overnight in Sabouraud dextrose broth supplemented with 10 μg/mL amphotericin B and 5 μg/mL ceftriaxone at 37° C. Cultures were diluted 1:25 into fresh, unsupplemented broth and allowed to grow for 5 hours at 37° C. Cells were pelleted at 1,500×g for 5 minutes at 4° C. Supernatant was decanted and replaced with 5 mL of 10 mM phosphate buffer, pH 7.4. After centrifugation the cell pellets were resuspended with 5 mL phosphate buffer for an $OD_{570}$ determination. One $OD_{570}$ for SLU-1 cells was 3×10⁷ CFU/mL and for SLU-2G cells was 5×10⁶ CFU/mL.

Cells were added to 10 mL of molten, cooled (~45° C.) underlayer agarose to a concentration of 1×10⁶/mL and the suspension was poured into a level square petri plate with gentle rocking to allow even distribution and solidification to a uniform thickness of about 1 mm. Wells were cut into the hardened agarose with a sterilize, 3 mm diameter punch with vacuum.

Figure 2A:
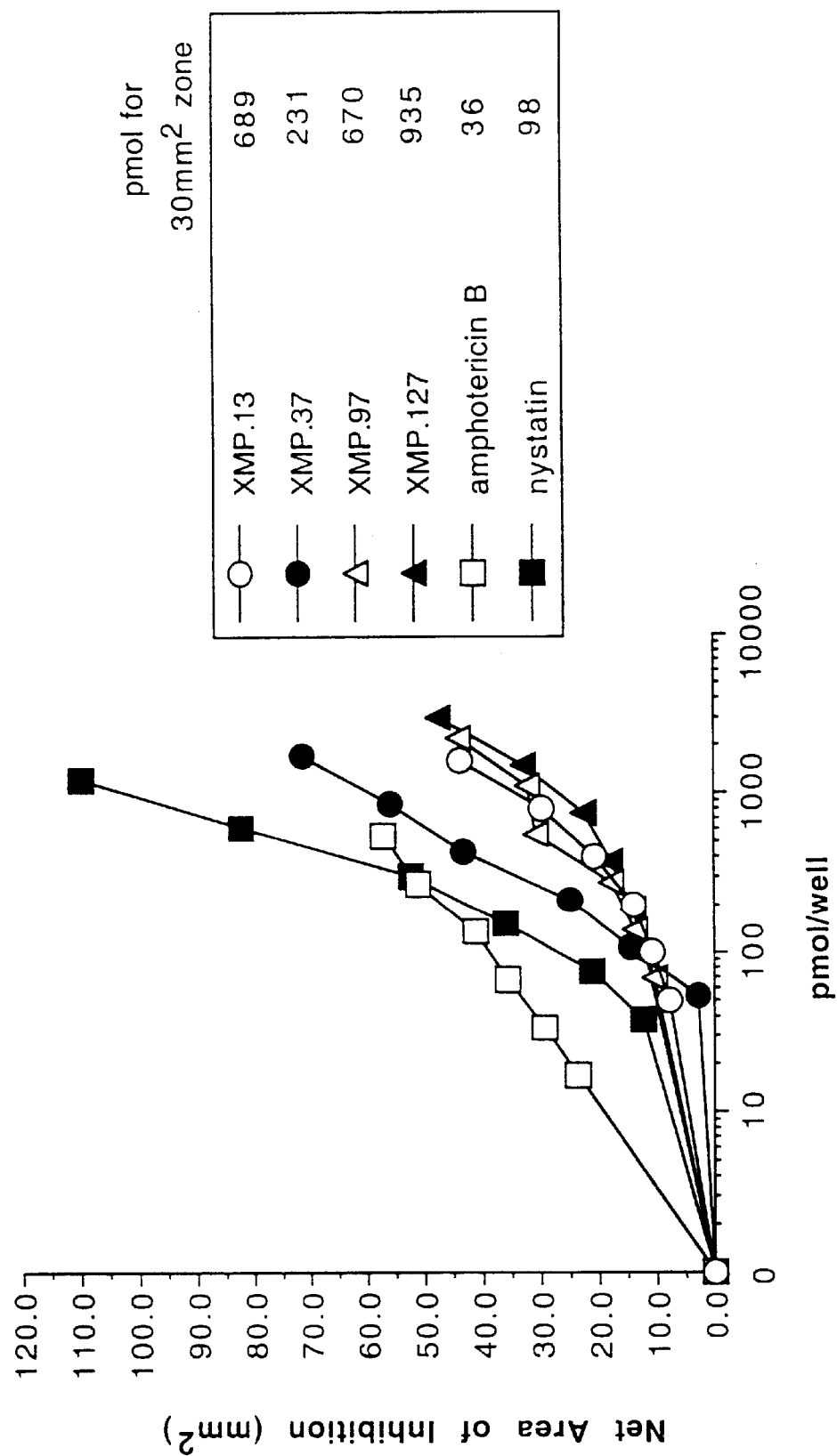
FIGS. 2A and 2B provide results of radial diffusion assays of the activity of various peptides against *C. albicans* SLU-1 (FIG. 2A) and *C. albicans* SLU-2G (FIG. 2B).
Figure 2B:
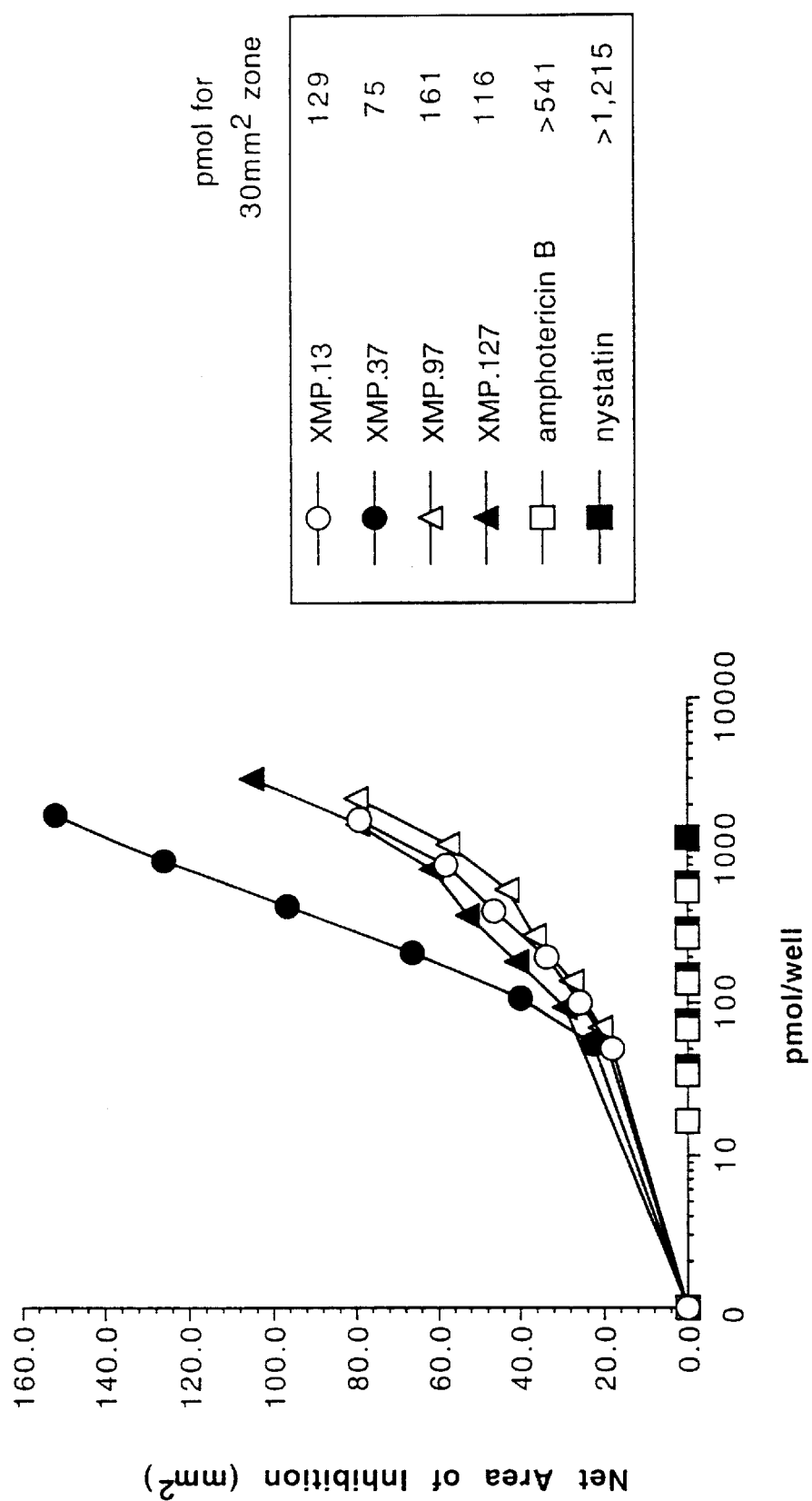

Peptides were two-fold serially diluted with DPBS from a starting concentration of approximately 1 mg/mL. Amphotericin B and nystatin were similarly diluted starting at 100 and 225 μg/mL, respectively. Five μL were added per well and allowed to diffuse at 37° C. for 1.5–2.0 hours. Then 10 mL of molten overlayer agarose were added and the plates were incubated inverted at 37° C. overnight. Plates were stained with a dilute Coomassie solution, inhibition zones were measured with calipers and net areas were calculated, then converted to pmol values by PROBIT analysis. The results of a representative experiment are shown in FIG. 2A for the SLU-1 strain and FIG. 2B for the SLU-2G strain. In FIGS. 2A and 2B, the fungicidal activity is represented for XMP.13 as open circles; for XMP.37 as closed circles; for XMP.97 as open triangles; for XMP.127 as closed triangles; for amphotericin B as open squares; and for nystatin as closed squares. The pmol for a 30 mm² zone of inhibition were calculated to be: for XMP.13, 689 pmol against SLU-1 and 129 pmol against SLU-2G; for XMP.37, 231 pmol against SLU-1 and 75 pmol against SLU-2G; for XMP.97, 670 pmol against SLU-1 and 161 pmol against SLU-2G; for XMP.127, 935 pmol against SLU-1 and 116 pmol against SLU-2G; for amphotericin B, 36 pmol against SLU-1 and >541 pmol for SLU-2G; and for nysttin, 98 pmol against SLU-1 and >1,215 pmol against SLU-2G. As shown in FIGS. 2A and 2B, representative Domain III derived peptides XMP.13, XMP.37, XMP.97 and XMP.127 demonstrated fungicidal activity against both the SLU-1 wild type strain and the SLU-2G amphotericin B-resistant strain, with better activity demonstrated against the SLU-2G amphotericin B resistant strain. In contrast, amphotericin B was effective against the original SLU-1 strain but did not kill the SLU-2G resistant cells. These results demonstrate that Domain III derived peptides according to the invention are effective fungicidal agents by a mechanism different from that of amphotericin B.

Further experiments were performed to determine the anti-fungal activity of Domain III derived peptides on commercially-available strains of Candida considered resistant to other anti-fungal agents: polyene-resistant *C. albicans* (ATCC Accession No. 38247), 5-fluorocytosine-resistant *C. albicans* (ATCC No. 44373), azole-resistant *C. albicans* (ATCC No. 62342), and ketoconazole-resistant *C. albicans* (ATCC No. 64124). Fungicidal activity of representative peptides XMP.13, XMP.36, XMP.97, XMP.127, and XMP.166 was not reduced on the above strains tested, indicating that the peptides are effective by a mechanism different than that of the other anti-fungal agents.

The anti-fungal activity of Domain III derived peptides was also evaluated in vitro against a variety of fungal species, including *Candida glabrata, Candida krusei, Candida lusitaniae, Candida parapsilosis*, and *Candida tropicalis*. For these experiments, one colony of each of the above-listed Candida strains was picked from a Sabouraud's dextrose agar (SDA) plate and inoculated into 5 mL of Sabouraud's dextrose broth (SDB, 2% dextrose and 1% neopeptone) or, for *C. krusei*, Yeast Malt broth (YM, Becton Dickenson, Cockeysville, Md., cat no. BL 11405) in 12 mL polyproplyene snap-cap tubes. The tube cultures were incubated overnight with shaking at 37° C.

Cultures were harvested when the $OD_{570}$ of a 1:10 dilution was greater than or equal to the following values: 0.083 for *Candida glabrata*, 0.154 for *Candida krusei*, 0.117 for *Candida lusitaniae*, 0.076 for *Candida parapsilosis*, and 0.192 for *Candida tropicalis*. Cells were centrifuged for 7 minutes in an Eppendorf microfuge at 3,000 rpm (about 1,500 g). The cell pellet was resuspended in 1 mL PBS and approximately $1 \times 10^7$ cells in about 0.5 mL were added to 10 mL of cooled underlay agar (3% SBD, 1% agarose, 0.02% Tween 20, 10 mM sodium phosphate buffer, pH 7.4 at about 45° C.). The suspension was poured into square petri plates, allowed to solidify, and wells cut as described above.

Peptides were two-fold serially diluted with D-PBS from about 20 $\mu$L of a starting concentration of approximately 1 mg/mL. Five $\mu$L of peptide dilution were added per well and allowed to diffuse for at least about 30 minutes into the agar at 3° C. (to allow complete diffusion). Then 10 mL of molten overlayer agarose (6% SDB, 1% agarose, 10 mM sodium phosphate buffer, pH 7.4 at about 45° C.) were added and the plates were incubated inverted at 3° C. overnight. Plates were stained with a dilute Coomassie solution, inhibition zones were measured with calipers and net areas were calculated, then converted to pmole values by PROBIT analysis. The results of a representative experiment are shown in Table 2. Exemplary Domain III derived peptides XMP.13P, XMP.97P, XMP.127P, XMP.166P, XMP.286P, XMP.327P, XMP.331P, P.332P, XMP.333P and XMP.337P demonstrated some fungicidal activity against at least several of the Candida strains tested. These results demonstrate that Domain III derived peptides according to the invention are effective fungicidal agents in a broad spectrum against a variety of Candida species.

TABLE 2

Anti-fungal activity: pmol/30 mm$^2$ zone[a,d]

| | Candida albicans | Candida glabrata | Candida krusei | Candida lusitaniae | Candida parapsilosis | Candida tropicalis |
|---|---|---|---|---|---|---|
| XMP.13P[e] | 2,233 | 1,022 | 1,747 | 746 | 1,502 | 452 |
| XMP.97P[e] | 2,019 | 1,786 | 907 | 900 | 868 | 193 |
| XMP.127P | 2,144 | 779 | 878 | 551 | 711 | 373 |
| XMP.166 | >3,079 | 2,100 | 3,240 | 1,133 | 1,199 | 864 |
| XMP.286P[e] | NT[c] | 1,843 | 1,558 | 1,235 | 1,134 | 606 |
| Amphotericin B | 11 | <17 | 120 | 35 | 91 | 108 |
| XMP.327P[e] | 5,108 | >6,295 | 3,327 | 120 | 119 | 2,598 |
| XMP.331P[e] | b | b | >5,467 | 1,500 | 1,451 | b |
| XMP.332P[e] | 3,931 | 2,190 | 2,802 | <219 | 170 | 866 |
| XMP.333P[e] | 5,191 | 4,040 | 4,101 | 174 | 209 | 2,894 |
| XMP.337P[e] | b | b | 5,339 | 6,928 | b | b |

[a] pmol of peptide added to well to achieve a 30 mm$^2$ zone as determined by PROBIT analysis
[b] No detectable activity up to 5 $\mu$g/well
[c] NT = not tested
[d] Actual pmol values obtained are dependent on assay conditions; values in this Table for *C. albicans* higher than those presented in Table 1 due to higher effective concentration of agarose during incubation
[e] "P" refers to XMP peptide purified as described in Example 1

The anti-fungal activity of Domain III derived peptides was evaluated against a variety of fungal species, including species of Candida. Cryptococcus, Fusarium, Trichophyton, and Aspergillus, by an additional assay protocol utilizing Alamar Blue. Alamar Blue is an indicator dye formulated to measure quantitatively the proliferation of a variety of human or animal cells, bacteria, or fungi. It consists of an oxidation-reduction (REDOX) indicator that yields a colorimetric change in response to metabolic activity.

For these experiments, species of Candida and Cryptococcus were grown in Sabouraud's dextrose broth (SDB) overnight. Strains of filamentous fungi (Aspergilius, Fusanum, Trichophyton) were obtained by irrigation of a confluent culture from a petri dish. Cells were washed and adjusted to a concentration of $5.0 \times 10^3$/mL in fresh SDB. Peptides were two-fold serially diluted in SDB from a concentration of 20 μg/mL. Controls included amphotericin B, fluconazole, ketoconazole and griseofulvin. Antifungal drugs were also diluted in the same manner.

Assays were performed in 96-well microuiter plates. Peptides were in a volume of 100 μL per well followed by the addition of 100 μL of the fungal cell suspension. Final concentration of fungi was $2.5 \times 10^3$/mL and test antifungal compounds started from a concentration of 10 μg/mL. Alamar Blue was added at 20 μL per well and plates were incubated for a period of 18 hours at 37° C. for Aspergillus, Candida, Cryptococcus, 48–72 hours at 30° C. for slower growing fungi (i.e., Trichophyton). Plates were centrifuged briefly (1,000 rpm, 1 minute) to pellet fungal cells or debris.

TABLE 3

Antifungal Agent Minimum Fungicidal Concentration (μg/mL)

| Antifungal Agent | SLU-1 | ATCC 10231 | ATCC 18840 | ATCC 26555 | ATCC 44808 | ATCC 90028 |
|---|---|---|---|---|---|---|
| | | | *Candida albicans* | | | |
| XMP.284 | 2.50 | 5.0 | 2.5 | 1.25 | 1.25 | 1.25 |
| XMP.342 | 5.00 | 10.0 | 5.0 | 2.5 | 5.0 | 5.0 |
| XMP.353 | 2.5 | | | | | |
| XMP.364 | | | | | | |
| XMP.365 | 2.5 | 5.0 | 5.0 | 1.25 | 5.0 | 5.0 |
| XMP.366 | 10.0 | 10.0 | >10.0 | 10.0 | >10.0 | 10.0 |
| XMP.367 | 2.5 | 5.0 | 2.5 | 2.5 | 10.0 | 5.0 |
| XMP.373 | 2.5 | 5.0 | 2.5 | 1.25 | 2.5 | 2.5 |
| XMP.389 | 2.5 | 5.0 | 2.5 | 1.25 | 2.5 | 2.5 |
| XMP.391 | 1.25 | 1.25 | 1.25 | 0.62 | 1.25 | 2.5 |
| Amphotericin B | 0.63 | 0.63 | 1.25 | 1.25 | 1.25 | 1.25 |
| Fluconazole | >10.0 | >10.0 | >10.0 | >10.0 | >10.0 | >10.0 |
| Ketoconazole | | >10.0 | >10.0 | >10.0 | >10.0 | >10.0 |

TABLE 4

Antifungal Agent Minimum Fungicidal Concentration (μg/mL)

| Antifungal Agent | *Candida glabrata* ATCC 2001 | *Candida parapsilosis* ATCC 22019 | *Cryptococcus neoformans* ATCC 13690 | *Fusarium solani* ATCC 36031 | *Trychophyton rubrum* ATCC 28188 | *Aspergillus* ATCC 13073 | *Aspergillus niger* ATCC 16404 |
|---|---|---|---|---|---|---|---|
| XMP.284 | >10.0 | >10.0 | 0.63 | 0.31 | 5.0 | 12.50 | 2.5 |
| XMP.342 | >10.0 | >10.0 | 1.25 | 1.25 | 10.0 | 25.00 | 10.00 |
| XMP.353 | | | 0.63 | | | 12.50 | |
| XMP.364 | | | | | | | |
| XMP.365 | >10.0 | 10.0 | 1.25 | 0.16 | 10.0 | 25.00 | 5.00 |
| XMP.366 | >10.0 | >10.0 | 1.25 | 10.0 | >10.0 | 50.00 | >10.00 |
| XMP.367 | >10.0 | 10.0 | 1.25 | 0.31 | >10.0 | 50.00 | 5.00 |
| XMP.373 | 10.0 | 10.0 | 0.63 | 2.5 | 2.5 | >50.00 | 2.50 |
| XMP.389 | 5.0 | 5.0 | 0.63 | 1.25 | 5.0 | 25.00 | 1.25 |
| XMP.391 | 5.0 | 2.5 | 0.31 | 0.31 | 2.5 | 12.50 | 1.25 |
| Amphotericin B | 0.32 | 5.0 | 1.25 | 0.62 | 0.32 | 12.50 | 5.00 |
| Fluconazole | >10.0 | >10.0 | >10.0 | >10.0 | >10.0 | >50.00 | >10.00 |
| Ketoconazole | >10.0 | 5.0 | | >10.0 | | | >10.00 |

100 μL from each well was transferred to new 96well plates and an $OD_{590}$ reading was performed on an ELISA plate reader.

50 μL from the original 96-well plates were plated on Sabouraud's dextrose agar to determine fungicidal activity. The wells to be plated were determined by $OD_{590}$ readings. The lowest concentration of peptide which maintained the blue color (or OD reading) of the blank was chosen along with the next two higher concentrations. Plates were allowed to grow for 18–48 hours depending on the rate of growth of each fungus. Minimal fungicidal activity (MFC) was determined as a 99.9% killing of the starting inoculum. For filamentous fungi, this was determined as the lowest concentration of peptide which showed no growth (complete sterilization). The results of these assays are shown for representative peptides in Tables 3 and 4. These results demonstrate that Domain III derived peptides according to the invention are effective fungicidal agents in a broad spectrum against a variety of fungal species.

In additional experiments, a fluorescence-activated cell sorter (FACS) based assay was developed to test the fungicidal activity of the peptides. For these experiments, fungi were cultured and isolated by platino on Sabouraud's Dextrose (1% Neopeptone, 2% Dextrose; Difco) agar. Several colonies were picked from the agar plate and inoculated into 5 mL of Sabouraud's Dextrose media in a sterile 10 mL polypropylene tube. The fungal cultures were incubated for about 18 hours at 30° C. At the end of incubation, 4 mL of the fungal culture were inoculated into a flask of 100 mL of Sabouraud's Dextrose broth (SDB). The 100 mL culture was inoculated for about 5 hours or until log growth. When the culture reached log growth, the 100 mL culture was decanted into two 50 mL conical popypropylene centrifuge tubes. The culture were centrifuged at 3000 rpm for 5 minutes (Sorvall RT 6000B). After centrifugation, the supernatant was decanted leaving the fungal pellets in the centrifuge tubes. The pellets were resuspended in 15 mL of SDB. Both suspensions were combined into one tube and mixed to generate a stock culture. The concentration of the fungal stock was determined by either diluting a sample of the stock 1:10 with SDB and then determining the OD of the dilution by spectrophotometry at 570 nm (Shirnadzu UV-160 spectrophotometer) or by diluting the stock 1:10 with Trypan Blue and counting the cells using a hemacytometer. After determining the concentration of the stock, appropriate dilutions were made with Sabouraud's Dextrose media to obtain 100 mL of $1 \times 10^6$ cell/mL.

Peptide solutions were prepared in saline to concentrations of approximately 1 mg/mL. In a 96 well popypropylene plate (Costar 3790), the peptides were diluted 1:2 six times in a serial dilution with PBS. Then 1 mL of the $1 \times 10^6$ cells/mL cell suspension was dispensed into appropriate number of FACScan tubes (Falcon 2054), seven tubes per peptide and three tubes for assay controls (positive, negative, and autofluorescence controls). Approximately 20 μl of the peptide solutions were added to the 1 mL cell suspension to achieve a formal peptide concentration in the tube of 20, 10, 5, 2.5, 1.25, 0.625, and 0.313 μg/mL peptide. The tubes were incubated at 30° C. for 1 hour except for the positive control tube which was incubated for 40 minutes, then centrifuged at 3000 rpm for 5 minutes. The supernatant was decanted and the cell pellet was resuspended with 1 mL of 70% EtOH then incubated for 10 minutes to achieve 100% kill. After the 1 hour incubation, all the tubes were centrifuged at 3000 rpm for 5 minutes. Supernatants were decanted and the pellets resuspended with 1 mL of 80 μg/mL of propidium iodide (Sigma, St. Louis, Mo.) in Dulbecco's PBS (DPBS, GIBCO, Grand Island, N.Y.) except the autofluorescence control, which was resuspended in DPBS alone. The tubes were mixed and incubated in the dark at room temperature for at least 20 minutes.

The FACScan flow cytometer (Becton Dickenson, Mountainview, Calif.) was allowed to warm up for at least 5 minutes before assay analysis. The settings were adjusted appropriately to the following approximate parameters:

|  | Amplifier | Detector |
| --- | --- | --- |
| FSC | 1.00–2.00 | E00 |
| SSC | 1.00–2.00 | 200–300 |
| FL1 | Log | 400–500 |
| FL2 | Log | 400–500 |

Cells were analyzed (10,000 cells/tube) and their respective fluorescence determined. In these experiments, the autofluorescent control did not have significant fluorescence. The population of dead (i.e., propidium iodide stained) fungal cells was determined by a fluorescence threshold between the negative control and positive control. For all concentrations of peptides, the percentage of dead cells was plotted against peptide concentration and an $IC_{50}$ was determined by curve fitting. The results for representative peptides are shown in Tables 5 through 8 below.

TABLE 5

Activity of peptides on *C. albicans* SLU-1

| Peptide | $IC_{50}$ (μg/mL) |
| --- | --- |
| XMP.284 | 0.31 |
| XMP.353 | 0.53 |
| XMP.268 | 0.55 |
| XMP.342 | 0.60 |
| XMP.391 | 0.64 |
| XMP.391 | 0.73 |
| XMP.391 | 0.73 |
| XMP.366 | 0.89 |
| XMP.389 | 0.95 |
| XMP.373 | 1.13 |
| XMP.342 | 1.88 |

TABLE 5-continued

Activity of peptides on *C. albicans* SLU-1

| Peptide | $IC_{50}$ (μg/mL) |
| --- | --- |
| XMP.342 | 2.03 |
| XMP.465 | 2.11 |
| XMP.367 | 2.37 |
| XMP.406 | 4.29 |
| XMP.378 | 13.09 |
| XMP.407 | 27.03 |
| Amphotericin B | 79.36 |

TABLE 6

Activity of peptides on various strains of *C. albicans*

| | $IC_{50}$ (μg/mL) | | | | |
| --- | --- | --- | --- | --- | --- |
| Peptides | SLU#1 | 10231 | 90028 | 26555 | 14053 |
| XMP.284 | 0.31 | 1.86 | 1.08 | 0.59 | 0.50 |
| XMP.342 | 1.88 | 8.07 | 3.44 | 3.19 | 2.74 |
| XMP.365 | 2.11 | 3.75 | 0.27 | 0.15 | 0.13 |
| XMP.366 | 0.89 | 4.53 | 2.29 | 0.69 | 1.35 |
| XMP.367 | 2.37 | ND | 0.22 | 0.21 | 0.08 |
| XMP.373 | 1.13 | 2.92 | 1.86 | 1.46 | 1.64 |
| XMP.389 | 0.95 | 3.12 | 2.79 | 0.89 | 0.95 |
| XMP.391 | 0.64 | 2.06 | 1.29 | 0.79 | 1.04 |

ND = Not Determined

TABLE 7

Activity of Peptides on Various Candida Species

| Peptide | *Candida glabrata* $IC_{50}$ (μg/mL) | *Candida lusitaniae* $IC_{50}$ (μg/mL) | *Candida parasilosis* $IC_{50}$ (μg/mL) |
| --- | --- | --- | --- |
| XMP.284 | 6.27 | 1.20 | 1.82 |
| XMP.342 | 11.00 | 3.24 | NT |
| XMP.365 | 15.26 | 1.25 | 7.72 |
| XMP.366 | 21.00 | 3.03 | NT |
| XMP.367 | 20.00 | 1.25 | 2.32 |
| XMP.373 | 4.96 | 1.11 | 3.74 |
| XMP.389 | 4.64 | 2.26 | 5.36 |
| XMP.391 | 2.85 | 1.69 | 0.85 |

NT = Not Tested

TABLE 8

Activity of Peptides on *Crytococcus Neoformans* 13690

| Peptide | $IC_{50}$ (μg/mL) |
| --- | --- |
| XMP.284 | 0.11 |
| XMP.342 | 0.95 |
| XMP.353 | 0.37 |
| XMP.365 | 0.03 |
| XMP.366 | 0.47 |
| XMP.367 | 0.05 |
| XMP.373 | 0.87 |
| XMP.389 | 0.25 |
| XMP.391 | 0.34 |

The effects of combinations of peptide and amphotericin B against Candida strain SLU-1 were studied. For these experiments, *Candida albicans* SLU-1 was grown and assayed in a broth dilution assay as described in Example 2, except that peptide alone, amphotericin B alone, or combinations of peptide and amphotericin B were incubated with the fungal cells for testing.

Figure 3:
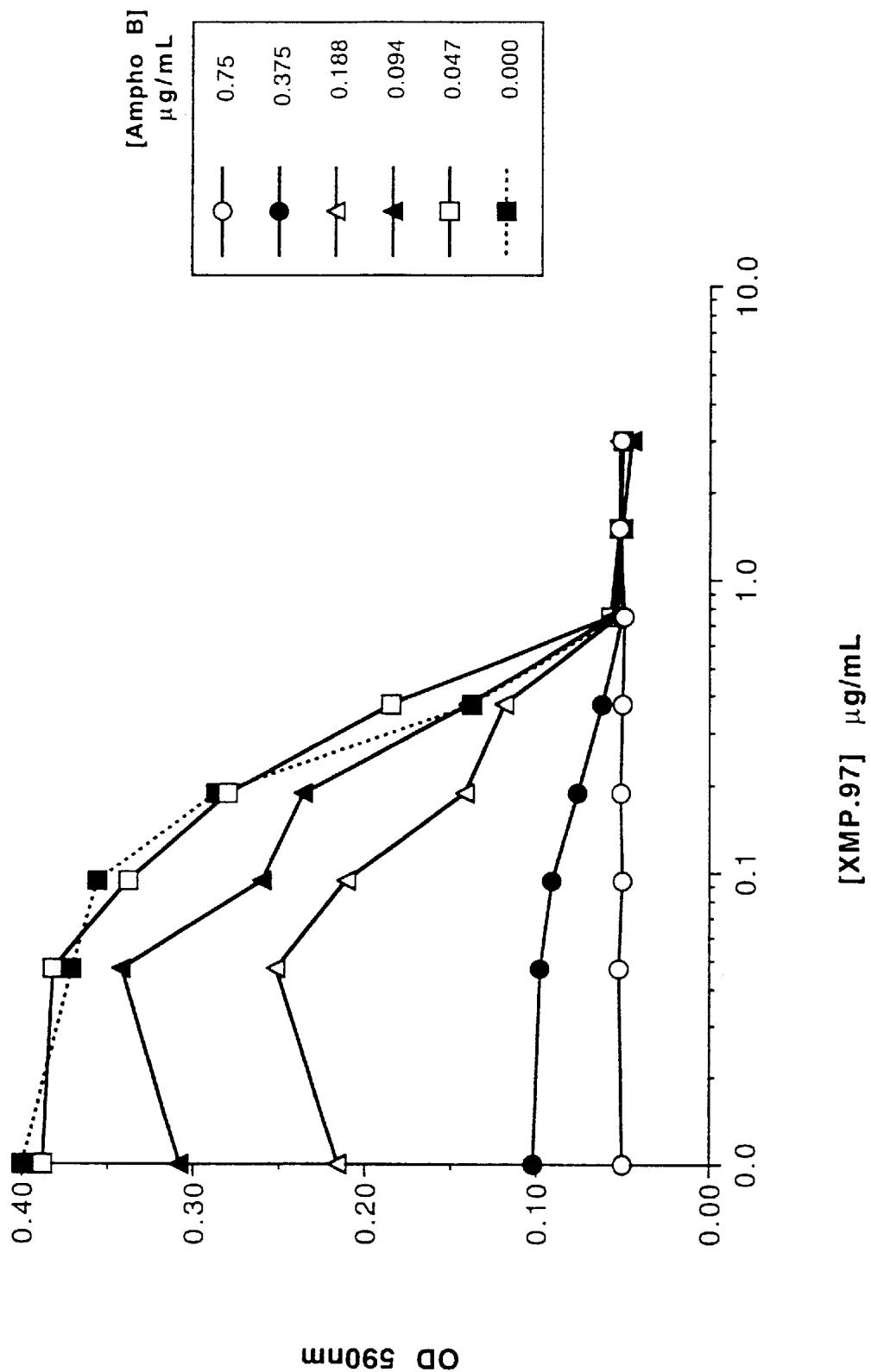
FIG. 3 provides results of broth assay tests of the activity of combinations of peptide and amphotericin B against *C. albicans*.

The results of such an assay using representative peptide XMP.97, alone or in combination with amphotericin B, are shown in FIG. 3. In FIG. 3, the fungicidal activity of combinations of XMP.97 and amphotericin B are represented for the XMP.97 concentrations shown and concentrations of amphotericin B of 0.047 µg/ml (open squares); 0.074 µg/ml (closed triangles); 0. 188 µg/ml (open triangles; 0.375 µg/ml (closed circles); and 0.750 µg/ml (open circles). The activity of XMP.97 alone is represented by the closed squares. Both XMP.97 and amphotericin B are each effective alone at certain concentrations as anti-fungal agents. The combination of peptide and amphotericin B does not result in inhibition (as it would if the two drugs were antagonistic), but rather results in decreasing the amount of both anti-fungal agents required for maximum killing. In particular, concurrent administration of this Domain III derived peptide with an anti-fungal agent, such as amphotericin B, achieved an improved therapeutic effectiveness through reducing the concentration of amphotericin B required to eradicate or inhibit fungal growth. Because the use of amphotericin B has been limited by its systemic toxicity, lowering the concentration of such an anti-fungal agent required for therapeutic effectiveness can reduce toxicity, and thus may allow wider use of this agent.

The anti-fungal activity of Domain III derived peptides may also be evaluated in vivo in animal models for a variety of fungal species, including *Cryptosporidium parvum*, *Cryptococcus neoformans* and *Histoplasma capsulatum*. Animal models for *C. parvum*, sponsored by contract resources from the National Institute of Allergy and Infectious Diseases, include severe combined immunodeficiency (SCID) mouse models and a colostrum-deprived SPF piglet model.

The anti-fungal activity of Domain III derived peptides may be evaluated in vivo in additional animal models, including, for example, a granulocytopenic rabbit model of disseminated Candidiasis such as described by Walsh et al., *J. Infect. Dis.*, 161:755–760 (1990) and Thaler et al., *J. Infect. Dis.*, 158:80 (1988); a mouse model of disseminated Aspergillosis such as described by Arroyo et al., *Antimicrob. Agents & Chemo.*, pp. 21–25 (January, 1977), and a neutropenic rat model of disseminated Candidiasis such as described by Lechner et al., *Am. J. Physiol.* (*Lung Cell. Mol. Physiol.*) 10:1–8 (1994) and references cited therein.

EXAMPLE 4

In Vivo Anti-fungal Effect of Peptides In Mice With Systemic Candida Infection

This example addresses the in vivo anti-fungal effects of Domain III derived peptides in mitigating the total mortality or mortality rate of mice systemically infected with *Candida albicans*. Peptides that had been screened for anti-fungal activity in the radial diffusion and broth assays described in Example 2 were prepared and purified as described in Example 1.

Groups of 15 male DBA/2J mice at age 6–8 weeks (Jackson Laboratory, Bar Harbor, Me.) were inoculated with $1.24 \times 10^5$ *C. albicans* (SLU-1 strain as described in Example 2) by intravenous injection into the tail vein. Cells were prepared for animal injection as follows. A single colony was selected and used to inoculate a 5 mL tube of Sabouraud dextrose broth. Incubation was at 30° C. with shaking to allow aeration for a period of 15–18 hours. Four mL of the overnight culture were added to 100 mL of fresh Sabouraud dextrose broth (1:25 dilution) and incubated for 4 hours. The 100 mL culture was pelleted at 1,500xg for 5 minutes. Cells were washed twice by adding 20 mL D-PBS, vortexing and re-centrifuging. Cells were collected in one tube and a sample is diluted 1:10 to be measured by $OD_{570}$ (1 OD unit=$3 \times 10^7$ CFU/mL). The cells were diluted to the desired dose in D-PBS and kept at 4° C. until used. Doses were confirmed by performing serial ten-fold dilutions and plating 50 µl per dilution on Sabouraud dextrose agar. Colonies were counted the following day after overnight incubation at 37° C. A 500 mL culture yielded approximately $1 \times 10^9$ CFU/mL.

Figure 4:
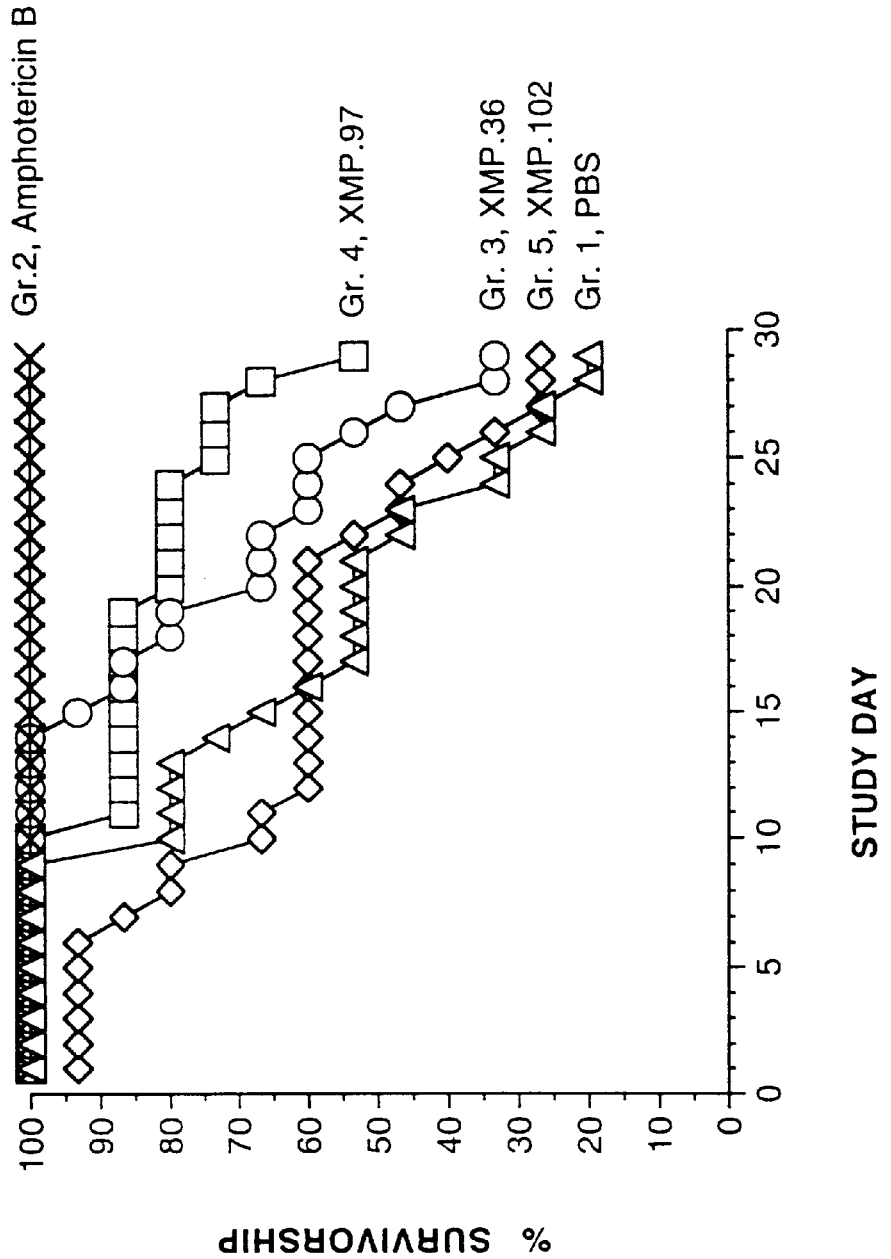
FIGS. 4, 5, and 6 graphically represent survival data in mice after *C. albicans* challenge and treatment with peptides or buffer control.

A Candida inoculation of approximately $1 \times 10^5$ cells resulted in an $LD_{80}$ over 28 days in this model. Immediately after fungal challenge, the mice were intravenously injected via the tail vein with a 0.1 mL volume of 10 mg/kg XMP.36, 5 mg/kg XMP.97, 10 mg/kg XMP.102, 1 mg/kg amphotericin B (Sigma, St. Louis, Mo.), or phosphate buffered saline (PBS) as a control. Treatment with the same amounts of peptides, amphotericin B or PBS was repeated at Day 2 and Day 4 (except that the second dose of XMP.36 was given at a dose of 5 mg/kg). Mice were monitored twice daily for mortality until termination of the study at Day 28. The mortality data, displayed in FIG. 4, show that 100% of the mice treated with amphotericin B survived, 53% of mice treated with XMP.97 survived ($p<0.05$ compared to control), 33% of mice treated with XMP.36 survived, 27% of mice treated with XMP.102 survived, and 20% of mice treated with PBS survived until Day 28. In FIG. 4, the symbol "X" represents survival after treatment with amphotericin B; open squares, treatment with XMP.97; open circles, treatment with XMP.36; open diamonds, treatment with XMP.102; and open triangles, treatment with buffer. Statistical significance was evaluated using the Lifetest Survival Curve analysis. [Lawless, *Statistical Models and Methods for Lifetime Data*, John Wiley & Sons, New York (1982).] The duration and almost linear decline in survival is analogous to human opportunistic candidiasis.

Figure 5:
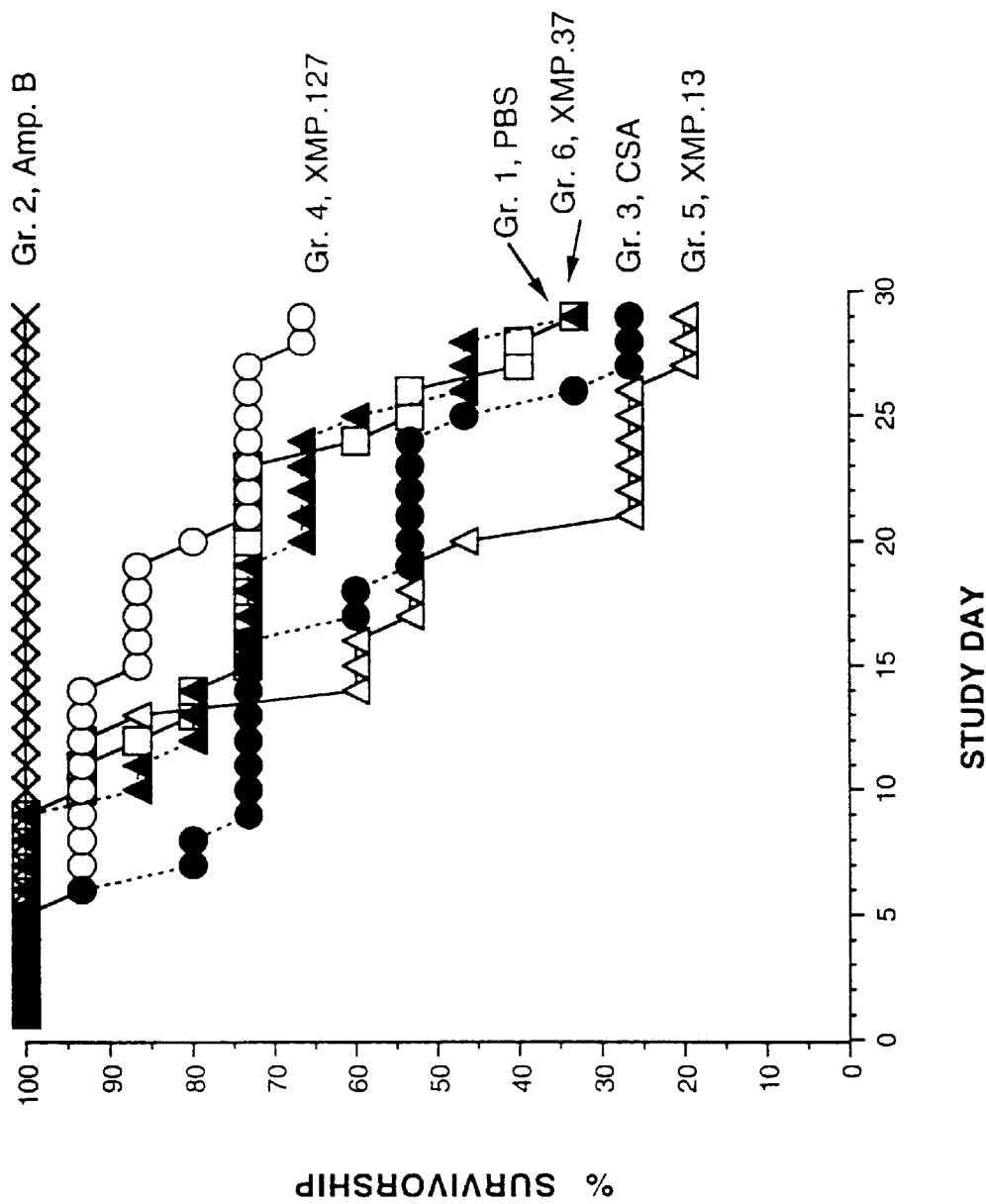

In additional 3-dose studies, groups of 15 mice were injected with a fungal challenge of $0.5 \times 10^5$ Candida cells, prepared for injection as described above, followed by treatment at Day 0, Day 2 and Day 5 with a 0.1 mL volume of 10 mg/kg XMP.127, 5 mg/kg XMP.13, 5 mg/kg XMP.37, 1 mg/kg amphotericin B, or PBS as a control. The morality data are displayed in FIG. 5; 100% of the mice treated with amphotericin B survived, 67% of mice treated with XMP.127 survived ($p<0.05$ compared to control), 33% of mice treated with XMP.37 survived, 20% of mice treated with XMP.13 survived, and 33% of mice treated with PBS survived until Day 28. In FIG. 5, the symbol "X" represents survival after treatment with amphotericin B; open circles, treatment with XMP.127; filled triangles, treatment with buffer; open squares, treatment with XMP.37; open triangles, treatment with XMP.13.

In these 3-dose studies, amphotericin B was completely protective, as expected. The effect of XMP.102, a control peptide without anti-fungal activity as determined by a radial diffusion assay as described in Example 2, was no different from PBS. The data demonstrate that administration of peptides XMP.97 and XMP.127 to mice challenged systemically with *C. albicans* unexpectedly provided a significant reduction in mortality compared with buffer-treated controls.

Figure 6:
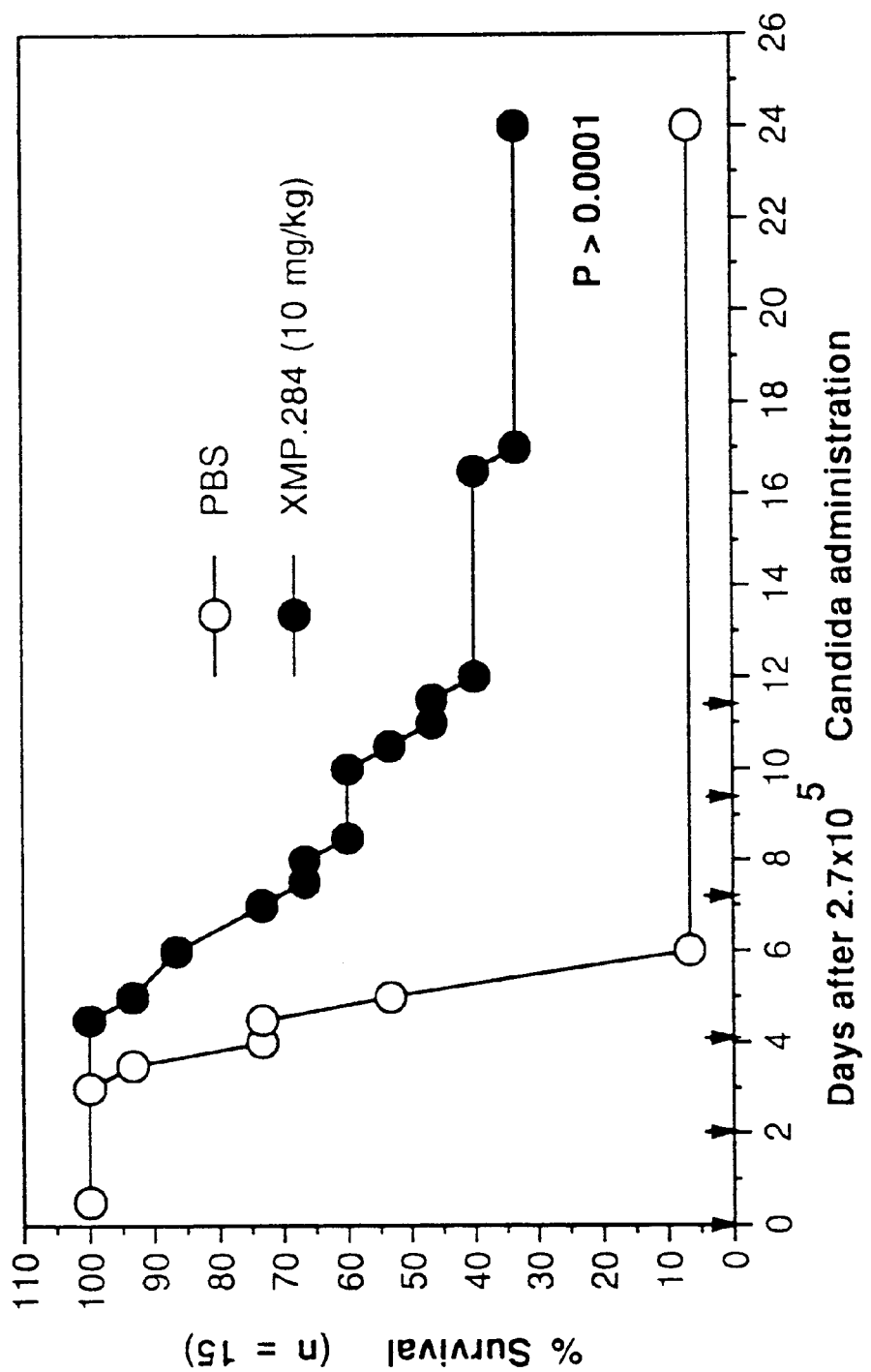

Further studies to determine the effectiveness of anti-fungal peptides were performed at an increased dosing regimen (6 doses rather than 3 doses as described above). Groups of 9 week-old male DBA/2J mice were inoculated with concentrations of $2.7 \times 10^5$ Candida cells (prepared as described above) by intravenous injection in the tail vein. Immediately after fungal challenge, the mice were treated with a 0.1 mL volume of 10 mg/kg XMP.284, 1 mg/kg amphotericin B or PBS as a control at Day 0, Day 2, Day 4, Day 7, Day 9 and Day 11. All amphotericin B-treated animals were protected. The results for XMP.284 (closed circles) and PBS control (open circles) are displayed in FIG. 6. The mortality data showed that only one of the PBS-treated animals survived injection with $2.7 \times 10^5$ Candida at Day 6 through Day 24 (6% survival), however, XMP.284 protected 13 animals (87% survival) at Day 6 and 3 animals (33% survival) at Day 24.

Additional 6-dose experiments were conducted as described above, using inocula of 0.5–3.0×10$^5$ Candida cells and using 0.01, 0.05, 0.1, 0.5, 1.0 or 5.0 mg/kg doses of peptide. The results are summarized in Table 9 below.

TABLE 9

| Peptide | Dose (mg/kg) | P-value[a] |
|---|---|---|
| XMP.268 | 5, 0.5 | b, b |
| XMP.327 | 5, 0.5 | b, b |
| XMP.332 | 5, 0.5 | b, b |
| XMP.333 | 5, 0.5 | b, b |
| XMP.334 | 5, 0.5 | 0.002, 0.001 |
| XMP.335 | 5, 0.5 | b, b |
| XMP.338 | 5, 0.5 | b, b |
| XMP.342 | 5, 0.5 | 0.02, b |
| XMP.344 | 5, 0.5 | 0.0005, 0.0004 |
| XMP.345 | 5, 0.5 | 0.0001, 0.0001 |
| XMP.347 | 5, 0.5 | 0.0001, 0.0001 |
| XMP.348 | 0.5 | 0.0001 |
| XMP.349 | 5, 0.5 | 0.0003, b |
| XMP.352 | 5, 0.5 | b, b |
| XMP.353 | 5, 0.5 | 0.0001, 0.0002 |
| XMP.355 | 5, 0.5 | b, b |
| XMP.356 | 1, 0.5 | b, b |
| XMP.357 | 5, 0.5 | b, 0.01 |
| XMP.358 | 5, 0.5 | b, b |
| XMP.363 | 5, 0.5 | 0.0001, 0.0001 |
| XMP.364 | 5, 0.5 | 0.0002, b |
| XMP.365 | 0.5, 0.1, 0.05, 0.01 | 0.0001, 0.01, 0.0008, 0.0002 |
| XMP.366 | 0.5, 0.1, 0.05, 0.01 | 0.0001, b, b, b |
| XMP.367 | 5, 0.5 | 0.001, b |
| XMP.368 | 5, 0.5 | b, b |
| XMP.369 | 5, 0.5 | b, b |
| XMP.370 | 5, 0.5 | b, b |
| XMP.371 | 5, 0.5 | b, b |
| XMP.372 | 5, 0.5 | b, b |
| XMP.373 | 5, 0.5 | b, b |
| XMP.374 | 0.5 | b |
| XMP.375 | 5, 0.5 | b, b |
| XMP.376 | 5, 0.5 | b, b |
| XMP.377 | 5, 0.5 | b, b |
| XMP.381 | 5, 0.5 | b, b |
| XMP.385 | 5, 0.5 | b, b |
| XMP.386 | 5, 0.5 | b, b |
| XMP.387 | 5, 0.5 | b, b |
| XMP.388 | 5, 0.5 | 0.003, b |
| XMP.389 | 5, 0.5 | 0.0003, b |
| XMP.391 | 5, 0.5 | 0.05, b |
| XMP.410 | 5, 0.5 | b, b |
| XMP.414 | 1, 0.5 | b, b |
| XMP.416 | 0.5 | 0.02 |

[a]P-values vs. saline are derived from Kaplan-Meier survival analysis
b not statistically better than saline (P > 0.05)

An in vivo fungicidal assay was developed to study the comparative efficacy of peptides and Amphotericin B (AmpB) to reduce fungal load in the kidneys of mice systemically infected with *Candida albicans*. Experiments were designed to determine the extent of fungal clearance from the kidneys following peptide or AmpB treatment as follows.

Inoculation of male DBA/2 mice (Charles River Labs) with 6×10$^4$ *C. albicans* and administration of saline, AmpB or peptide was performed on Day 0 via intravenous injection into the tail vein. All groups (n=6) received equal *C. albicans* challenge (standard inoculum of 1.0–1.5×10$^5$ reduced by half to avoid mortality) and equal total volume of sterile saline or antifungal agent per injection. Treatment was initiated immediately after inoculation. All mice were dosed q.d. or q.o.d. with saline, peptide or Amp B. At study termination on Day 4, all animals were sacrificed by $CO_2$ asphyxiation and their kidneys excised for Candida re-isolation.

Specifically, immediately following animal sacrifice, both kidneys were excised, and adrenal glands and adhering tissue removed. Pairs of kidneys were placed immediately into pre-weighed 15 mL conical tubes containing 5 mL sterile saline plus a 1:100 dilution of a 10 mg/mL stock solution of penicillin/streptomycin. Tubes were weighed again, and the difference recorded as "kidney gram fresh weight." Tubes were stored on ice until organ maceration.

For Candida re-isolation and CFU determination, a glass-on-glass tissue homogenizer (Tenbroeck Tissue Grinder, 15 mL, Wheaton) was washed with soap and water, rinsed, and sterilized for 2 minutes with ice-cold 70% ethanol. Following decanting of the ethanol, homogenizers were rinsed with sterile PBS, which was also decanted. Then 5 mL of saline/antibiotics and kidneys were added to the prepared homogenizer and ground until kidney capsules were free of adhering tissue. 2 mL of this homogenate was transferred sterilely to a clean tube on ice. 100 μL of homogenate (serially diluted in sterile PBS) were plated onto Sabouraud Dextrose Agar plates and incubated at 37° C. overnight. Colonies were enumerated, CFU and CFU/GFW calculated, and results analyzed by ANOVA and Fisher's PLSD. The results of assays with representative peptides are shown in Table 10.

TABLE 10

| Peptide | Dose (mg/kg) | Dose Regimen | P-value[a] |
|---|---|---|---|
| XMP.366 | 0.5 | single dose | 0.0005 |
|  | 0.1 | q.d | b |
|  | 0.05 | q.d., b.i.d. | b, b |
|  | 0.01 | q.d., b.i.d. | 0.008, b |
| XMP.342 | 5 | q.d., q.o.d. | b, b |
|  | 1 | q.d. | b |
| XMP.391 | 5 | q.d., q.o.d. | 0.002, b |
|  | 1 | q.d. | b |
| XMP.373 | 5 | q.d., q.o.d. | b, b |
|  | 1 | q.d. | b |
| XMP.353 | 5 | q.d., q.o.d. | b, b |
|  | 1 | q.d. | b |

[a]P-values vs. saline are derived from Kaplan-Meier survival analysis
b not statistically better than saline (P > 0.05)

Figure 7:
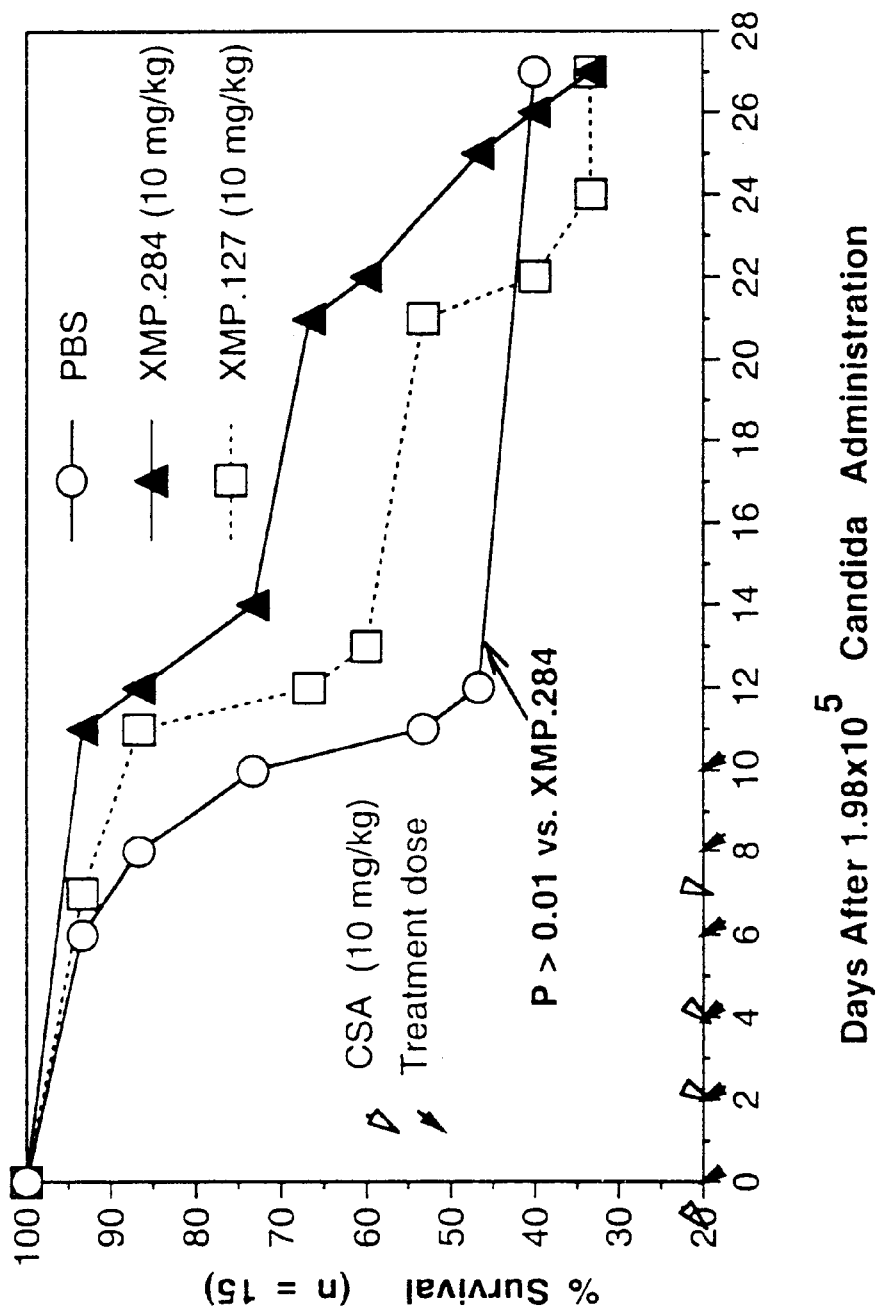
FIG. 7 graphically represents survival data in cyclosporin-treated mice after *C. albicans* challenge and treatment with peptides or buffer control.

Studies were also performed to determine the effectiveness of representative anti-fungal peptides in cyclosporin A-immunosuppressed mice systemically infected with *Candida albicans* SLU-1. Groups (15 animals/group) of 9 week-old male DBA/2J mice were immunosuppressed by pretreatment with 10 mg/kg (Day-1) of cyclosporin A administered by intraperitoneal injection. One day later (Day 0), the mice were inoculated with 2×10$^5$ Candida cells by intravenous injection in the tail vein. Immediately after fungal challenge, the mice were treated with a 0.1 mL volume of 10 mg/kg XMP.284, 10 mg/kg XMP.127, or PBS as a control. Cyclosporin A injections were repeated at Day 1. Day 3. Day 7, and Day 9. XMP.284, XMP.127 or PBS injections were repeated at Day 2, Day 4, Day 6, Day 8 and Day 10. All amphotericin B-treated animals were protected. The results displayed in FIG. 7 of the mortality data after treatment with XMP.127 (open squares), XMP.284 (closed triangles) and PBS control (open circles) show that the immunosuppressed mice are more susceptible to Candida infection as expected. However. XMP.284 and to a lesser extent XMP.127, provided protection against the infection as measured by increased survival compared with PBS controls.

Further in vivo experiments with or without cyclosporin A immunosuppression are performed to confirm the in vitro anti-fungal activity of peptides as described in Example 3 on strains of Candida considered resistant to other anti-fungal agents: polyene-resistant *C. albicans* (ATCC Accession No. 38247). 5-fluorocytosine-resistant *C. albicans* (ATCC No. 44373), azole-resistant *C. albicans* (ATCC No. 62342), and ketoconazole-resistant *C. albicans* (ATCC No. 64124).

EXAMPLE 5

Serum Stability Assays

This example addresses the serum stability of Domain III derived peptides and the effect of serum degradation using HPLC and bioassay.

For these serum stability experiments, peptides were prepared by solid phase peptide sythesis and purified to 94% or greater purity as described in Example 1. Blood was collected from metaphane anesthesized rats by aortic bleed into Vacutainer™ tubes and allowed to clot at room temperature for approximately 30 minutes, then centrifuged at 3000 rpm (about 1000×g) for 10 minutes at room temperature and the serum aspirated. In addition, frozen human serum (North American Biologics, Inc., Miami, Fla., cat. no. 2140, lot no. 94115) was thawed at room temperature and filtered through a 0.45 μm membrane before use.

A 1 mg/mL solution of an exemplary XMP peptide to be tested was added to an equal volume of either rat or human serum described above and maintained at 37° C. At 0, 1, 2, and 4 hours, 100 μL were removed and processed by solid phase extraction for HPLC analysis as follows. Serum samples were prepared for HPLC using C-18 Sep-Pak cartridges (1 mL cartridge with 100 mg of sorbent, Waters Corp., Milford, Mass.). One hundred μL of serum sample were added to an equal volume of 1% TFA and mixed for 30 seconds on a Vortex mixer. The sample was then applied to a C-18 Sep-Pak cartridge that had been conditioned by washing with 1 mL of methanol followed by 1 mL Milli-Q water. Weakly reed components were eluted by washing with 1 mL of 0.1% TFA. The bound peptide was eluted with two volumes of 250 μL 80% acetonitrile/0.065% TFA.

The material eluted from the Sep-Pak cartridge was analyzed on a Michrom Ultaafast Microprotein Analyzer equipped with a 150 mm×1 mm, 5μ particle, 300 Å pore C-8 Zorbax column. The column oven was set to 40° C., the flow rate was 100 μL/minute, and injection volumes were typically 5–10 μL. HPLC was performed using 5% acetonitrile/0.1% TFA in water as mobile phase A, and 80% acetonitrile/0.065% TFA as mobile phase B. The eluate was monitored spectiophotometrically at 214 nm. Peptide standards were dissolved in mobile phase A at 0.1 mg/mL. The gradient was 25–35% B/10 minutes followed by a 5 minute wash step of 100% B and reequilibration at 25% B for 10 minutes.

The peptides identified and purified after serum incubation as described above were subjected to N-terminal peptide sequencing performed on an Applied Biosystems Model 477A/120A sequencer and to electrospray ionization mass spectrometry (ESI/MS) performed using a VG Biotech Bio-Q Mass Spectrometer. In addition, the peptides identified and purified after serum incubation as described above were also tested for their anti-fungal activity in a radial diffusion bioassay with *Candida albicans* SLU-1 strain as described in Example 2.

For these experiments, representative Domain III derived peptides XMP.97, XMP.327, XMP.332 and XMP.333 were used. The serum stability of each differed substantially. For example, XMP.97 was degraded in serum with a half-life of 59 minutes under the described assay conditions. Two metabolites of XMP.97 were detected and were determined to be cleavage products where the cleavage at the amino terminus yielded peptides shortened by either one or two amino acids. The degradation products and kinetics were similar for commercially obtained human serum or freshly prepared rat serum. Other metabolic products of XMP.97 were presumably present but in concentrations below detection limits.

The chemical changes observed after serum incubation of a peptide were generally accompanied by a loss in activity as determined in the radial diffusion assay with Candida. For example. XMP.327 was degraded with a serum half-life of 40 minutes under the described HPLC assay conditions. The serum half-life of XMP.327 as determined by anti-fungal activity in the radial diffusion assay was 43 minutes. In other cases, there may be a difference between the rate of disappearance of anti-fungal activity and the rate of peptide disappearance, indicating that certain metabolites may have activity.

The enzymes responsible for peptide degradation were not specifically identified in these experiments. However, aminopeptidases present in serum are capable of removing one or more residues from the N-terminus of peptides. [See, e.g., Hooper, N. M. Ectopeptidases, in *Biological Barriers to Protein Delivery*, pp.23–50, eds., Audus and Raub, Plenum Press, New York, 1993]. Aminopeptidase N (EC 3.4.11.2), for example, has a broad substrate specificity, releasing the N-terminal amino acid from unblocked peptides. Based on sites of potential hydrolysis, peptides can be designed to minimize certain degradation pathways. Serum degradation at specific amino acids within a peptide may be avoided by incorporation of D-amino acids or other atypical amino acids, and/or by cyclization to prevent protease recognition.

In additional studies, peptides were designed to have increased serum stability. For example, peptides were synthesized using one or more D-amino acids. Also, peptides were synthesized and then their N-terminus was acetylated as described in Example 1. For example, XMP.333 was synthesized having the same amino acid sequence as XMP.327, except that the amino-terminal lysine residue used for synthesis was a D-amino acid. When XMP.333 was tested, its serum half-life as determined in the radial diffusion assay was 130 minutes (as compared with 43 minutes for XMP.327). These results indicate that a single D-amino acid at the N-terminus prevents some degradation and increases the half-life of the peptide.

Peptide constricts can be prepared with increased half-life, but may not maintain the same in vitro activity. For example, XMP.327 had a serum half-life of 43 minutes and activity in radial diffusion of 353 pmol (see Table 1). Peptide XMP.331 having the same amino acid sequence of XMP.327 but having an acetylated N-terminus, had an increased serum half-life of 280 minutes as detected by HPLC analysis, but a decreased activity of>3,493 pmol (see Table 1) as compared with the non-acetylated XMP.327. However, even with decreased in vitro activity, such a peptide may have increased efficacy in vivo due to its increased stability.

Other peptide constructs can be prepared with not only significantly increased stability but also with maintained anti-fungal activity in the radial diffusion assay. For example, XMP.332 was synthesized using all D-amino acids and is the inverse sequence of XMP.327. Such a "retro-D" peptide should be resistant to serum enzymes that recognize and hydrolyze the peptide bond between L-amino acids. In fact, XMP.332 did not show any decrease in activity or decrease in peptide concentration over a 6 hour period of serum incubation. Such a peptide construct, which can maintain the in vitro equivalent molar activity to its L-amino acid peptide counterpart and shows increased serum half-life, may have increased efficacy in vivo. The half-life of the activity in serum as measured by radial diffusion assays and the half-life of peptide in serum as detected by HPLC analysis are shown in Table 11 for representative peptides.

TABLE 11

| Peptide (SEQ.ID NO.) | Peptide Amino Acid Segment | Activity in Serum t ½ (hr.) | HPLC Peptide in Serum t ½ (hr.) |
|---|---|---|---|
| XMP.13 (4) | 141-169 | indefinite | 2.5 |
| XMP.97 (31) | 148-161, K @ 152 (G) | 22.7 | 1.0 |
| XMP.132 (52) | 148-161, PYR @ 153 (W) | 9.7 | NT |
| XMP.133 (53) | 148-161, p-Amino-F @ 153 (W) | 14.0 | NT |
| XMP.139 (58) | 148-161, Y @ 153 (W) | 10.6 | NT |
| XMP.268 (108) | 148-161, V @ 153 (W), A @ 154 (L) | 15.3 | NT |

TABLE 11-continued

| Peptide (SEQ.ID NO.) | Peptide Amino Acid Segment | Activity in Serum t ½ (hr.) | HPLC Peptide in Serum t ½ (hr.) |
|---|---|---|---|
| XMP.284 (117) | 149-161, K @ 152 (G) | 14.6 | 4.2 |
| XMP.327 (160) | K - K - 153 - 157 - K - K | 2.7 | 1.1 |
| XMP.331 (162) | † K - K - 153 - 157 - K - K | inactive | 4.0 |
| XMP.332 (163) | $K_D$ - $K_D$ - $L_D$ - $Q_D$ - $I_D$ - $L_D$ - $W_D$ - $K_D$ - $K_D$ | indefinite | indefinite |
| XMP.333 (164) | $K_D$ - K - 153 - 157 - K - K | 2.2 | 2.3 |
| XMP.334 (165) | $P_D$ - K - 153 - 157 - K - K | 4.7 | 3.2 |
| XMP.335 (166) | P - K - 153 - 157 - K - K | 1.3 | 2.9 |
| XMP.337 (168) | H - H - 153 - 157 - H - H | inactive | NT |
| XMP.338 (169) | ORN - ORN - 153 - 157 - ORN - ORN | 4.7 | NT |
| XMP.342 (173) | $K_D$ - $K_D$ - 153 - 157 - $K_D$ - $K_D$ | indefinite | 5.2 |
| XMP.344 (175) | K - K - 153 - 157 - K - K, A @ 154 (L) | 3.3 | 0.6 |
| XMP.345 (176) | K - K - 153 - 157 - K - K, A @ 157 (L) | 2.7 | 1.4 |
| XMP.347 (178) | K - K - 153 - 157 - K - K, β(2-naphthyl) $A_D$ @ 153 (W), L @ 156 (Q) | 5.2 | 2.5 |
| XMP.348 (179) | K - K - K - 153 - 157 - K - K | 5.5 | NT |
| XMP.349 (180) | K - K - 153 - 157 - K - K - K | 3.3 | 1.4 |
| XMP.351 (182) | K - K - 153 - 158 - K - K | 0.4 | NT |
| XMP.352 (183) | K - K - 153 - 161 | 1.2 | 0.7 |
| XMP.353 (184) | P - 153 - 161* | 0.9 | NT |
| XMP.355 (186) | P - 153 - 161 | 5.7 | 3.2 |
| XMP.356 (187) | † P - 153 - 161 | 0.9 | NT |
| XMP.357 (188) | K - 153 - 160 - P | 0.8 | |
| XMP.358 (189) | K - K - 153 - 160 - P | 1.6 | |
| XMP.363 (194) | $K_D$ - $W_D$ - 154 - 159 - $K_D$ - $K_D$ | indefinite | 11.8 |
| XMP.364 (195) | † $K_D$ - $W_D$ - 154 - 159 - $K_D$ - $K_D$ | indefinite | 25.0 |
| XMP.365 (196) | $K_D$ - $W_D$ $L_D$ -$I_D$ $Q_D$ - $L_D$ $F_D$ - $H_D$ - $K_D$ - $K_D$ | 15.1 | 26.3 |
| XMP.366 (197) | † $K_D$ - $W_D$ $L_D$ -$I_D$ $Q_D$ - $L_D$ $F_D$ - $H_D$ - $K_D$ - $K_D$ | 11.7 | 14.0 |
| XMP.367 (198) | $K_D$ - $K_D H_D$ - $F_D$ -$L_D$ - $Q_D$ - $I_D$ $L_D$ - $W_D$ - $K_D$ | indefinite | 52.4 |
| XMP.368 (199) | † $K_D$ - $K_D$ - $H_D$ - $F_D$ -$L_D$ - $Q_D$ - $I_D$ $L_D$ - $W_D$ - $K_D$ | 25.2 | 34.1 |
| XMP.369 (200) | 152 - 161, K @ 152(G), ORN @ 156 (Q) | 1.4 | 0.6 |
| XMP.370 (201) | 152-161, K @ 152(G), ORN @ 156 (Q) | 4.7 | 2.9 |
| XMP.371 (202) | 152 - 161, K @ 152 (G), DAB @ 156 (Q) | 0.9 | |
| XMP.372 (203) | † 152 - 161, K @ 152 (G), DAB @ 156(Q) | 1.4 | 6.6 |
| XMP.373 (204) | † 152 - 161, K @ 152 (G) | 1.8 | 2.6 |
| XMP.374 (205) | $K_D$ - $L_D$ - $Q_D$ - $I_D$ - $L_D$ - $W_D$ - $K_D$ - $K_D$ | indefinite | indefinite |
| XMP.375 (206) | $K_D$ - $K_D$ - $W_D$ - $A_D$ - $I_D$ - $Q_D$ - $L_D$ - $K_D$ - $K_D$ | indefinite | indefinite |
| XMP.376 (207) | $K_D$ - $K_D$ - $L_D$ - $Q_D$ - $I_D$ - $A_D$ - $W_D$ - $K_D$ - $K_D$ | indefinite | indefinite |
| XMP.377 (208) | K - K - K - W - A - I - Q - L-K - K | 1.8 | NT |
| XMP.379 (210) | K - K - P - W - A - I - Q - L-K - K | 0.3 | 0.8 |
| XMP.381 (212) | K - K - L - Q - L - L - L - K - K | 0.8 | NT |
| XMP.385 (216) | K - K - L - L - L - L - L - K - K | 2.7 | NT |
| XMP.386 (217) | 152 - 161, K @ 152 (G), A @ 154 (L) | 0.9 | NT |
| XMP.387 (218) | 152 - 161, P @ 152 (G), A @ 154 (L) | 2.3 | 2.8 |
| XMP.388 (219) | 152 - 161 | 1.4 | 0.4 |
| XMP.389 (220) | 151 - 161, K @ 151 (V) | 1.6 | 1.3 |
| XMP.391 (222) | 150 - 161 | 4.7 | 1.0 |
| XMP.410 (241) | $CH_3$ - $(CH_2)_6$ - CO - XMP.344 | 2.9 | NT |
| XMP.411 (242) | $CH_3$ - $(CH_2)_{10}$ - CO - XMP.344 | 4.2 | 9.7 |

EXAMPLE 6

Structure/Function Studies

This example addresses the design and assay of antifungal peptides for structural motif and minimum functional sequence analysis.

As shown in Examples 2, 3, and 4 above, XMP.97 was determined to have significant in Vitro activity against C. albicans and significant in vivo activity in a mouse systemic candidiasis model. The sequence was derived from XMP.13 with a lysine substitution for glycine at position 152 in the BPI sequence. As shown in Example 5, sequential N-terminal amino acid removal was observed when the peptides, including XMP.97, were incubated with serum. The 13 amino acid peptide XMP.284 (SKVKWLIQLFHKK-amide; SEQ. ID. NO:117) was synthesized, purified (97%) and tested for anti-fungal activity. The in vitro activity was surprisingly not appreciably diminished (see Table 1). A deletion series of 35 peptides was generated from this starting sequence. All possible N- and C-terminal deletion 12-mers through 6-mers (XMP.285-XMP.319) were synthesized as shown in Table 12 below.

Crude peptides were assayed for an initial purity as described in Example 1 and for in vitro activity with the radial diffusion fungicidal assay as described in Example 2. The nmol value shown in Table 12 represents a calculated value (log titration curve) for the number of nanomoles required to achieve a net 30 $mm^2$ zone in the assay. In purifying XMP.97 and XMP.284, a significant change was observed in the pmol value upon purification. The magnitude of change was larger than observed with other crude peptides and was likely due to removal of inactive peptide impurities. Thus, final comparisons were made using peptides purified as described in Example 1, and preferably asssayed on the same day.

The most active crude peptides were purified by HPLC and re-assayed. The results are shown in Table 12. From this analysis, as demonstrated by Table 12, XMP.293 was the smallest peptide with an increase in molar activity relative to peptide XMP.97. XMP.297 was also equivalent to XMP.284 in activity. Interestingly, XMP.298 was within two-fold of XNT.297. Activity was demonstrable even with 6 amino acid peptides, such as XMP.315, however, this level of activity was decreased by about 3 orders of magnitude compared with the activity of the starting sequence.

These data demonstrate that one group of Domain III derived peptides of the invention are described and defined by a structural motif consisting of a core of 4 to 6, preferably 5 to 6, amino acids where the core contains one neutral hydrophilic residue in the middle of hydrophobic amino acids, and where the core is bounded or flanked at the N- and/or C-terminus by cationic amino acids. Preferred core sequences include: LIQL, IQLF, WLIQF, LIQLF and WLIQLF. Preferred cationic amino acids include: K (most preferred), R, H, ornithine (ORN) and diaminobutyric acid (DAB). Peptides with such a motif possess optimal activity. Activity was observed, but was somewhat diminished, when the peptide contained all of the cationic residues on the C-terminus (e.g., XMP.298) or on the N-terminus (e.g., XMP.300) of the core. Peptides XMP.320–XMP.368 were designed and prepared consistent with this motif, and provide additional support for the structural motif and minimum functional characterization sequence of antifungal peptides according to the invention.

TABLE 12

| Length in a.a.[a] | Peptide | MW | 148 | 149 | 150 | 151 | 152[cab] | 153 | 154 | 155 | 156 | 157 | 158 | 159 | 160 | 161 | Plate Assay (nmol)[b] | Crude Purity (%) | Plate Assay (nmol)[c] |
|---|---|---|---|---|---|---|---|---|---|---|---|---|---|---|---|---|---|---|---|
| 14 | 97 | 1782 | K | S | K | V | K | W | L | I | Q | L | F | H | K | K | 0.701 | 68 | 0.304 |
| 13 | 284 | 1654 | . | S | K | V | K | W | L | I | Q | L | F | H | K | K | 1.460 | 60 | 0.373 |
| 12 | 285 | 1526 |  | S | K | V | K | W | L | I | Q | L | F | H | K | . | >3.024 | 75 |  |
| 12 | 286 | 1527 |  |  | K | V | K | W | L | I | Q | L | F | H | K | K | 1.216 | 61 | 0.253 |
| 11 | 287 | 1398 |  |  |  | V | K | W | L | I | Q | L | F | H | K | . | >3.509 | 58 |  |
| 11 | 288 | 1439 |  | S | K | V | K | W | L | I | Q | L | F | H | . | . | 3.639 | 78 | 0.279 |
| 11 | 289 | 1439 |  |  | K | V | K | W | L | I | Q | L | F | H | K | K | 1.542 | 78 | 0.68 |
| 10 | 290 | 1261 |  |  |  | V | K | W | L | I | Q | L | F | H | K | . | >2.233 | 79 |  |
| 10 | 291 | 1311 |  |  |  |  | K | W | L | I | Q | L | F | H | K | K | >5.039 | 55 |  |
| 10 | 292 | 1311 |  |  |  | . | K | W | L | I | Q | L | F | H | K | K | >4.063 | 78 |  |
| 10 | 293 | 1340 |  | S | K | V | K | W | L | I | Q | L | F | H | . | K | 1.156 | 78 | 0.215 |
| 9 | 294 | 1113 |  |  |  |  | K | W | L | I | Q | L | F | H | K | . | >4.634 | 63 |  |
| 9 | 295 | 1174 |  |  |  | V | K | W | L | I | Q | L | F | H | . | . | >1.977 | 82 | >2.612 |
| 9 | 296 | 1183 |  |  | K | V | K | W | L | I | Q | L | F | . | . | . | >5.573 | .64 |  |
| 9 | 297 | 1212 |  | S | K | V | K | W | L | I | Q | L | F | . | . | . | 1.817 | 81 | 0.564 |
| 9 | 298 | 1212 |  |  | K | V | K | W | L | I | Q | L | . | H | K | K | 2.628 | 84 | 1.106 |
| 8 | 299 | 1000 |  | S | K | V | K | W | L | I | Q | L | . | . | . | . | >8.768 | 68 |  |
| 8 | 300 | 1026 |  |  |  |  | K | W | L | I | Q | L | F | H | K | . | 1.957 | 75 | 0.993 |
| 8 | 301 | 1045 |  |  |  | . | K | W | L | I | Q | L | F | H | . | . | — | 41 |  |
| 8 | 302 | 1083 |  |  | K | V | K | W | L | I | Q | L | . | . | K | K | >5.497 | 75 | 2.07 |
| 8 | 303 | 1083 |  |  |  | V | K | W | L | I | Q | L | F | H | K | . | >4.694 | 78 | 1.306 |
| 8 | 304 | 1025 |  |  |  |  | K | W | L | I | Q | L | F | . | K | K | >8.290 | 84 |  |
| 7 | 305 | 872.1 |  | S | K | V | K | W | L | I | . | . | . | . | . | . | >10.228 | 73 |  |
| 7 | 306 | 913.2 |  |  |  |  | K | W | L | I | Q | L | . | . | . | . | >10.485 | 62 |  |
| 7 | 307 | 898 |  |  |  | V | K | W | L | I | Q | L | . | . | . | . | >8.345 | 67 |  |
| 7 | 308 | 946 |  |  |  |  |  |  |  |  |  | . | F | H | K | K | — | 72 |  |
| 7 | 309 | 955 |  |  |  |  |  |  |  | I | Q | L | F | H | K | K | — | 76 |  |
| 7 | 310 | 897 |  |  |  | . | . | W | L | I | Q | L | F | H | K | . | >9.475 | 56 |  |
| 7 | 311 | 912 |  |  |  | . | . | . | L | I | Q | L | F | H | K | . | 77 |  |  |
| 6 | 312 | 759 |  |  |  | . | . | . | . | I | Q | L | F | H | K | . | >11.20 | 76 |  |
| 6 | 313 | 785 |  |  |  | . | K | L | I | Q | L | F | F | H | K | . | >11.05 | 59 |  |
| 6 | 314 | 785 |  |  |  | K | W | . | I | . | . | . | . | . | ? | . | 13.497 | 73 |  |
| 6 | 315 | 799 |  |  | . | K | W | . | I | Q | . | . | . | . | K | . | >5.069 | 84 |  |
| 6 | 316 | 818 |  |  | . | . | W | L | . | Q | L | F | H | . | . | . | 11.1 | 85 |  |
| — | 317 | 769 |  |  |  |  |  |  |  |  | L | F | H | . | . | — | — | >12.853 |  |
| — | 318 | 784 |  |  |  |  |  |  |  | Q | L | F | H | K | . | — | — | inactive to 11.5 |  |
| — | 319 | 799 |  |  |  |  |  |  |  | Q | L | F | H | K | K | — |  |  |  |

[a] a.a. = amino acids
[b] crude peptide activity
[c] pure peptide activity

EXAMPLE 7

LPS Neutralization Activity of Anti-fungal Peptides

This example addresses the in vitro and in vivo LPS neutralizing activity of Domain III derived peptides.

An in vitro LPS neutralization screening assay for evaluation of Domain III derived peptides was developed (as described in co-owned and co-pending U.S. patent application Ser. No. 08/306,473) which provides both a measure of efficacy of each peptide ($EC_{50}$) and of the toxicity/growth inhibition of each peptide ($IC_{50}$). This sensitive assay for inhibition of cellular proliferation in mouse cells treated with LPS can also be utilized for quantitation of LPS levels in human plasma upon development of a standard curve.

In this assay, mouse RAW 264.7 cells (ATCC Accession No. T1B71), maintained in RPM 1640 medium (GIBCO), supplemented with 10 mM BIEPES buffer (pH 7.4), 2 mM L-glutamine, penicillin (100 U/mL), streptomycin (100 µg/mL), 0.075% sodium bicarbonate, 0.15M 2-mercaptoethanol and 10% fetal bovine serum (Hyclone, Inc., Logan, Utah), were first induced by incubation in the presence of 50 U/mL recombinant mouse γ-interferon (Genzyme, Cambridge. Mass.) for 24 h prior to assay. Induced cells were then mechanically collected and centrifuged at 500×g at 4° C. and then resuspended in 50 mL RPMI 1640 medium (without supplements), re-centrifuged and again resuspended in RPMI 1640 medium (without supplements). The cells were counted and their concentration adjusted to $2 \times 10^5$ cells/mL and 100 µL aliquots were added to each well of a 96-well microtitre plate. The cells were then incubated for about 15 hours with E. coli O113 LPS (Control Standard, Assoc. of Cape Cod, Woods Hole, Mass.), which was added in 100 µL/well aliquots at a concentration of 1 ng/mL in serum-free RPMI 1640 medium (this concentration being the result of titration experiments in which LPS concentration was varied between 50 pg/mL and 100 ng/mL). This incubation was performed in the absence or presence of peptides in varying concentrations between 25 ng/mL and 50 µg/mL. Recombinant human $rBPI_{21}$ also designated $rBPI_{21}\Delta cys$, which is rBPI 1–193, with alanine substituted at position 132 for cysteine [see co-owned U.S. Pat. No. 5,420,019] was used as a positive control at a concentration of 1 µg/mL. Cell proliferation was quantitatively measured by the addition of 1 µCi/well [$^3$H]-thymidine 5 hours after the time of initiation of the assay. After the 15-hour incubation, labeled cells were harvested onto glass fiber filters with a cell harvester (Inotech Biosystems, INB-384, Sample Processing and Filter Counting System, Lansing, Mich.).

Figure 8:
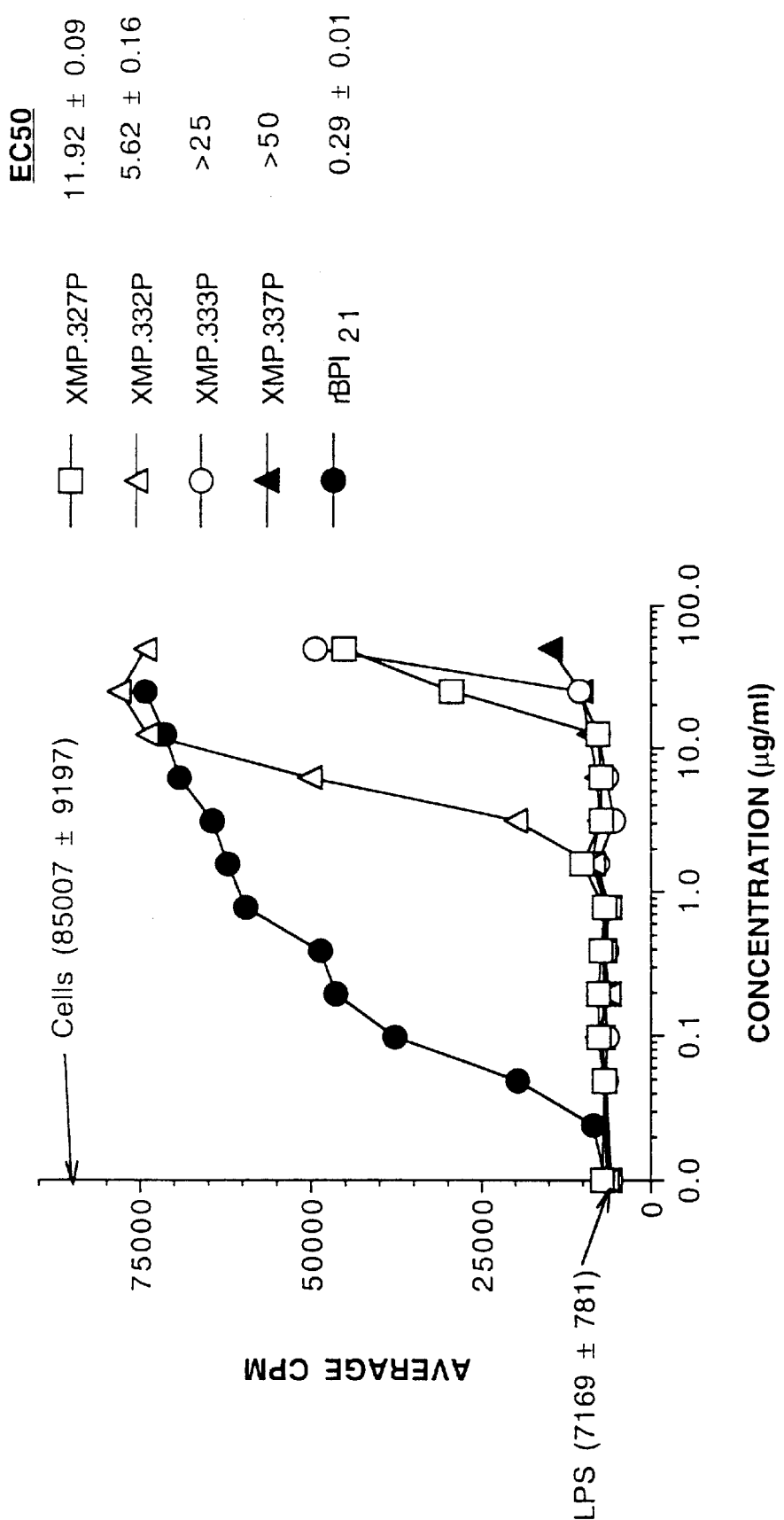
FIG. 8 provides results of RAW cell assay tests of the activity of various peptides.

The LPS-mediated inhibition of RAW 264.7 cell proliferation is dependent on the presence of LBP, as added to the reaction mixture either as a component of serum or as recombinant LBP (at a concentration of 1 µg/mL). Different patterns of peptide behavior are observed in the assay. The Domain III derived anti-fungal peptides with LPS-neutializing activity according to the present invention generally did not exhibit an $IC_{50}$ at the concentrations tested, unlike other XMP peptides including LPS-neutralizing peptides that are not anti-fungal, as described in co-owned and co-pending U.S. applications Ser. Nos. 08/209,762 and 08/306,473. For example, XMP.5 displayed an $EC_{50}$ (i.e., the peptide concentration at which the growth inhibitory effect of LPS was reversed by 50%) of 5.3±0.6 µg/mL; however, an $IC_{50}$ (i.e., the peptide concentration at which RAW cell growth was inhibited by 50% from the value without added LPS or peptide) was not observed at the concentrations tested. The results of a representative assay of exemplary Domain III derived anti-fungal peptides are shown in FIG. 8. The LPS-neutralizing activities of the purified anti-fungal peptides XMP.327 (open squares), XMP.332 (closed squares), XMP.333 (open triangles) and XMP.337 (closed triangles) are shown in FIG. 8. Also shown as a positive control is the activity of $rBPI_{21}$. Results from representative peptides tested with this assay are shown in Table 13.

TABLE 13

| Peptide (SEQ ID NO:) | Peptide Amino Acid Segment | HPLC % Purity | In Vitro LPS Neutralization $EC_{50}^a$ µg/ml | $IC_{50}^b$ µg/ml |
|---|---|---|---|---|
| XMP.97P (31) | 148-161, K @ 152 (G) | 98 | 3.69 ± 0.46 | >25 |
| XMP.127 (47) | 148-161, F @ 153 (W) | 63 | 10.77 ± 1.34 | NA |
| XMP.284P (117) | 149-161, K @ 152 (G) | 96 | 4.72 ± 0.08/ 3.57 ± 0.09 | NA/ >50 |
| XMP.286P (119) | 150-161, K @ 152 (G) | 80 | 4.68 ± 0.26 | NA |
| XMP.288P (121) | 150-160, K @ 152 (G) | 94 | 0.87 ± 0.06 | >25 |
| XMP.295P (128) | 150-158, K @ 152 (G) | NT$^c$ | 3.69 ± 0.12 | >25 |
| XMP.303P (136) | 153-160 | 98 | 11.79 ± 0.85 | NA |
| XMP.327P (160) | K - K - 153 - 157 - K - K | 94 | 11.92 ± 0.09 | NA |
| XMP.330 (161) | 153-156 | 95 | >50 | NA |
| XMP.331P (162) | † K - K- 153 - 157 - K - K | 96 | 14.11 ± 0.35 | NA |
| XMP.332P (163) | $K_D$ - $K_D$ - $L_D$ - $Q_{D-ID-LD}$ - $W_D$ - $K_D$ - $K_D$ | 98 | 5.65 ± 0.16 | NA |
| XMP.333P (164) | $K_D$ - K - 153 - 157 - K - K | 98 | >25 | NA |
| XMP.334P (165) | $P_D$ - K - K - 153 - 157 - K - K | 89 | NA | NA |
| XMP.335P (166) | P - K - 153 - 157 - K - K | 98 | NA | NA |
| XMP.336P (167) | R - R - 153 - 157 - R - R | 97 | NA | NA |
| XMP 337P (168) | H - H - 153 - 157 - H - H | 94 | >50 | NA |
| XMP 338 (169) | ORN - ORN - 153 - 157 - ORN - ORN | 74 | >25 | NA |
| XMP 339P (170) | DAB - DAB - 153 - 157 - DAB - DAB | 98 | NA | NA |
| XMP.340P (171) | p-amino-F - p-amino-F - 153 - 157 - p-amino-F - amino-F | 94 | >50 | NA |
| XMP.341P (172) | PYR - PYR - 153 - 157 - PYR - PYR | 99 >50 | >50/ | NA/NA |
| XMP.342 (173) | $K_D$ - $K_D$ - 153 - 157 - $K_D$ - $K_D$ | 72 | >50 | NA |

TABLE 13-continued

| Peptide (SEQ ID NO:) | Peptide Amino Acid Segment | HPLC % Purity | In Vitro LPS Neutralization EC$_{50}$[a] μg/ml | In Vitro LPS Neutralization IC$_{50}$[b] μg/ml |
|---|---|---|---|---|
| XMP.342P (173) | K$_D$ - K$_D$ - 153 - 157 - K$_D$ - K$_D$ | 97 | NA | NA |
| XMP.344P (175) | K - K - 153 - 157 - K - K, A @ 154 (L) | 96 | >25 | NA |
| XMP.345P (176) | K - K - 153 - 157 - K - K, A @ 157 (L) | 93 | >50 | NA |
| XMP.347P (178) | K - K - 153 - 157 - K - K, β(2-naphthyl) A$_D$ @ 153 (W), L @ 156 (Q) | 97 | 1.65 ± 0.09 | >25 |
| XMP.348P (179) | K - K - K - 153 - 157 - K - K | 97 | | |
| XMP.351P (182) | K - K - 153 - 158 - K - K | 98 | 8.47 ± 0.71 | NA |
| XMP.352P (183) | K - K - 153 - 161 | 98 | 2.34 ± 0.38 | NA |
| XMP.353P (184) | P - 153 - 161* | 99 | 4.42 ± 0.56 | NA |
| XMP.355P (186) | P - 153 - 161 | 99 | 1.08 ± 0.05 | NA |
| XMP.356P (187) | † P - 153 - 161 | >99 | 2.72 ± 0.02 | >25 |
| XMP.359P (190) | C$_D$ - 153 - 161 | 96 | 7.31 ± 1.26 | >25 |
| XMP.361P (192) | K$_D$ - C - 154 - 158 - C - K$_D$ | 96 | >25 | NA |
| XMP.362P (193) | K$_D$ - K- C - 154 - 158 - C - K - K$_D$ | 98 | >50 | NA |
| XMP.363P (194) | K$_D$ - W$_D$ - 154 - 159 - K$_D$ - K$_D$ | 97 | >50 | NA |
| XMP.364P (195) | † K$_D$ - W$_D$ 154 - 159 - K$_D$ K$_D$ | 98 | >25 | NA |
| XMP.365P (196) | K$_D$ - W$_D$ - L$_D$ - I$_D$ - Q$_D$ - L$_D$ - F$_D$ - H$_D$ - K$_D$ - K$_D$ | 97 | 0.52 ± 0.07 | >25 |
| XMP.366P (197) | † K$_D$ - W$_D$ - L$_D$ - I$_D$ - Q$_D$ - L$_D$ - F$_D$ - H$_D$ - | 99 | 3.44 ±0 0.90 | 18.28 ± 2.57 |
| XMP.367P (198) | | | | |
| XMP.368P (199) | † K$_D$ - K$_D$ - H$_D$ F$_D$ - L$_D$ - Q$_D$ I$_D$ L$_D$ - | 93 | 1.95 ± 0.11 | >25 |
| XMP.369P (200) | 152-161, K @ 152(G), ORN @ 156 (Q) | 95 | 12.09 ± 0.43 | NA |
| XMP.370P (201) | † 152-161, K @ 152(G), ORN @ 156 (Q) | >99 | NA | >25 |
| XMP.371P (202) | 152-161, K @ 152 (G), DAB @ 156 (Q) | 97 | NA | >25 |
| XMP.372P (203) | † 152-161, K @ 152 (G), DAB @ 156(Q) | 99 | >25 | >25 |
| XMP.373P (204) | † 152-161, K @ 152 (G) | 98 | 12.79 ± 0.19 | >25 |
| XMP.374P (205) | K$_D$ - L$_D$ - Q$_D$ - I$_D$ - L$_D$ - W$_D$ - K$_D$ - K$_D$ | 97 | 13.97 ± 2.02 | NA |
| XMP.375P (206) | K$_D$ - K$_D$ - W$_D$ - A$_D$ - I$_D$ - Q$_D$ - L$_D$ - K$_D$ - K$_D$ | 95 | >50 | NA |
| XMP.376P (207) | K$_D$ - K$_D$ - L$_D$ - Q$_D$ - I$_D$ - A$_D$ - W$_D$ - K$_D$ - K$_D$ | 92 | >50 | NA |
| XMP.377P (208) | K - K - K - W - A - I - Q - L - K - K | 97 | NA | NA |
| XMP.378P (209) | P - W - A - I - Q - L - K - K | 97 | NA | NA |
| XMP.379P (210) | K - K - P - W - A - I - Q - L - K - K | 98 | NA | NA |
| XMP.380P (211) | K - K - Q - L - L - L - L - K - K | 99 | NA | NA |
| XMP.381P (212) | K - K - L - Q - L - L - L - K - K | 99 | NA | NA |
| XMP.382P (213) | K - K - L - L - Q - L - L - K - K | 99 | NA | NA |
| XMP.383P (214) | K - K - L - L - L - Q - L - K - K | 99 | NA | NA |
| XMP.384P (215) | K - K - L - L - L - L - Q - K - K | 99 | NA | NA |
| XMP.385P (216) | K - K - L - L - L - L - L - K - K | 99 | 2.56 ± 0.23 | >25 |
| XMP.386P (217) | 152-161, K @ 152 (G), A @ 154 (L) | 97 | 9.75 ± 1.02 | NA |
| XMP.387P (218) | 152-161, P @ 152 (G), A @ 154 (L) | | 15.53 ± 2.18 | NA |
| XMP.388P (219) | 152-161 | 97 | 8.08 ± 1.52 | NA |
| XMP.389P (220) | 151-161, K @ 151 (V) | 99 | 1.78 ± 0.09 | NA |
| XMP.390P (221) | 151-161, K @ 151 (V), P @ 152 (G) | | 3.97 ± 0.21 | NA |
| XMP.391P (222) | 150-161 | 97 | 1.49 ± 0.02 | NA |
| XMP.392P (223) | 150-161, P @ 152 (G) | 98 | 24.03 ± 2.67 | NA |
| XMP.393P (224) | 148-161, P @ 152 (G) | | >25 | NA |
| XMP.406P (237) | 147-161, P @ 147 (S), A @ 153 (W) | 99 | >50 | NA |

TABLE 13-continued

| Peptide (SEQ ID NO:) | Peptide Amino Acid Segment | HPLC % Purity | In Vitro LPS Neutralization EC$_{50}$[a] µg/ml | IC$_{50}$[b] µg/ml |
|---|---|---|---|---|
| XMP.407P (238) | 147-162, P @ 147 (S), A @ 153 (W), D @ 162 (I) | 96 | NA | NA |
| XMP.408P (239) | L - K - K - K - W - A - I - Q (cyclized head to tail) | | NA | NA |
| XMP.409P (240) | S - K - 153 - 157 - K - K, A @ 154 (L) | 98 | NA | NA |
| XMP.410 | CH$_3$ - (CH$_2$)$_6$ - CO - XMP.344 | 95 | >25 | NA |
| XMP.411 | CH$_3$ - (CH$_2$)$_{10}$ - CO - XMP.344 | | 2.94 ± 0.14 | >25 |
| XMP.414 | CH$_3$ - (CH$_2$)$_6$ - CO - XMP.365 | | 1.91 ± 0.04 | 10.96 ± 0.52 |
| XMP.415 | CH$_3$ - (CH$_2$)$_{10}$ - CO - XMP.365 | | 1.61 ± 0.03 | 6.80 ± 0.14 |
| XMP.416 | NH$_2$ - (CH$_2$)$_7$ - CO - XMP.365 | | 4.67 ± 0.27 | 24.41 ± 0.78 |
| XMP.417 | NH$_2$ - (CH$_2$)$_{11}$ - CO - XMP.365 | | 3.88 ± 0.20 | 11.26 ± 1.30 |

Figure 9:
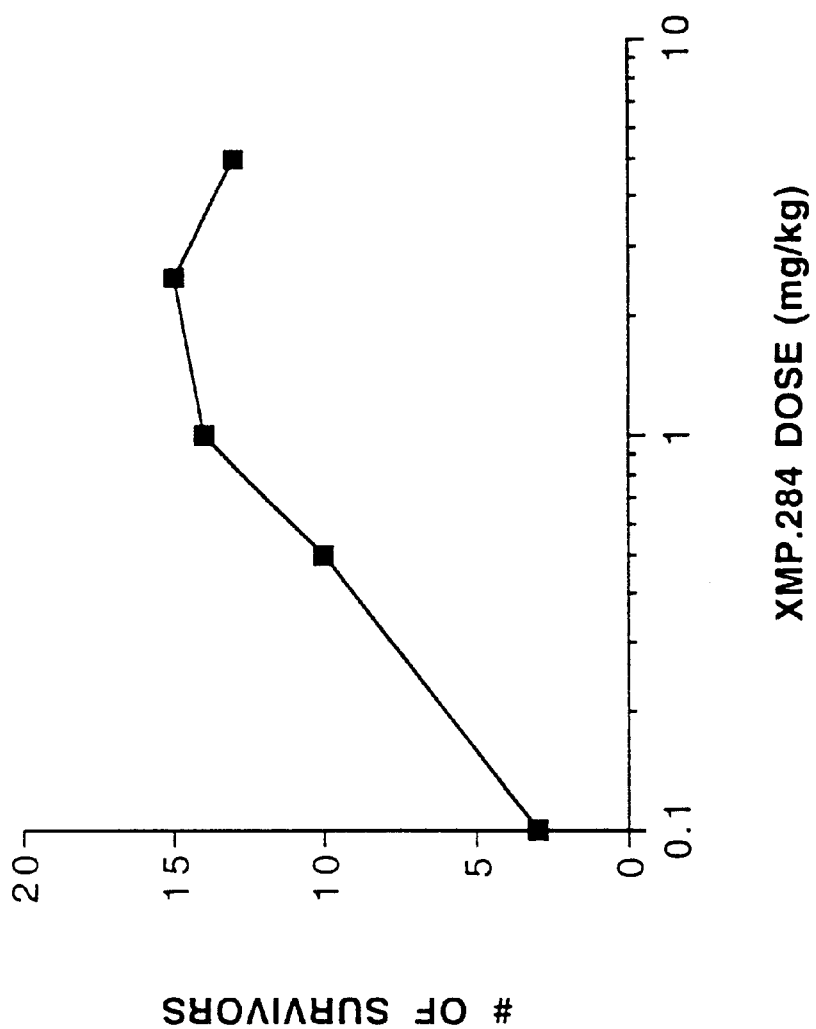
FIG. 9 graphically represents survival data in mice after challenge with *E. coli* 0111: B4 LPS and treatment with peptide.

[a]NA for EC$_{50}$ means no evidence neutralization of LPS at up to 50 µg/ml
[b]NA for IC$_{50}$ means no evidence of decreased RAW cell growth at up to 50 µg/ml
[c]NT = not tested Domain III derived peptides are also tested for LPS neutralizing efficacy in an in vivo mouse experimental endotoxemia model. Groups of 15 mice were administered an intravenous injection of endotoxin (E. coli O111:B4, Sigma Chemical Co., St. Louis, Mo.) at a LD$_{90}$ dosage of 20 mg/kg. This was followed by a second intravenous injection of the peptide to be tested. Injections of saline were used in negative control mice. The animals were observed for 7 days and mortality recorded. The efficacy of the peptides was measured by a decrease in endotoxemia-associated mortality in peptide-injected mice as compared with control mice. XMP.284 is a representative peptide active in this murine model. As shown in FIG. 9, significant protection was observed with a 0.5 mg/kg dose of XMP.284, while at a 1 mg/kg dose, 14 of 15 animals were protected, and a 3 mg/kg dose was effective to protect all treated animals (100% survival). No animals survived in the saline control group.

EXAMPLE 8

Peptide Formulations

This example addresses peptide formulations. A representative Domain III derived peptide XMP.284 was evaluated for stability in liquid formulations containing buffered saline solutions and to elucidate breakdown mechanisms, if any, that might be common to such peptides.

The lyophilized peptide was dissolved to a concentration of 1 mg/mL in three different buffers. The three formulation buffers used were (a) 10 mM solution acetate, 150 mM sodium chloride pH 4, (b) 10 mM sodium acetate, 150 mM sodium chloride pH 5 and (c) 10 mM sodium acetate, 150 mM sodium chloride pH 6. The formulated peptide samples were incubated at 4° C. and 37C. At each time point, samples were withdrawn from each vial and assayed by C18 reverse phase BPLC, absorbance at 280 nm, and SDS-PAGE. The study was conducted for 50 days.

A 0.46×25 cm Vydac C18 column (cat no. 218TP54) was used on a Shimadzu HPLC system. The column was run in binary gradient mobile phases: A=Water+0.05% TFA, B=acetonitrile+0.05% TFA. Chromatocraphic conditions were as follows: wavelength=229 nm; flowrate=1 ml/min; injection volume=50 µL; run time=37 minutes; gradient =20% B to 40% B in 20 minutes; AUFS=0.1 for XMP.284; concentration of sample=3.5 µg per 50 µL injection volume. In preparation for the C18 assay, the samples withdrawn from the vials were diluted 16-fold with 0.05% TFA in water. All samples were filtered through Acrodisc 4 prior to analysis.

Samples were analyzed by SDS polyacrylamide gel electrophoresis, run on Novex 10–20% tricine precast gels (Novex, La Jolla, Calif., EC6625). Samples were mixed with non-reducing sample loading buffer (Novex LC1676, 2x) and heated at 95° C. for two minutes. After cooling, samples were run on the gel and the gels were stained with Coomassie Blue. In addition, samples were analyzed photometrically. For this, samples withdrawn at each time point were diluted 6-fold with Millipore water and absorbance was measured at 280 nm and scanning from 210 nm to 340 nm using a Shimadzu UV 160 spectrophotometer. AU samples were filtered prior to absorbance measurement(s).

XMP.284 was soluble in water and unbuffered saline. XMP.284 was also soluble in 10 mM sodium phosphate, 150 mM sodium chloride pH 7. The peptide remained soluble in the phosphate buffer at 40° C. for 1 hour and then 55° C. for 1 hour. There was very little product loss, as measured by absorbance at 280 nm, in 0.15 M saline buffered with 10 mM acetate at pH 4, 5 or 6. The real time stability study at 4° C. showed that product concentration was unchanged. Even the accelerated stability study at 37° C. showed that graer than 95% of product concentration was maintained and that only low levels (less than 0.5% at 50 days) of new HPLC peaks accumulated with time at 37° C. in the acetate buffered saline formulations. Given the substantial stability exhibited by the Domain III derived peptide as tested, additional excipients may not be necessary but may be desired to further enhance long-term stability and/or activity. Presently preferred is a formulation that includes 10 mM sodium acetate, 150 mM sodium chloride, pH 5.

Numerous modifications and variations in the practice of the invention are expected to occur to those skilled in the art upon consideration of the foregoing description on the presently preferred embodiments thereof. Consequently the only limitations which should be placed upon the scope of the present invention are those that appear in the appended claims.

What is claimed is:

1. A peptide having from six to fourteen amino acids and having the amino acid sequence of bactericidal/permeability-increasing protein from about position 148 to about position 161 of SEQ ID NO: 251, and variants of the sequence having antifungal activity.

2. A peptide according to claim 1 having thirteen or fourteen amino acids.

3. A variant peptide according to claim 1 wherein an amino acid corresponding to G at position 152 is K.

4. An antifungal peptide according to claim 1 having a core amino acid sequence selected from the group consisting of LIQL, IQLF, WLIQL, LIQLF and WLIQLF or a variant core amino acid sequence having at least 75% homology to said core amino acid sequence.

5. A peptide according to claim 1, 2, 3 or 4 having one or more D-isomer amino acids.

6. A peptide according to claim 5 wherein said amino acids comprise D-isomer amino acids in reverse sequence order.

7. A peptide according to claim 1, 2, 3 or 4 wherein the amino terminal amino acid residue is acetylated.

8. A cyclic peptide according to claim 1, 2, 3 or 4.

9. A pharmaceutical composition comprising a peptide according to any one of claims 1 through 4 and a pharmaceutically acceptable diluent, adjuvant or carrier.

10. An in vitro method for killing or inhibiting replication of fungi comprising contacting the fungi with a peptide according to any one of claims 1 through 4.

11. A method of treating fungal infections comprising administering to a subject suffering from a fungal infection a therapeutically effective amount of a peptide according to any one of claims 1 through 4.

12. A method according to claim 11 wherein the fungal infection involves a fungal species selected from the group consisting of Candida, Aspergillus and Cryptococcus species.

13. A method according to claim 12 wherein the Candida species is selected from the group consisting of C. albicans, C. glabrata, C krusei, C. lusitaniae, C. parapsilosis and C. tropicalis.

14. A method according to claim 11 wherein the peptide is administered topically, intravenously, orally or as an aerosol.

15. A method according to claim 11 comprising the additional step of administering a non-peptide anti-fungal agent.

16. A pharmaceutical composition comprising a peptide according to claim 5 and a pharmaceutically acceptable diluent, adjuvant or carrier.

17. An in vitro method for killing or inhibiting replication of fungi comprising contacting the fungi with a peptide according to claim 5.

18. A method of treating fungal infections comprising administering to a subject suffering from a fungal infection a therapeutically effective amount of a peptide according to claim 5.

19. A method according to claim 18 wherein the fungal infection involves a fungal species selected from the group consisting of Candida, Aspergillus and Cryptococcus species.

20. A method according to claim 19 wherein the Candida species is selected from the group consisting of C. albicans, C. glabrata, C. krusei, C. lusitaniae, C. parapsilosis and C. tropicalis.

21. A method according to claim 18 wherein the peptide is administered topically, intravenously, orally or as an aerosol.

22. A method according to claim 18 comprising the additional step of administering a non-peptide anti-fungal agent.

23. A pharmaceutical composition comprising a peptide according to claim 6 and a pharmaceutically acceptable diluent, adjuvant or carrier.

24. An in vitro method for killing or inhibiting replication of fungi comprising contacting the fungi with a peptide according to claim 6.

25. A method of treating fungal infections comprising administering to a subject suffering from a fungal infection a therapeutically effective amount of a peptide according to claim 6.

26. A method according to claim 25 wherein the fungal infection involves a fungal species selected from the group consisting of Candida, Aspergillus and Cryptococcus species.

27. A method according to claim 26 wherein the Candida species is selected from the group consisting of C. albicans, C. glabrata, C. krusel, C. lusitaniae, C. parapsilosis and C. tropicalis.

28. A method according to claim 25 wherein the peptide is administered topically, intravenously, orally or as an aerosol.

29. A method according to claim 25 comprising the additional step of administering a non-peptide anti-fungal agent.

30. A pharmaceutical composition comprising a peptide according to claim 7 and a pharmaceutically acceptable diluent, adjuvant or carrier.

31. An in vitro method for killing or inhibiting replication of fungi comprising contacting the fungi with a peptide according to claim 7.

32. A method of treating fungal infections comprising administering to a subject suffering from a fungal infection a therapeutically effective amount of a peptide according to claim 7.

33. A method according to claim 32 wherein the fungal infection involves a fungal species selected from the group consisting of Candida, Aspergillus and Cryptococcus species.

34. A method according to claim 33 wherein the Candida species is selected from the group consisting of *C. albicans, C. glabrata, C. krusei, C. lusitaniae, C. parapsilosis* and *C. tropicalis*.

35. A method according to claim 32 wherein the peptide is administered topically, intravenously, orally or as an aerosol.

36. A method according to claim 32 comprising the additional step of administering a non-peptide anti-fungal agent.

37. A pharmaceutical composition comprising a peptide according to claim 8 and a pharmaceutically acceptable diluent, adjuvant or carrier.

38. An in vitro method for killing or inhibiting replication of fungi comprising contacting the fungi with a peptide according to claim 8.

39. A method of treating fungal infections comprising administering to a subject suffering from a fungal infection a therapeutically effective amount of a peptide according to claim 8.

40. A method according to claim 39 wherein the fungal infection involves a fungal species selected from the group consisting of Candida, Aspergillus and Cryptococcus species.

41. A method according to claim 40 wherein the Candida species is selected from the group consisting of *C. albicans, C. glabrata, C. krusei, C. lusitaniae, C. parapsilosis* and *C. tropicalis*.

42. A method according to claim 39 wherein the peptide is administered topically, intravenously, orally or as an aerosol.

43. A method according to claim 39 comprising the additional step of administering a non-peptide anti-fungal agent.

* * * * *